(12) United States Patent (10) Patent No.: US 7,449,450 B2
Goldmakher et al. (45) Date of Patent: Nov. 11, 2008

(54) COMPOUNDS, METHODS OF SCREENING, AND IN VITRO AND IN VIVO USES INVOLVING ANTI-APOPTOTIC GENES AND ANTI-APOPTOTIC GENE PRODUCTS

(75) Inventors: Viktor S Goldmakher, Newton, MA (US); Anna Skaletskaya, Milton, MA (US); Laura M Bartle, Arlington, MA (US)

(73) Assignee: Immunogen Inc., Waltham, MA (US)

( * ) Notice: Subject to any disclaimer, the term of this patent is extended or adjusted under 35 U.S.C. 154(b) by 121 days.

(21) Appl. No.: 11/104,506

(22) Filed: Apr. 13, 2005

(65) Prior Publication Data

US 2005/0191696 A1 Sep. 1, 2005

Related U.S. Application Data

(60) Continuation of application No. 10/463,808, filed on Jun. 18, 2003, now abandoned, which is a division of application No. 09/716,504, filed on Nov. 21, 2000, now Pat. No. 6,605,426, which is a continuation-in-part of application No. 09/301,121, filed on Apr. 28, 1999, now abandoned, which is a continuation-in-part of application No. 09/080,265, filed on May 18, 1998, now Pat. No. 6,218,511.

(51) Int. Cl.
*A61K 31/7088* (2006.01)
*A61K 31/7125* (2006.01)
(52) U.S. Cl. ...................... 514/44; 536/23.72; 536/24.5
(58) Field of Classification Search ..................... 435/5, 435/6; 530/350; 424/211.1
See application file for complete search history.

(56) References Cited

U.S. PATENT DOCUMENTS 6,204,251 B1 * 3/2001 Cuthbertson ................. 514/44

OTHER PUBLICATIONS

Cinatl et al., "Modulatory effects of human cytomegalovirus infection on malignant properties of cancer cells," Intervirology. 1996;39(4):259-69.*
Cinatl et al., "Persistent Human Cytomegalovirus Infection Induces Drug Resistance and Alteration of Programmed Cell Death in Human Neuroblastoma Cells," Cancer Research, 58, pp. 367-372 (1998).*
Azad et al., "Antiviral activity of a phosphorothioate oligonucleotide complementary to human cytomegalovirus RNA when used in combination with antiviral nucleoside analogs," Antiviral Res. Oct. 1995;28(2):101-11.*
Crooke, "Antisense therapeutics," Biotechnol Genet Eng Rev. 1998;15:121-57.*
Mulamba et al., "Human Cytomegalovirus Mutant with Sequence-Dependent Resistance to the Phosphorothioate Oligonucleotide Fomivirsen (ISIS 2922)," Antimicrobial Agents and Chemotherapy, vol. 42, No. 4, pp. 971-973 (1998).*
Leeds et al., "Pharmacokinetics of a Potential Human Cytomegalovirus Therapeutic, A Phosphorothioate Oligonucleotide, After Intravitreal Injection in the Rabbit," Drug Metabolism and Disposition, vol. 25, No. 8, pp. 921-926 (1997).*
Schleiss et al., "Progress toward an elusive goal: current status of cytomegalovirus vaccines," Expert. Rev. Vaccines 4(3), 381-406 (2005).*
Temsamani et al. "Antisense approach for the treatment of cytomegalovirus infection." Expert Opinion on Investigational Drugs 6(6): 1157-1167, 1997.*
Kronenwett et al. "Antisense strategies for the treatment of hematological malignancies and solid tumors." Ann. Hematol. 77: 1-12, 1998.*
Cinatl et al. "Modulatory effects of human cytomegalovirus infection on malignant properties of cancer cells." intervirology 39(4): 259-269, 1996.*
Pari et al, *Antimicrobial Agents and Chemotherapy*, 39(5):1157-1161 (1995).
Smith et al, *J. of Virology*, 69(3):1925-1931 (1995).

* cited by examiner

*Primary Examiner*—Mary E Mosher
(74) *Attorney, Agent, or Firm*—Sughrue Mion, PLLC

(57) ABSTRACT

Novel polypeptides having anti-apoptotic activity, and methods of screening for such novel polypeptides having anti-apoptotic activity, and polynucleotides encoding such polypeptides; Compounds that regulate or modulate apoptosis and/or anti-apoptotic activity, such as compounds having anti-apoptotic activity, and such as compounds that induce, restore, or modulate apoptosis and/or inhibit, diminish, or modulate anti-apoptotic activity, methods of screening for such compounds, and methods of using such compounds in the therapeutic treatment of diseases; Methods of treating eukaryotic cells with compounds that regulate or modulate apoptosis and/or anti-apoptotic activity; Methods of enhancing the stability, growth, and/or productivity of eukaryotic cells; Pharmaceutical compositions that regulate or modulate apoptosis and/or anti-apoptotic activity.

19 Claims, 21 Drawing Sheets

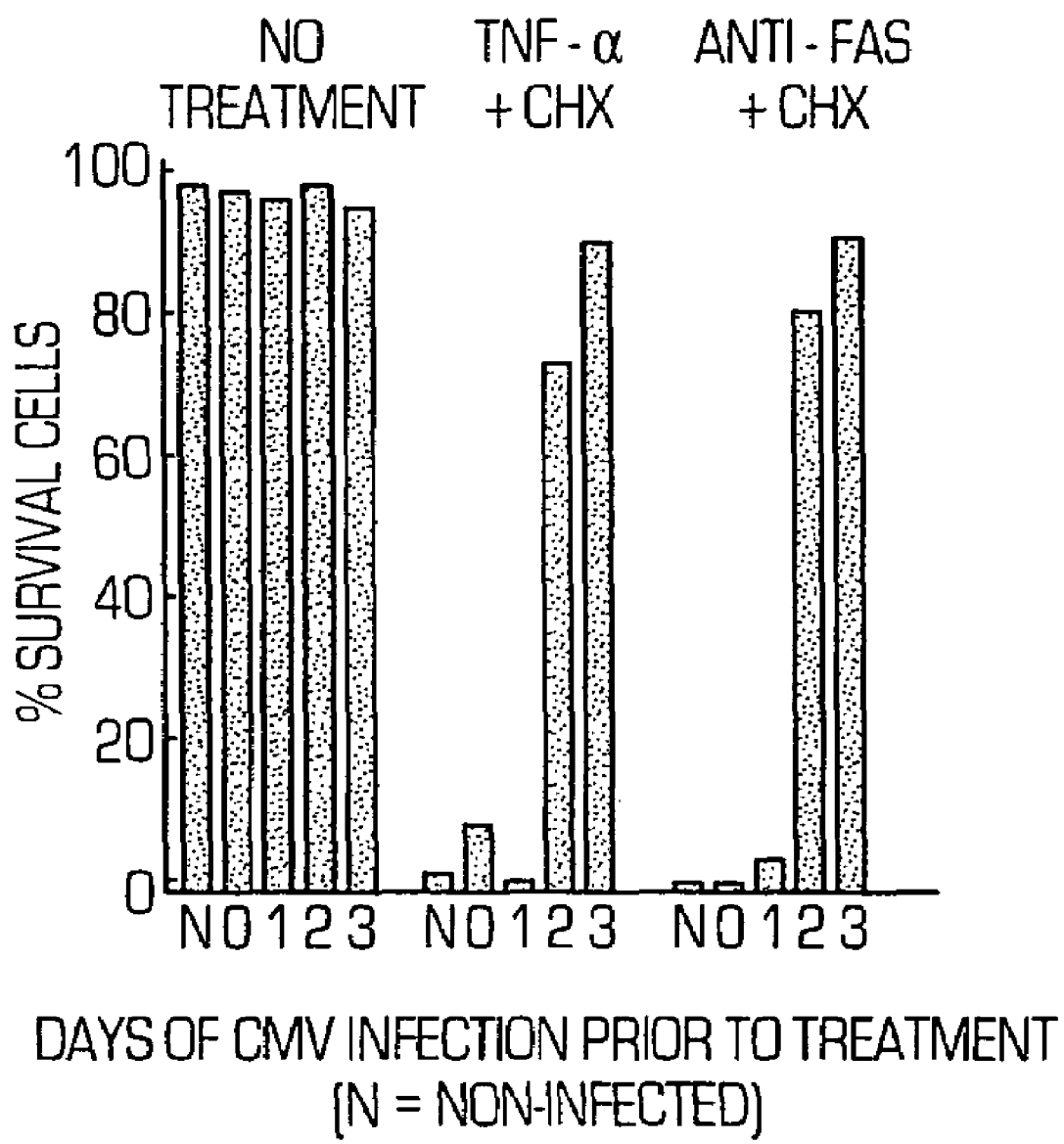

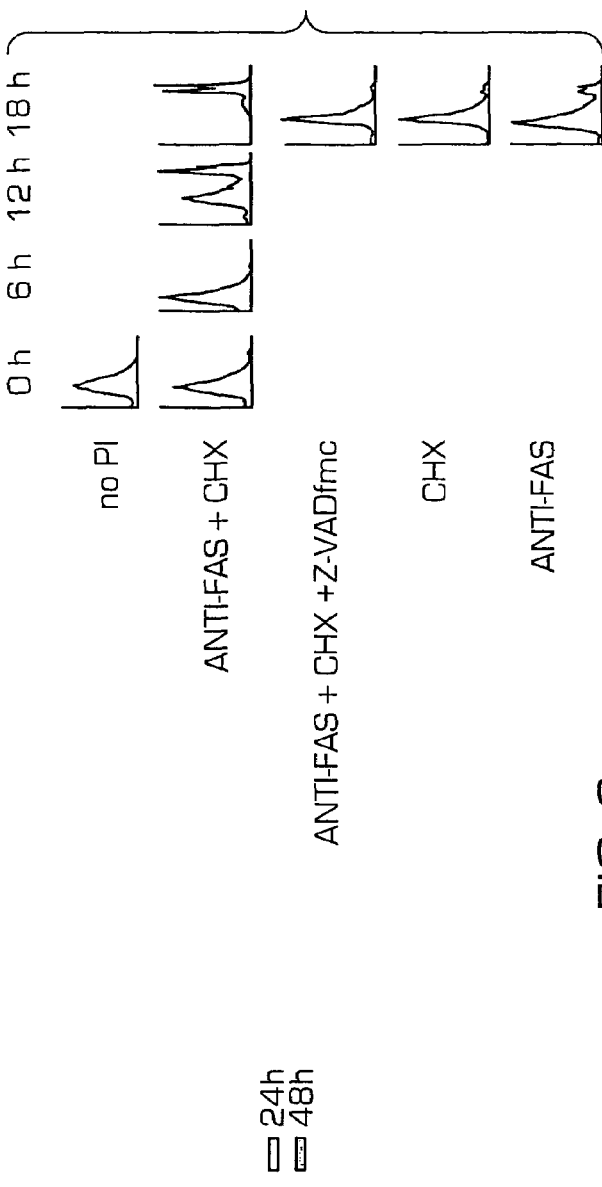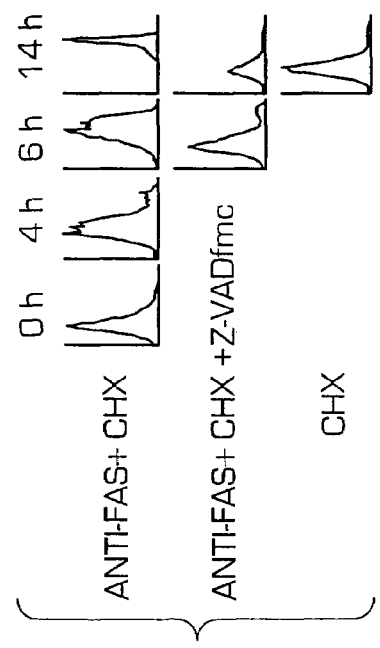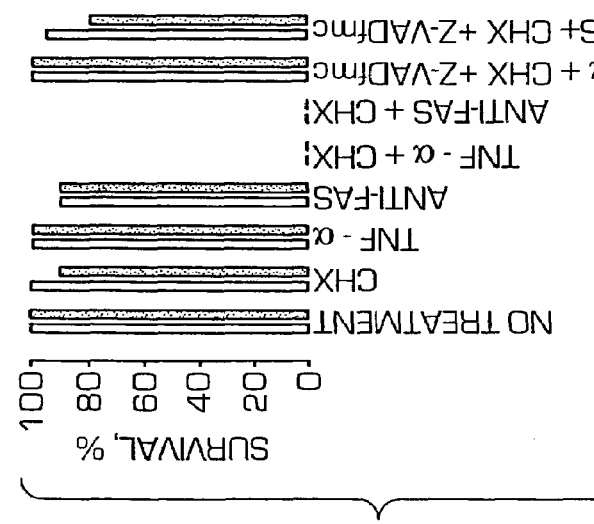

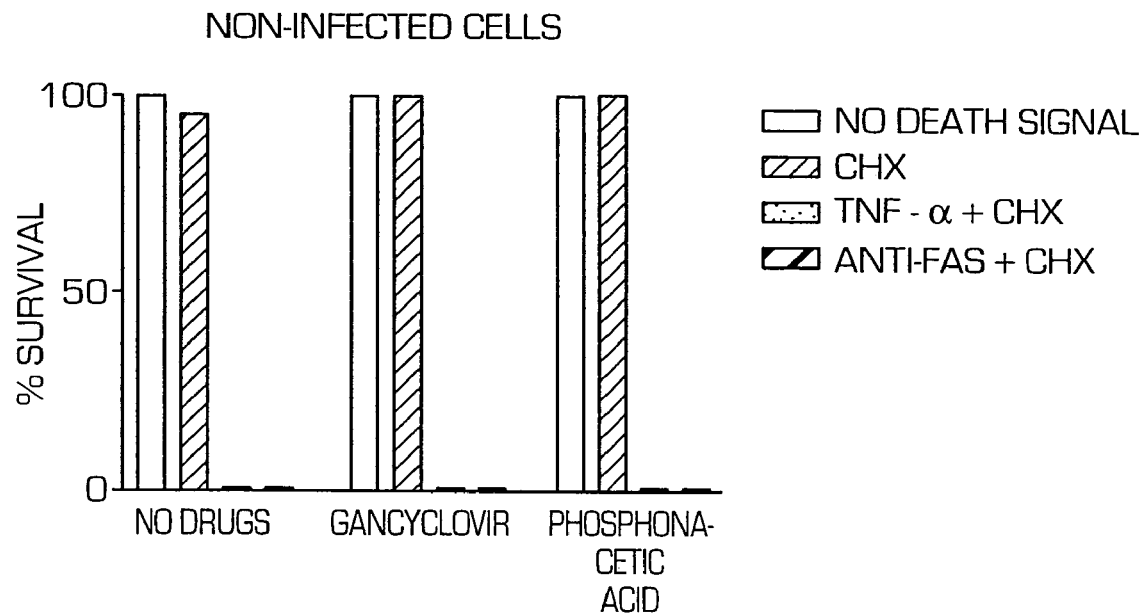
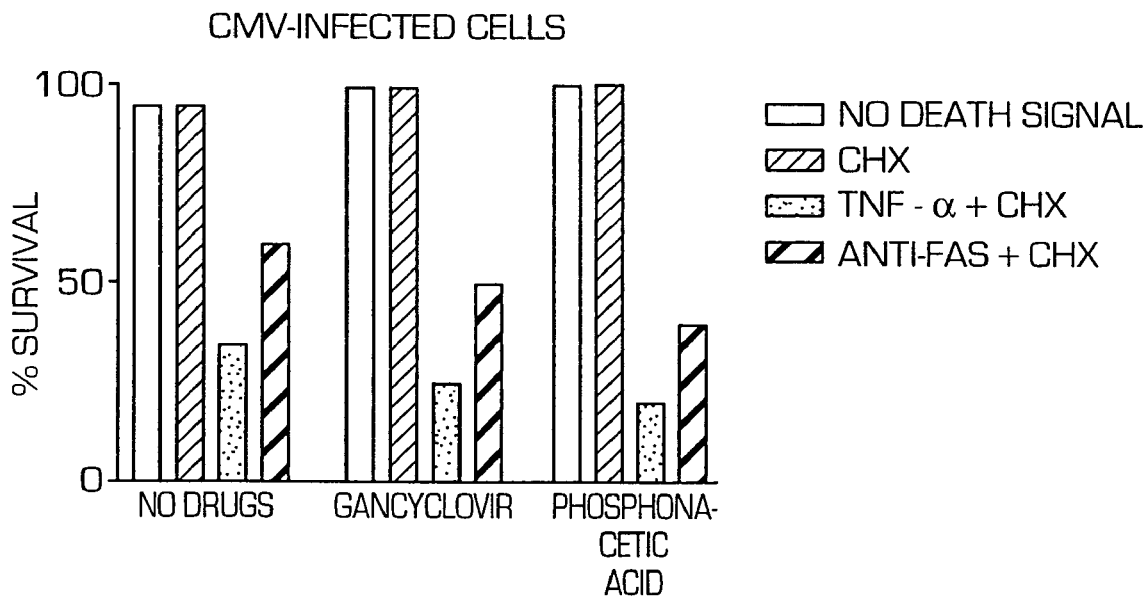

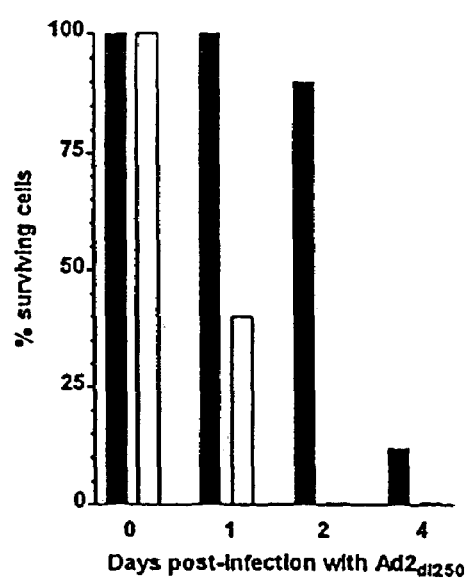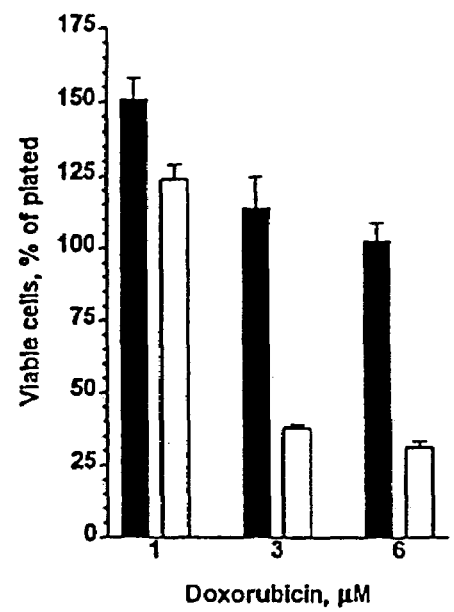

FIG. 13

```
                 40                                                           80
pUL36 CONSENSUS  MDDLRDTLMAYGCIAIRAGDFNGLNDFLEQECGTRLHVAWPERCFIQLRSRSALGPFVGKMGTVCSQGAYVCCQEYLHPF
AD169-EARLY     ----------------------------------------------------------------------------
AD169-ATCC      ----------------------------------------------------------------------------
TOWNE           ----------------------------------------------------------------------------
TOWNE-RIT       ----------------------------------------------------------------------------
TOLEDO          ----------------------------------------------------------------------------

120        131                                              160
pUL36 CONSENSUS  GFVEGPGFMRYQLIVLIGQRGGIYCYDDLRDCVYELAPTMKDFLRHGFRHCDHFHTMRDYQRPMVQYDYWNAVMLYRGD
AD169-EARLY     --------------------------------------------N-----------------------------
AD169-ATCC      --------------------------------------------N---R------------------------
TOWNE           ----------------------------------------A---------------------------------
TOWNE-RIT       ----------------------------------------A---------------------------------
TOLEDO          ----------------------------------------------------------------TTCGP 200                                              240
pUL36 CONSENSUS  VESLSAEVTKRGYASYTIDDPFDECPDTHFAFWTHNTEVMKFKETSFSVVRAGGSIQTMELMIRTVPRITCYHQLLGALG
AD169-EARLY     ----------------V--------------------------------------------------------
AD169-ATCC      -----------------------------------------------------------------------
TOWNE           ----------S------------------------------------------------------------
TOWNE-RIT       WCSTTTTGTPSCY----------------------------------------------------------
TOLEDO          -----------------------------------I-----------------------------------

280                                              320
pUL36 CONSENSUS  HEVPERKEFLVRQYVLVDTFGVVGYDPAMDAVYRLAEDVMFTCVMGKKGHRNHRFSGRREAIVRLEKTPTCQHPKKTP
AD169-EARLY     ----------------------------------------------S-------------------------
AD169-ATCC      ----------------------------------------------S-------------------------
TOWNE           ----------------------------------------------------------------------
TOWNE-RIT       ----------------------------------------------------------------------
TOLEDO          ----------------------------------------------------------------------

360                                              400
pUL36 CONSENSUS  DPMIMFDEDDDELSLPRNVMTHEEAESRLYDAITENLMHCVKLVTTDSPLATHLWPQELQALCDSPALSLCTDDVEGVR
AD169-EARLY     ----------------------------------------------------------------------
AD169-ATCC      ----------------------------------------------------------------------
TOWNE           ----------------------------------------------------------------------
TOWNE-RIT       ----------------------------------------------------------------------
TOLEDO          ----------------------------------------------------------------------

440                                     476
pUL36 CONSENSUS  QKLRARTGSLHHFELSYRFHDEDPETYMGFLWDIPSCDRCVRRRRFKVCDVGRRHIIPGAANGMPPLTPPHAYMNN
AD169-EARLY     ----------------L-----------------------------------------------V--
AD169-ATCC      ----------------L-----------------------------------------------V--
TOWNE           ----------------------------------------A--------------------------
TOWNE-RIT       ----------------------------------------A--------------------------
TOLEDO          -------------------------------------------------------------------
```

HeLa/pcDNA3-A

HeLa/UL37$_S$#3

Hours post-infection

SEQUENCE LISTING

<160> NUMBER OF SEQ ID NOS: 1

<210> SEQ ID NO 1
<211> LENGTH: 476
<212> TYPE: PRT
<213> ORGANISM: Artificial Sequence
<220> FEATURE:

<223> OTHER INFORMATION: Description of Artificial Sequence: consensus
      sequence of HCMV protein pUL36

<400> SEQUENCE: 1

```
Met Asp Asp Leu Arg Asp Thr Leu Met Ala Tyr Gly Cys Ile Ala Ile
  1               5                  10                  15

Arg Ala Gly Asp Phe Asn Gly Leu Asn Asp Phe Leu Glu Gln Glu Cys
             20                  25                  30

Gly Thr Arg Leu His Val Ala Trp Pro Glu Arg Cys Phe Ile Gln Leu
         35                  40                  45

Arg Ser Arg Ser Ala Leu Gly Pro Phe Val Gly Lys Met Gly Thr Val
 50                  55                  60

Cys Ser Gln Gly Ala Tyr Val Cys Cys Gln Glu Tyr Leu His Pro Phe
 65                  70                  75                  80

Gly Phe Val Glu Gly Pro Gly Phe Met Arg Tyr Gln Leu Ile Val Leu
                 85                  90                  95

Ile Gly Gln Arg Gly Gly Ile Tyr Cys Tyr Asp Asp Leu Arg Asp Cys
            100                 105                 110

Val Tyr Glu Leu Ala Pro Thr Met Lys Asp Phe Leu Arg His Gly Phe
        115                 120                 125

Arg His Cys Asp His Phe His Thr Met Arg Asp Tyr Gln Arg Pro Met
    130                 135                 140

Val Gln Tyr Asp Asp Tyr Trp Asn Ala Val Met Leu Tyr Arg Gly Asp
145                 150                 155                 160

Val Glu Ser Leu Ser Ala Glu Val Thr Lys Arg Gly Tyr Ala Ser Tyr
                165                 170                 175

Thr Ile Asp Asp Pro Phe Asp Glu Cys Pro Asp Thr His Phe Ala Phe
            180                 185                 190

Trp Thr His Asn Thr Glu Val Met Lys Phe Lys Glu Thr Ser Phe Ser
        195                 200                 205

Val Val Arg Ala Gly Gly Ser Ile Gln Thr Met Glu Leu Met Ile Arg
    210                 215                 220

Thr Val Pro Arg Ile Thr Cys Tyr His Gln Leu Leu Gly Ala Leu Gly
225                 230                 235                 240

His Glu Val Pro Glu Arg Lys Glu Phe Leu Val Arg Gln Tyr Val Leu
                245                 250                 255

Val Asp Thr Phe Gly Val Val Tyr Gly Tyr Asp Pro Ala Met Asp Ala
            260                 265                 270

Val Tyr Arg Leu Ala Glu Asp Val Val Met Phe Thr Cys Val Met Gly
        275                 280                 285

Lys Lys Gly His Arg Asn His Arg Phe Ser Gly Arg Arg Glu Ala Ile
    290                 295                 300

Val Arg Leu Glu Lys Thr Pro Thr Cys Gln His Pro Lys Lys Thr Pro
305                 310                 315                 320

Asp Pro Met Ile Met Phe Asp Glu Asp Asp Glu Leu Ser Leu
                325                 330                 335

Pro Arg Asn Val Met Thr His Glu Glu Ala Glu Ser Arg Leu Tyr Asp
            340                 345                 350

Ala Ile Thr Glu Asn Leu Met His Cys Val Lys Leu Val Thr Thr Asp
        355                 360                 365

Ser Pro Leu Ala Thr His Leu Trp Pro Gln Glu Leu Gln Ala Leu Cys
    370                 375                 380

Asp Ser Pro Ala Leu Ser Leu Cys Thr Asp Asp Val Glu Gly Val Arg
385                 390                 395                 400
```

```
Gln Lys Leu Arg Ala Arg Thr Gly Ser Leu His His Phe Glu Leu Ser
            405                 410                 415

Tyr Arg Phe His Asp Glu Asp Pro Glu Thr Tyr Met Gly Phe Leu Trp
            420                 425                 430

Asp Ile Pro Ser Cys Asp Arg Cys Val Arg Arg Arg Phe Lys Val
            435                 440                 445

Cys Asp Val Gly Arg Arg His Ile Ile Pro Gly Ala Ala Asn Gly Met
            450                 455                 460

Pro Pro Leu Thr Pro Pro His Ala Tyr Met Asn Asn
465                 470                 475
```

COMPOUNDS, METHODS OF SCREENING, AND IN VITRO AND IN VIVO USES INVOLVING ANTI-APOPTOTIC GENES AND ANTI-APOPTOTIC GENE PRODUCTS

The instant application is a Continuation Application of U.S. application Ser. No. 10/463,808 (Conf. No. 9266) filed Jun. 18, 2003, now abandoned, which is a Divisional Application of U.S. application Ser. No. 09/716,504, filed Nov. 21, 2000, issued as U.S. Pat. No. 6,605,426, which is a Continuation-In-Part Application of U.S. application Ser. No. 09/301,121, filed Apr. 28, 1999, now abandoned, which is a Continuation-In-Part Application of U.S. application Ser. No. 09/080,265, filed May 18, 1998, issued as U.S. Pat. No. 6,218,511, each of which is incorporated herein by reference.

FIELD OF THE INVENTION

The present invention relates generally to the field of cell physiology, and more particularly, to apoptosis. More specifically, the present invention relates to methods for detecting the anti-apoptotic activity and function of viral polypeptides and their interactions with cellular polypeptides. The present invention further relates to viral polypeptides having anti-apoptotic activity and also the mechanism by which such viral polypeptides function to regulate or modulate apoptosis or cell death. Moreover, the present invention relates to compounds that regulate or modulate the anti-apoptotic activity of viral polypeptides, and expression of polynucleotides encoding such polypeptides. Such regulation or modulation of anti-apoptotic activity can lead to the restoration or induction of apoptosis in virally-infected cells and, consequently, inhibit or diminish viral replication.

The present invention relates to novel compounds that regulate or modulate apoptosis and/or anti-apoptotic activity, and uses and methods of screening for such compounds, e.g., 1) novel compounds having anti-apoptotic activity, such as anti-apoptotic polypeptides and the polynucleotides encoding such polypeptides, and in vitro and in vivo uses and methods of screening for such compounds; and 2) novel compounds that inhibit or diminish the anti-apoptotic activity of anti-apoptotic polypeptides and/or expression of polynucleotides encoding such polypeptides, and in vitro and in vivo uses and methods of screening for such compounds; wherein the compounds include diagnostic and/or therapeutic compounds, and wherein the uses include diagnostic and/or therapeutic uses.

The polypeptides, and polynucleotides encoding such polypeptides, comprise viral polypeptides having anti-apoptotic activity, and/or polynucleotides encoding such polypeptides, respectively. Examples of such polypeptides are viral polypeptides of human cytomegalovirus (HCMV) having anti-apoptotic activity, such as pUL36, $pUL37_S$, $pUL37_M$, and $pUL37_L$.

The compounds that regulate or modulate apoptosis and/or anti-apoptotic activity comprise polypeptide, polynucleotide (e.g., DNA and/or RNA), amino acid, nucleotide, and/or chemical compounds, including analogs and/or modified forms of such compounds, and/or synthetic and/or chemical compounds.

BACKGROUND OF THE INVENTION

"Apoptosis" refers to programmed cell death which occurs by an active, physiological process (Kerr, J. F., et al., 1972; Wyllie, A. H., 1980). Cells that die by apoptosis undergo characteristic morphological changes, including cell shrinkage and nuclear condensation and fragmentation. Apoptosis plays an important role in developmental processes, including morphogenesis, maturation of the immune system, and tissue homeostasis whereby cell numbers are limited in tissues that are continually renewed by cell division (Ellis, R. E., et al., 1991; Oppenheim, R. W., et al., 1991; Cohen, J. J., et al., 1992; Raff, M. C. 1992). Moreover, apoptosis is an important cellular safeguard against tumorigenesis (Williams, G. T., 1991; Lane, D. P., 1993). Defects in the apoptotic pathway causing disregulated or aberrant apoptosis may contribute to the onset or progression of malignancies. Under certain conditions, cells undergo apoptosis in response to the forced expression of oncogenes, or other genes that drive cell proliferation (Askew, D., et al., 1991; Evan, G. I., et al., 1992; Rao, L., et al., 1992; Smeyne, R. J., et al., 1993).

A variety of diseases and degenerative disorders may involve aberrant or disregulated apoptosis, resulting in inappropriate or premature cell death or inappropriate cell proliferation (Barr, P. J., et al., 1994). For example, inhibition of cell death may contribute to disease in the immune system by allowing the persistence of self-reactive B and T cells, which consequently promotes autoimmune disease (Watanabe-Fukunaga et al., 1992). Moreover, cancer may result when cells that fail to die undergo further mutations leading to a transformed state of the cells (Korsmeyer, S. J., 1992).

The productive infection by certain viruses may depend on suppression of host cell death by anti-apoptotic viral gene products (Rao, L., et al., 1992; Ray, C. A., et al., 1992; White, E., et al., 1992; Vaux, D. L., et al., 1994), and inhibition of apoptosis can alter the course (i.e., lytic vs. latent) of viral infection (Levine, B., et al., 1993). Moreover, the widespread apoptosis of T lymphocytes triggered by HIV infection may, at least in part, be responsible for the immune system failure associated with AIDS (Gougeon, M., et al., 1993). The roles of apoptosis in normal and pathological cell cycle events are reviewed in Holbrook, N. J. et al., 1996. Importantly, apoptosis comprises an important antiviral defense mechanism in animals and humans by providing the means to rapidly eliminate virally infected cells and restrict viral propagation (O'Brien, 1998; Tschopp et al., 1998). Apoptosis of virally infected cells is triggered by killer cells of the immune system via Fas-ligand interaction with Fas and by granzyme-B-triggered caspase activation (Nagata and Golstein, 1995; Smyth and Trapani, 1998).

To counteract the host defense mechanism, many viruses encode genes that function to inhibit or diminish apoptosis in infected cells (O'Brien, 1998; Tschopp et al., 1998). This inhibition or diminution of apoptosis by viral gene products is achieved by a variety of mechanisms, including: 1) blocking and/or destruction of p53; 2) direct interaction with cellular polypeptides of apoptotic pathways, such as death-effector-domain-containing polypeptides [death-effector-domain motifs are defined in Hu et al., 1997], Bcl-2 family members, and caspases; or 3) by induction of cellular anti-apoptotic polypeptides (Pilder et al., 1984; Gooding et al., 1988; Clem et al., 1991; Hershberger et al., 1992; Brooks et al., 1995; Sedger and McFadden, 1996; Leopardi and Roizman, 1996; Leopardi et al., 1997; Razvi and Welsh, 1995; Teodoro and Branton, 1997; Vaux et al., 1994; Shen and Shenk, 1995; Duke et al., 1996; Vaux and Strasser, 1996; Thompson, 1995).

The prevalence and evolutionary conservation of anti-apoptotic viral genes suggests that suppression of apoptosis is a critical component of efficient viral propagation and/or persistence in vivo. In fact, some of the anti-apoptotic genes were found to be essential for the ability of the respective viruses to replicate and propagate. For example, mutants of human adenovirus that lack the expression of the E1B 19 kDa adenoviral analog of Bcl-2 induce massive apoptosis of infected cells (Teodoro and Branton, 1997) which, consequently, leads to reduced viral titers.

Human cytomegalovirus (HCMV) is widespread in human populations, and is of substantial clinical importance principally because of its pathogenicity in developing fetuses and immunocompromised individuals (Huang and Kowalik, 1993; Britt and Alford, 1996). In particular, those immunocompromised individuals undergoing organ and tissue transplants, or that have malignancies and are receiving immunosuppressive chemotherapy, or that have AIDS, are at greatest risk of HCMV-induced diseases. These diseases range from developmental abnormalities, mental retardation, deafness, mononucleosis, and chorioretinitis, to fatal diseases like interstitial pneumonitis and disseminated HCMV infections (Huang and Kowalik, 1993; Britt and Alford, 1996).

Human cytomegalovirus (HCMV) is a herpesvirus (Roizman, 1991). A number of herpesviruses were shown to induce an apoptotic host cell response, and to suppress this virus-induced apoptosis in the infected cells (Leopardi and Roizman, 1996; Leopardi et al., 1997; Bertin et al., 1997; Sieg et al., 1996). The genomes of several herpesviruses code for a variety of anti-apoptotic polypeptides such as: 1) Bcl-2 homologs, e.g., BHRF-1 of Epstein-Barr virus (Henderson et al., 1993), vbcl-2 of Kaposi's sarcoma-associated herpesvirus (Sarid et al., 1997), and ORF16 of herpesvirus Saimiri (Nava et al., 1997); 2) a polypeptide that induces several cellular anti-apoptotic genes, e.g., LMP-1 of Epstein-Barr virus (Henderson et al., 1991; Wang et al., 1996; Fries et al., 1996); 3) a polypeptide interacting with FLICE (also called caspase 8), e.g., Equine herpesvirus type 2 polypeptide E8 (Bertin et al., 1997; Hu et al., 1997); and 4) two polypeptides with anti-apoptotic properties with a yet poorly characterized mechanism, ICP4 and $U_S3$ of HSV-1 (Leopardi and Roizman, 1996; Leopardi et al., 1997).

While there are several examples of anti-apoptotic genes encoded by other herpesviruses (Tschopp et al., 1998), little is known about the role of apoptosis in HCMV infections. It has been observed that HCMV-infected human cells acquire resistance towards apoptosis induced by serum withdrawal (Kovacs et al., 1996), and by infection of a mutant adenovirus which lacks the expression of the anti-apoptotic polypeptide E1B 19K (Zhu et al., 1995). Two immediate early polypeptides of HCMV, IE1 and IE2, were reported to each exhibit anti-apoptotic activity in some settings (Zhu et al., 1995). However, these viral polypeptides did not suppress apoptosis in other assays (see below).

The HCMV genome (AD169 strain) has been completely sequenced (Chee et al. 1990; Mocarski, 1996). The 230 kb HCMV genome is predicted to encode over 200 polypeptides, many of which have undefined functions (Chee et al., 1990; Mocarski et al., 1996), and none of which bears overt homology to known classes of cell death suppressors (e.g., the Bcl-2 family). Whether most of the HCMV genes are expressed and have any functional importance for HCMV replication remains unknown. In fact, a number of the predicted ORFs were found to be dispensable for the replication and/or propagation of HCMV in cultured cells (Mocarski, 1996).

Aside from IE1 and IE2, no other HCMV anti-apoptotic genes have been identified, and no homology to any of the known anti-apoptotic polypeptides has been found in the HCMV genome. Prior to the discoveries embodied herein, little was known about the UL36 and UL37 genes of HCMV. On the basis of DNA sequence analysis and RNA transcription studies, it was predicted that UL36 has two exons which encode a polypeptide product pUL36, and that UL37 encodes two polypeptide products; $pUL37_S$ encoded by the first exon (also called pUL37x1, see Tenney and Colberg-Poley, 1991 a), and $pUL37_L$ (also called gpUL37, see Zhang et al., 1996) encoded by all three exons (Chee et al., 1990; Tenney and Colberg-Poley, 1991a, b). The expression of $pUL37_L$ in HCMV-infected cells has been detected. However, prior to the discoveries embodied herein, it was not clear whether the hypothetical polypeptide $pUL37_S$ was expressed in HCMV-infected cells. Moreover, $pUL37_M$ had not yet been discovered.

Today, there are only very limited treatment options available for cytomegalovirus infections, and treatment is often associated with high toxicity and the generation of drug resistance (Hirsch, 1994; White and Fenner, 1994; Lalezari et al., 1997). Several potential drug targets for herpesviruses have recently been identified (White and Fenner, 1994, page 267, Table 16.1). Most of the antiviral compounds thus far developed, function to prevent or inhibit viral replication. For example, the currently available antiviral compounds, Gancyclovir, Foscarnet (PFA, phosphonoformic acid) and Cidofovir all act as inhibitors of viral DNA polymerase. There are no available antiviral compounds that function to inhibit or diminish viral infection or to eliminate virally infected cells by regulating or modulating the anti-apoptotic activity of viral polypeptides and/or the expression of viral genes or polynucleotides encoding polypeptides having anti-apoptotic activity, and thereby inducing or restoring apoptosis in virally infected cells.

SUMMARY OF THE INVENTION

The present invention relates to the discovery of methods for detecting the anti-apoptotic function of viral polypeptides and their interactions with cellular polypeptides. The present invention further relates to the discovery of several viral polypeptides having anti-apoptotic activity and also the mechanism by which such viral polypeptides function to regulate or modulate apoptosis and cell death. Moreover, the present invention relates to the discovery of compounds that regulate or modulate the anti-apoptotic activity of viral polypeptides and expression of polynucleotides encoding such polypeptides. Such regulation or modulation of anti-apoptotic activity can lead to the restoration or induction of apoptosis in virally-infected cells and, consequently, inhibit or diminish viral replication.

Thus, these findings provide an approach for the rational design of drugs that regulate or modulate apoptosis and/or anti-apoptotic activity, e.g., by: 1) restoring or inducing anti-apoptotic activity, and thereby inhibiting or diminishing apoptosis; or, alternatively, 2) inhibiting or diminishing anti-apoptotic activity, and thereby restoring or inducing apoptosis.

Accordingly, an object of the present invention is: 1) to provide novel compounds having anti-apoptotic activity, such as anti-apoptotic polypeptides and the polynucleotides encoding such polypeptides, and in vitro and in vivo uses and methods of screening for such compounds; and 2) to provide novel compounds that inhibit or diminish the anti-apoptotic activity of anti-apoptotic polypeptides and polynucleotides encoding such polypeptides, and in vitro and in vivo uses and methods of screening for such compounds; wherein the compounds include diagnostic and/or therapeutic compounds, and wherein the uses include diagnostic and/or therapeutic uses. Such compounds comprise polypeptide (e.g., non-functional forms of anti-apoptotic polypeptides, and monoclonal and/or polyclonal antibodies), polynucleotide (e.g., DNA and/or RNA), amino acid, and/or nucleotide compounds, including analogs and/or modified forms of such compounds.

Additionally, such compounds comprise natural, semi-synthetic, and/or synthetic chemical compounds.

An important embodiment of the present invention is the treatment of diseases, particularly diseases where apoptosis is disregulated or aberrant. The methods of treatment have the potential to change the natural progression of such diseases by regulating or modulating apoptosis and/or anti-apoptotic activity. Depending on the disease, the methods of treatment will: 1) restore or induce anti-apoptotic activity and thereby inhibit or diminish apoptosis; or 2) inhibit or diminish anti-apoptotic activity and thereby restore or induce apoptosis. The invention provides therapeutic compounds and methods of using these compounds to treat such diseases. Accordingly, depending on the disease to be treated, the therapeutic compounds comprise: 1) polypeptides having anti-apoptotic activity and/or polynucleotides encoding such polypeptides; and/or 2) compounds that inhibit or diminish the anti-apoptotic activity of such polypeptides and/or expression of polynucleotides encoding such polypeptides.

An embodiment of the present invention provides methods of screening for and identifying polypeptides having anti-apoptotic activity in cells; and methods of screening for polynucleotides encoding such polypeptides.

In particular, an embodiment of the present invention provides methods of screening for and identifying viral polypeptides such as human cytomegalovirus (HCMV) polypeptides having anti-apoptotic activity in cells; and methods of screening for and identifying polynucleotides encoding such viral polypeptides. Examples of HCMV polypeptides include, polypeptides encoded by UL36, e.g., pUL36 (and/or any unspliced and/or alternatively spliced variants of the polypeptides encoded by UL36), wherein the polynucleotide sequence of UL36 is defined by nucleotides 49,776-48,246 of the HCMV AD169 genome. As reported herein, it is now known that this sequence encodes an inactive form of pUL36. The sequencing of an earlier passage of this strain ($AD169_{early}$) revealed that the active form of pUL36 possesses a cysteine residue at position 131, rather than the arginine identified at this position in pUL36 of AD169.

More particularly, an embodiment of the present invention provides methods of screening for and identifying HCMV polypeptides pUL36, $pUL37_S$, $pUL37_M$, and $pUL37_L$, having anti-apoptotic activity in cells; and methods of screening for and identifying polynucleotides encoding such HCMV polypeptides.

Even more particularly, an embodiment of the present invention provides methods for detecting at least one of HCMV polypeptides pUL36, $pUL37_S$, $pUL37_M$, or $pUL37_L$, using polyclonal and/or monoclonal antibodies that specifically bind to at least one of pUL36 (or any unspliced or alternatively spliced variants of the polypeptides encoded by UL36), $pUL37_S$, $pUL37_M$, or $pUL37_L$.

Another embodiment of the present invention provides methods for detecting the anti-apoptotic activity of polypeptides. In particular, an embodiment of the present invention provides methods of detecting the anti-apoptotic activity of viral polypeptides such as HCMV polypeptides.

Even more particularly, an embodiment of the present invention provides methods of detecting the anti-apoptotic activity of at least one of HCMV polypeptides pUL36, $pUL37_S$, $pUL37_M$, or $pUL37_L$.

Another embodiment of the present invention provides methods of identifying compounds that specifically interact with or bind to at least one of HCMV polypeptides pUL36, $pUL37_S$, $pUL37_M$, or $pUL37_L$ in an in vitro binding assay. Such compounds comprise polypeptide (e.g., monoclonal and/or polyclonal antibodies), polynucleotide (e.g., DNA and/or RNA), amino acid, and/or nucleotide compounds, including analogs and/or modified forms of such compounds. Additionally, such compounds comprise natural, semi-synthetic, and/or synthetic chemical compounds.

In particular, an embodiment of the present invention provides methods of screening for and identifying physiological molecules that specifically bind to at least one of pUL36, $pUL37_S$, $pUL37_M$, or $pUL37_L$, in an in vitro binding assay. Such physiological molecules comprise polypeptide, polynucleotide (e.g., DNA and/or RNA), amino acid, and/or nucleotide compounds. Examples of such physiological molecules are FADD, caspase 3, Apaf-1, $Bcl-x_L$, Bcl-2, Bak, ICE, Bax, BNIP-3, ANT and caspase 8 in its pro- or activated form.

Another embodiment of the present invention provides methods of screening for and identifying compounds that interfere with the specific interaction of a physiological molecule with at least one of pUL36, $pUL37_S$, $pUL37_M$, or $pUL37_L$. Such compounds comprise polypeptide (e.g., non-functional forms of anti-apoptotic polypeptides, and monoclonal and/or polyclonal antibodies), polynucleotide (e.g., DNA and/or RNA), amino acid, and/or nucleotide compounds, including analogs and/or modified forms of such compounds. Additionally, such compounds comprise natural, semi-synthetic, and/or synthetic chemical compounds.

In particular, an embodiment of the present invention provides methods of screening for and identifying compounds that inhibit or diminish the specific binding of a physiological molecule to at least one of pUL36, $pUL37_S$, $pUL37_M$, or $pUL37_L$, in an in vitro binding assay. Such compounds comprise polypeptide (e.g., non-functional forms of anti-apoptotic polypeptides, and monoclonal and/or polyclonal antibodies), polynucleotide (e.g., DNA and/or RNA), amino acid, and/or nucleotide compounds, including analogs and/or modified forms of such compounds. Additionally, such compounds comprise natural, semi-synthetic, and/or synthetic chemical compounds. The physiological molecule comprises polypeptide, polynucleotide (e.g., DNA and/or RNA), amino acid, and/or nucleotide compounds. Examples of such physiological molecules are FADD, caspase 3, Apaf-1, $Bcl-x_L$, Bcl-2, Bak, ICE, Bax, BNIP-3, ANT and caspase 8 in its pro- or activated form.

More particularly, an embodiment of the present invention provides methods of screening for and identifying compounds that inhibit or diminish the specific binding of a physiological molecule to at least one of pUL36, $pUL37_S$, $pUL37_M$, or $pUL37_L$, in an in vitro binding assay, wherein at least one of pUL36, $pUL37_S$, $pUL37_M$, or $pUL37_L$ is immobilized.

Another embodiment of the present invention provides methods of screening for and identifying polypeptides that specifically bind to at least one of pUL36 (or any unspliced or alternatively spliced variants of the polypeptides encoded by UL36), $pUL37_S$, $pUL37_M$, or $pUL37_L$, in a double transformation assay.

Another embodiment of the present invention provides methods of screening for compounds that inhibit or diminish the specific binding of a polypeptide (e.g., FADD, caspase 3, Apaf-1, $Bcl-x_L$, Bcl-2, Bak, ICE, Bax, BNIP-3, ANT and caspase 8 in its pro- or activated form) to at least one of pUL36, $pUL37_S$, $pUL37_M$, or $pUL37_L$, in cells. Such compounds comprise polypeptide (e.g., non-functional forms of anti-apoptotic polypeptides, and monoclonal and/or polyclonal antibodies), polynucleotide (e.g., DNA and/or RNA), amino acid, and/or nucleotide compounds, including analogs and/or modified forms of such compounds. Additionally, such compounds comprise natural, semi-synthetic, and/or synthetic chemical compounds.

In particular, an embodiment of the present invention provides methods of screening for compounds that inhibit or diminish the specific binding of a polypeptide (e.g., FADD, caspase 3, Apaf-1, Bcl-$x_L$, Bcl-2, Bak, ICE, Bax, BNIP-3, ANT and caspase 8 in its pro- or activated form) to at least one of pUL36, pUL37$_S$, pUL37$_M$, or pUL37$_L$, in a double transformation assay.

Another embodiment of the present invention provides methods of screening for compounds that inhibit or diminish anti-apoptotic activity in cells. Such compounds comprise polypeptide (e.g., non-functional forms of anti-apoptotic polypeptides, and monoclonal and/or polyclonal antibodies), polynucleotide (e.g., DNA and/or RNA), amino acid, and/or nucleotide compounds, including analogs and/or modified forms of such compounds. Additionally, such compounds comprise natural, semi-synthetic, and/or synthetic chemical compounds.

In particular, an embodiment of the present invention provides methods of screening for compounds that inhibit or diminish the anti-apoptotic activity of HCMV polypeptides, in cells.

More particularly, an embodiment of the present invention provides methods of screening for compounds that inhibit or diminish the anti-apoptotic activity of at least one of HCMV polypeptides pUL36, pUL37$_S$, pUL37$_M$, or pUL37$_L$, in cells.

Another embodiment of the present invention provides methods of screening for compounds that restore, induce, or modulate apoptotic activity in cells. Such compounds comprise polypeptide (e.g., non-functional forms of anti-apoptotic polypeptides, and monoclonal and/or polyclonal antibodies), polynucleotide (e.g., DNA and/or RNA), amino acid, and/or nucleotide compounds, including analogs and/or modified forms of such compounds. Additionally, such compounds comprise natural, semi-synthetic, and/or synthetic chemical compounds.

In particular, an embodiment of the present invention provides methods of screening for compounds that restore, induce, or modulate apoptosis in cells transformed with a polynucleotide encoding at least one polypeptide having anti-apoptotic activity or at least one fragment of such a HCMV polypeptide.

More particularly, an embodiment of the present invention provides methods of screening for compounds that restore, induce, or modulate apoptosis in cells transformed with a polynucleotide encoding at least one HCMV polypeptide having anti-apoptotic activity or encoding at least one fragment of such a HCMV polypeptide.

Even more particularly, an embodiment of the present invention provides methods of screening for compounds that restore, induce, or modulate apoptosis in cells transformed with a polynucleotide encoding at least one of HCMV polypeptides pUL36, pUL37$_S$, pUL37$_M$, or pUL37$_L$, or at least one fragment of such a HCMV polypeptide.

Another embodiment of the present invention provides methods of screening for compounds that regulate or modulate apoptosis and/or anti-apoptotic activity in cells. Such compounds comprise polypeptide (e.g., non-functional forms of anti-apoptotic polypeptides, and monoclonal and/or polyclonal antibodies), polynucleotide (e.g., DNA and/or RNA), amino acid, and/or nucleotide compounds, including analogs and/or modified forms of such compounds. Additionally, such compounds comprise natural, semi-synthetic, and/or synthetic chemical compounds. Examples of such compounds include modified and/or unmodified DNA and/or RNA antisense oligonucleotides.

Another embodiment of the present invention provides methods of treating cells by contacting the cells with an effective amount of a polypeptide having anti-apoptotic activity, or a polynucleotide encoding such a polypeptide; and thereby inhibiting, diminishing, or modulating apoptotic activity, and/or restoring, inducing, or modulating anti-apoptotic activity. Examples of such polypeptides are viral polypeptides, such as HCMV polypeptides, having anti-apoptotic activity and fragments of such HCMV polypeptides.

More particularly, an embodiment of the present invention provides methods of treating cells by contacting the cells with an effective amount of at least one HCMV polypeptide pUL36, pUL37$_S$, pUL37$_M$, or pUL37$_L$, or at least one fragment thereof, or a homologue of such HCMV polypeptide or fragment thereof; or a polynucleotide encoding at least one of such HCMV polypeptides or encoding at least one fragment thereof, or a homologue of such HCMV polypeptides or fragment thereof; and thereby inhibiting, diminishing, or modulating apoptotic activity, and/or restoring, inducing, or modulating anti-apoptotic activity.

More particularly, an embodiment of the present invention provides methods of treating cells, that are target cells in a patient, by contacting the cells ex vivo with an effective amount of at least one HCMV polypeptide pUL36, pUL37$_S$, pUL37$_M$, or pUL37$_L$, or at least one fragment thereof, or a homologue of such HCMV polypeptide or fragment thereof, or polynucleotide encoding at least one of such HCMV polypeptides or encoding at least one fragment thereof, or a homologue of such HCMV polypeptides or fragment thereof; and thereby inhibiting, diminishing, or modulating apoptotic activity, and/or restoring, inducing, or modulating anti-apoptotic activity. The ex vivo contact of the cells is by, for example, pressure-mediated delivery, gene gun delivery, and/or liposome delivery.

Even more particularly, an embodiment of the present invention provides methods of treating cells, that are target cells in a patient, by contacting the cells ex vivo with an effective amount of a polynucleotide encoding at least one HCMV polypeptide pUL36, pUL37$_S$, pUL37$_M$, or pUL37$_L$, or encoding at least one fragment thereof, or encoding a homologue of such HCMV polypeptide or fragment thereof, wherein the ex vivo contact comprises the transduction of the target cells with a synthetic and/or viral vector carrying the polynucleotide; and thereby inhibiting, diminishing, or modulating apoptotic activity, and/or restoring, inducing, or modulating anti-apoptotic activity. Examples of such synthetic and/or viral vectors for transducing the target cells such as retroviruses, adenovirus, adeno-associated virus, vaccinia virus, herpes simplex virus, avipox virus, and baculovirus.

Another embodiment of the present invention provides methods of treating cells by contacting the cells with an effective amount of a compound that specifically binds to a polypeptide having anti-apoptotic activity or that binds to a polynucleotide encoding such a polypeptide; and thereby inhibiting, diminishing, or modulating anti-apoptotic activity, and/or inducing, restoring, or modulating apoptotic activity. Such compounds comprise polypeptide (e.g., monoclonal and/or polyclonal antibodies), polynucleotide (e.g., DNA and/or RNA), amino acid, and/or nucleotide compounds, including analogs and/or modified forms of such compounds. Additionally, such compounds comprise natural, semi-synthetic, and/or synthetic chemical compounds. Examples of such compounds are synthetic peptides; modified or unmodified DNA or RNA antisense oligonucleotides; and other compounds that selectively bind to viral polypeptides and not to cellular polypeptides. Moreover, the contact of cells is by, for example, pressure-mediated delivery, gene gun delivery, liposome delivery, and/or ex vivo contact.

In particular, an embodiment of the present invention provides methods of treating cells by contacting the cells with an effective amount of a compound that binds to at least one HCMV polypeptide pUL36, pUL37$_S$, pUL37$_M$, or pUL37$_L$, or at least one fragment thereof, or a homologue of such HCMV polypeptide or fragment thereof, or a polynucleotide encoding at least one of such HCMV polypeptides or encoding at least one fragment thereof, or a homologue of such HCMV polypeptides or fragment thereof; and thereby inhibiting, diminishing, or modulating anti-apoptotic activity, and/or inducing, restoring, or modulating apoptotic activity.

In particular, an embodiment of the present invention provides methods of treating cells by contacting the cells with an effective amount of an antisense-oligonucleotide that binds to a polynucleotide encoding at least one HCMV polypeptide pUL36, pUL37$_S$, pUL37$_M$, or pUL37$_L$, or encoding at least one fragment thereof, or encoding a homologue of such HCMV polypeptides or fragment thereof; and thereby inhibiting, diminishing, or modulating anti-apoptotic activity, and/or inducing, restoring, or modulating apoptotic activity.

More particularly, an embodiment of the present invention provides methods of treating cells by contacting the cells with an effective amount of a synthetic anti-sense oligonucleotide that specifically blocks the expression of a polynucleotide encoding a polypeptide having anti-apoptotic activity; and thereby inhibiting, diminishing, or modulating anti-apoptotic activity, and/or inducing, restoring, or modulating apoptotic activity.

Even more particularly, an embodiment of the present invention provides methods of treating cells by contacting the cells with an effective amount of a synthetic anti-sense oligonucleotide having a phosphorothioate backbone that specifically blocks the expression of a polynucleotide encoding at least one HCMV polypeptide pUL36, pUL37$_S$, pUL37$_M$, or pUL37$_L$, or encoding at least one fragment thereof, or encoding a homologue of such HCMV polypeptides or fragment thereof; and thereby inhibiting, diminishing, or modulating anti-apoptotic activity, and/or inducing, restoring, or modulating apoptotic activity.

Also, in particular, an embodiment of the present invention provides methods of treating cells having disregulated or aberrant apoptotic activity (prior to treatment), by contacting the cells with an effective amount of a polypeptide having anti-apoptotic activity, and/or a polynucleotide encoding such a polypeptide; and thereby inhibiting, diminishing, or modulating apoptotic activity, and/or restoring, inducing, or modulating anti-apoptotic activity. Such disregulated or aberrant apoptotic activity may be caused by a degenerative disorder characterized by inappropriate cell death or inappropriate cell proliferation. In particular, the disregulated or aberrant anti-apoptotic activity may be caused by a cancer, immune disorder, autoimmune disease, infectious disease, viral infection, or myocardial infarction or neuronal infarction in cardiovascular disease.

Also, in particular, an embodiment of the present invention provides methods of treating cells having (prior to contact) apoptotic activity potentiated or mediated by a death receptor such as Fas receptor (Fas) or Tumor Necrosis Factor Receptor 1 (TNF-R1), by contacting the cells with an effective amount of a compound that specifically binds to a polypeptide having anti-apoptotic activity or specifically binds to a polynucleotide encoding such a polypeptide; and thereby inhibiting, diminishing, or modulating anti-apoptotic activity, and/or inducing, restoring, or modulating apoptotic activity.

Also, in particular, an embodiment of the present invention provides methods of treating cells by contacting the cells with an effective amount of a compound that specifically binds to a polypeptide having anti-apoptotic activity or specifically binds to a polynucleotide encoding such a polypeptide, wherein said polypeptide inhibits the activation of caspase 9, inhibits the activation of caspase 8, and/or inhibits the release of cytochrome c from mitochondria; and thereby inhibiting, diminishing, or modulating anti-apoptotic activity, and/or inducing, restoring, or modulating apoptotic activity.

Another embodiment of the present invention provides methods of enhancing the stability, growth, and/or productivity of cells by introducing into cells, by, for example, transfection or retrovirus infection, a polynucleotide encoding a polypeptide having anti-apoptotic activity, and expressing the polypeptide in the cells; wherein the cells under normal conditions do not express such a polypeptide. Examples of such cells are hybridomas, Chinese Hamster Ovary (CHO) cells, fibroblasts, lymphoid cells, haematopoietic cells, cells derived from the embryonic central nervous system, and cells derived from normal, dysplastic, or neoplastic tissue.

In particular, an embodiment of the present invention provides methods of enhancing the stability, growth, and/or productivity of cells by introducing into cells, by transfection or retrovirus infection, a polynucleotide encoding at least one HCMV polypeptide pUL36, pUL37$_S$, pUL37$_M$, or pUL37$_L$, or encoding at least one fragment thereof, or encoding a homologue of such HCMV polypeptides or fragment thereof, and expressing the polypeptide in the cells; wherein the cells under normal conditions do not express such a polypeptide.

Another embodiment of the present invention provides pharmaceutical compositions comprising a therapeutically effective amount of a polypeptide having anti-apoptotic activity, or a therapeutically effective amount of a polynucleotide encoding such a polypeptide.

In particular, an embodiment of the present invention provides pharmaceutical compositions comprising a therapeutically effective amount of at least one HCMV polypeptide pUL36, pUL37$_S$, pUL37$_M$, or pUL37$_L$, or at least one fragment thereof, or a homologue of such HCMV polypeptides or fragment thereof; or a polynucleotide encoding at least one of such HCMV polypeptides or encoding at least one fragment thereof, or encoding a homologue of such HCMV polypeptides or fragment thereof. In a preferred embodiment, the fragment of pUL37$_S$ comprises amino acid residues 5-34 and 118-147 of the native pUL37$_S$ protein. In another preferred embodiment, the homologue of pUL37$_S$ comprises amino acid residues 5-34 and 118-147 of the native pUL37$_S$ protein.

Another embodiment of the present invention provides pharmaceutical compositions comprising a therapeutically effective amount of a compound that specifically binds to a polypeptide having anti-apoptotic activity, or that specifically binds to a polynucleotide encoding such a polypeptide. Such compounds comprise polypeptide (e.g., monoclonal and/or polyclonal antibodies), polynucleotide (e.g., DNA and/or RNA), amino acid, and/or nucleotide compounds, including analogs and/or modified forms of such compounds. Additionally, such compounds comprise natural, semi-synthetic, and/or synthetic chemical compounds. An example of such a compound is a synthetic polypeptide that binds to the polypeptide having anti-apoptotic activity, or that binds to a polynucleotide encoding a polypeptide having anti-apoptotic activity. Another example of such a compound is an antisense oligonucleotide having a sequence complimentary to the sequence of the polynucleotide encoding a polypeptide having anti-apoptotic activity, wherein the antisense oligonucleotide may or may not comprise a phosphorothioate backbone.

In particular, an embodiment of the present invention provides pharmaceutical compositions comprising a therapeutically effective amount of a compound that specifically binds to at least one HCMV polypeptide pUL36, pUL37$_S$, pUL37$_M$, or pUL37$_L$, or binds to at least one fragment thereof, or a homologue of such HCMV polypeptides or fragment thereof; or binds to a polynucleotide encoding at least one of such HCMV polypeptides or encoding at least one fragment thereof, or encoding a homologue of such HCMV polypeptides or fragment thereof.

Another embodiment of the present invention provides an isolated or synthetic polypeptide having anti-apoptotic activity in a cell, wherein the polypeptide comprises a viral polypeptide.

In particular, an embodiment of the present invention provides an isolated or synthetic polypeptide having anti-apoptotic activity in cells, wherein the polypeptide comprises a human cytomegalovirus (HCMV) polypeptide other than pUL37$_S$ and UL37$_L$.

More particularly, an embodiment of the present invention provides an isolated or synthetic polypeptide having anti-apoptotic activity in cells, wherein the polypeptide comprises the amino acid sequence of pUL36 or pUL37$_M$.

Also more particularly, an embodiment of the present invention provides an isolated or synthetic polypeptide having anti-apoptotic activity in cells, wherein the polypeptide comprises a fragment of the amino acid sequence of pUL36, pUL37$_S$, pUL37$_M$ or pUL37$_L$. In a preferred embodiment, the fragment of pUL37$_S$ comprises amino acid residues 5-34 and 118-147 of the native pUL37$_S$ protein. Again more particularly, an embodiment of the present invention provides an isolated or synthetic polypeptide having anti-apoptotic activity in cells, wherein the polypeptide comprises a sequence homologous to the amino acid sequence of pUL36, pUL37$_S$, pUL37$_M$, or pUL37$_L$. In another preferred embodiment, the homologue of pUL37$_S$ comprises amino acid residues 5-34 and 118-147 of the native pUL37$_S$ protein.

Also, more particularly, an embodiment of the present invention provides an isolated or synthetic polypeptide having anti-apoptotic activity in cells, wherein the polypeptide comprises a polypeptide encoded by UL36 (or any unspliced or alternatively spliced variants of the polypeptide encoded by UL36); and wherein the nucleotide sequence of UL36 is defined by nucleotides 49,776-48,246 of the HCMV AD169 genome.

In particular, an embodiment of the present invention provides an isolated or synthetic polypeptide having anti-apoptotic activity in cells, wherein the polypeptide is encoded by nucleotides 49,776-48,246 of the HCMV AD169 genome and is pUL36.

Another embodiment of the present invention provides a compound that specifically binds to an isolated or synthetic polypeptide having anti-apoptotic activity in a cell, wherein the polypeptide comprises a viral polypeptide, and wherein the compound inhibits, diminishes, or modulates anti-apoptotic activity and/or restores, induces, or modulates apoptosis. Such compounds comprise polypeptide (e.g., monoclonal and/or polyclonal antibodies), polynucleotide (e.g., DNA and/or RNA), amino acid, and/or nucleotide compounds, including analogs and/or modified forms of such compounds. Additionally, such compounds comprise natural, semi-synthetic, and/or synthetic chemical compounds.

In particular, an embodiment of the present invention provides a compound that specifically binds to an isolated or synthetic polypeptide having anti-apoptotic activity in cells, wherein the polypeptide comprises a human cytomegalovirus (HCMV) polypeptide, and wherein the compound inhibits, diminishes, or modulates anti-apoptotic activity, and/or restores, induces, or modulates apoptosis. Examples of such compounds are monoclonal and/or polyclonal antibody that bind to at least one of pUL36, pUL37$_S$, pUL37$_M$, or pUL37$_L$.

More particularly, an embodiment of the present invention provides a compound that specifically binds to a physiological molecule that is bound by a polypeptide having anti-apoptotic activity in cells, wherein the physiological molecule is FADD, caspase 3, Apaf-1, Bcl-x$_L$, Bcl-2, Bak, ICE, Bax, BNIP-3, ANT and caspase 8 in its pro- or activated form, and the polypeptide comprises the amino acid sequence of pUL36, pUL37$_S$, pUL37$_M$ or pUL37$_L$, or a fragment thereof, or a homologue of the polypeptide or fragment thereof, wherein the compound inhibits, diminishes, or modulates anti-apoptotic activity, and/or restores, induces, or modulates apoptosis.

Also, more particularly, an embodiment of the present invention provides a compound that specifically binds to an isolated or synthetic polypeptide having anti-apoptotic activity in cells wherein the polypeptide comprises a polypeptide encoded by UL36 (or any unspliced or alternatively spliced variants of the polypeptide encoded by UL36); wherein the nucleotide sequence of UL36 is defined by nucleotides 49,776-48,246 of the HCMV AD169 genome; and wherein the compound inhibits, diminishes, or modulates anti-apoptotic activity, and/or restores, induces, or modulates apoptosis.

In particular, an embodiment of the present invention provides a compound that binds specifically to an isolated or synthetic polypeptide having anti-apoptotic activity in cells, wherein the polypeptide is encoded by nucleotides 49,776-48,246 of the HCMV AD 169 genome and is pUL36, and wherein the compound inhibits, diminishes, or modulates anti-apoptotic activity, and/or restores, induces, or modulates apoptosis.

Another embodiment of the present invention provides a first isolated or synthetic polypeptide that specifically binds to a second isolated or synthetic polypeptide having anti-apoptotic activity in cells, and thereby the first polypeptide prevents the second polypeptide from binding to FADD, caspase 3, Apaf-1, Bcl-x$_L$, Bcl-2, Bak, ICE, Bax, BNIP-3, ANT and caspase 8 in its pro- or activated form. Examples of the second polypeptide are HCMV polypeptides having anti-apoptotic activity, such as pUL36, pUL37$_S$, pUL37$_M$, and pUL37$_L$.

In particular, an embodiment of the present invention provides a first isolated or synthetic polypeptide that specifically binds to a second isolated or synthetic polypeptide having anti-apoptotic activity in cells, and thereby the first polypeptide prevents the second polypeptide from binding to FADD, caspase 3, Apaf-1, Bcl-x$_L$, Bcl-2, Bak, ICE, Bax, BNIP-3, ANT and caspase 8 in its pro- or activated form, wherein the second polypeptide comprises a sequence homologous to the amino acid sequence pUL36, pUL37$_S$, pUL37$_M$ or pUL37$_L$.

In particular, an embodiment of the present invention provides a first isolated or synthetic polypeptide that specifically binds to a second isolated or synthetic polypeptide having anti-apoptotic activity in cells, and thereby the first polypeptide prevents the second polypeptide from binding to FADD, caspase 3, Apaf-1, Bcl-x$_L$, Bcl-2, Bak, ICE, Bax, BNIP-3, ANT and caspase 8 in its pro- or activated form, wherein the second polypeptide comprises a polypeptide encoded by UL36 (or any unspliced or alternatively spliced variants of the polypeptide encoded by UL36); and wherein the nucleotide sequence of UL36 is defined by nucleotides 49,776-48,246 of the HCMV AD 169 genome.

Also, in particular, an embodiment of the present invention provides a first isolated or synthetic polypeptide that binds specifically to a second isolated or synthetic polypeptide having anti-apoptotic activity in cells, and thereby the first polypeptide prevents the second polypeptide from binding to FADD, caspase 3, Apaf-1, Bcl-$x_L$, Bcl-2, Bak, ICE, Bax, BNIP-3, ANT and caspase 8 in its pro- or activated form, and wherein the second polypeptide is encoded by nucleotides 49,776-48,246 of the HCMV AD169 genome and is pUL36.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 1 is a histogram showing the percentage of surviving cells at 0, 1, 2, and 3 days post infection with HCMV strain TowneRIT. TowneRIT was obtained from Dr. Stanley Plotkin as vaccine lot 131 from RIT (now SmithKline Beecham Biologics) and plaque-subcloned three times. Cells were infected with 3 plaque forming units/cell or left uninfected (N). Cells at 0, 1, 2, and 3 days post HCMV infection were exposed for an additional 12 h to either medium alone (no treatment), tumor necrosis factor-α (TNF-α)+cycloheximide (CHX), or anti-Fas antibody+CHX, and then the viable cells remaining after treatment were quantified by counting representative fields under a phase microscope.

FIG. 2A is a histogram showing the effects of TNF-α and anti-Fas antibody, alone or in the presence of CHX, or CHX+ the caspase inhibitor Z-VADfmc, on the survival of MRC-5 normal human fibroblasts 24 h and 48 h after treatment, as measured by direct observation and quantitation of cells under a phase microscope.

FIG. 2B is a series of graphs showing the effects of anti-Fas antibody, alone or in the presence of CHX, or CHX+Z-VAD-fmc, on the survival of MRC-5 normal human fibroblasts as measured by direct observation and quantitation of cells by dye exclusion (propidium iodide/PI) assay on a flow cytometer.

FIG. 2C is a series of graphs showing the effects of anti-Fas antibody, in the presence of CHX, or CHX+Z-VADfmc, on the survival of MRC-5 normal human fibroblasts as measured by direct observation and quantitation of cells by measuring Annexin V binding to cells.

FIGS. 3A and 3B are histograms showing the effects of TNF-α and anti-Fas antibody, in the presence of CHX, on the survival of MRC-5 fibroblasts infected with HCMV (FIG. 3B) or empty vector (FIG. 3A), and treated with gancyclovir or phosphonacetic acid, or left untreated ("No drugs").

FIG. 8C is a histogram showing the percentage of surviving HeLa/UL37x1#3 cells (filled bars) and HeLa/pcDNA3-A control cells (open bars), at 0, 1, 2 and 4 days post-infection with Ad2$_{dl250}$ (3 plaque forming units/cell), wherein the surviving cells were counted under a microscope at the indicated times.

FIG. 8D is a histogram showing the number of viable HeLa/UL37x1#3 cells (filled bars) constitutively expressing pUL37$_S$myc, and HeLa/pcDNA3-A control cells (open bars), after exposure to doxorubicin at 1, 3, and 6 μM, wherein the viable cells (as determined by trypan blue exclusion) were counted (+/−SEM, n=2) after the 24 h exposure to doxorubicin.

The right side of the figure shows the results of Example 14. The "Anti-apoptotic activity" of each deletion mutant is indicated as possessing anti-apoptotic activity ("+") or lacking such activity ("−"). The "Mitochondrial localization" of each deletion mutant is indicated as being localized to the mitochondria ("+"), not being localized to the mitochondria "−"), or not being determined ("not done").

FIG. 13 is an alignment of the amino acid sequences of the HCMV polypeptide pUL36, as encoded by five strains of HCMV, beneath a consensus amino acid sequence of a pUL36 polypeptide (SEQ ID NO: 1). Dashes (−) below the consensus sequence indicate invariant amino acids. Letters below the consensus sequence represent variant amino acids. Empty spaces in the Towne-RIT sequence represent a deletion.

Figure 14:
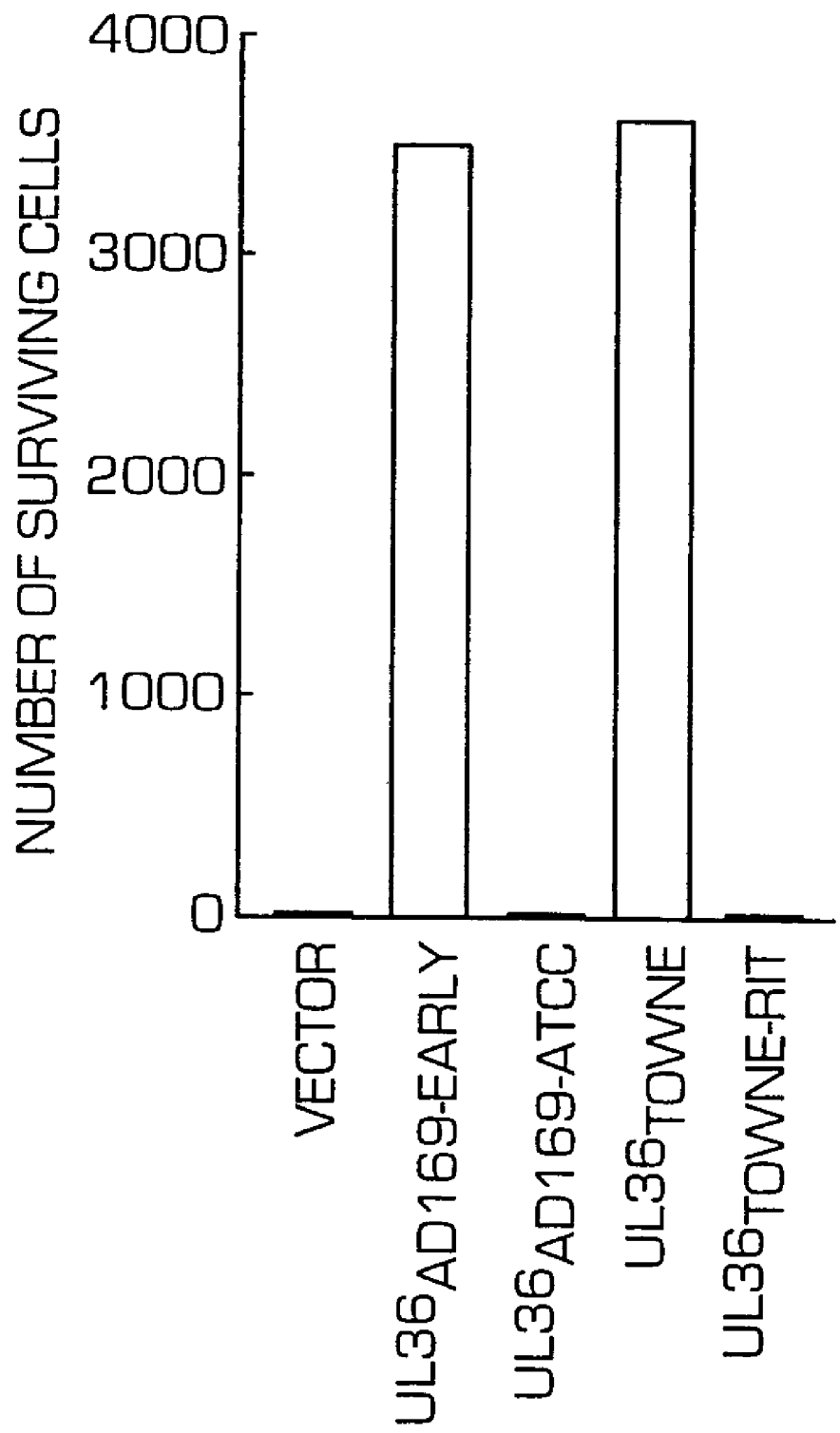

FIG. 14 is a histogram showing the ability of the HCMV polypeptide pUL36, produced by four different HCMV strains, to inhibit anti-Fas+CHX induced apoptosis in HeLa cells. Genomic DNA segments spanning just the UL36 coding regions of HCMV strains AD169-early ("pUL36$_{AD169-early}$"), AD169-ATCC ("pUL36$_{AD169-ATCC}$"), Towne ("pUL36$_{Towne}$"), and Towne$_{Rit}$ ("pUL36$_{Towne-RIT}$") were generated and transfected into an expression vector. Control cells were transfected with empty vector ("vector"). 24 h after transfections cells were treated with anti-Fas+CHX for 24 h, then viewed under a microscope.

Figure 15:
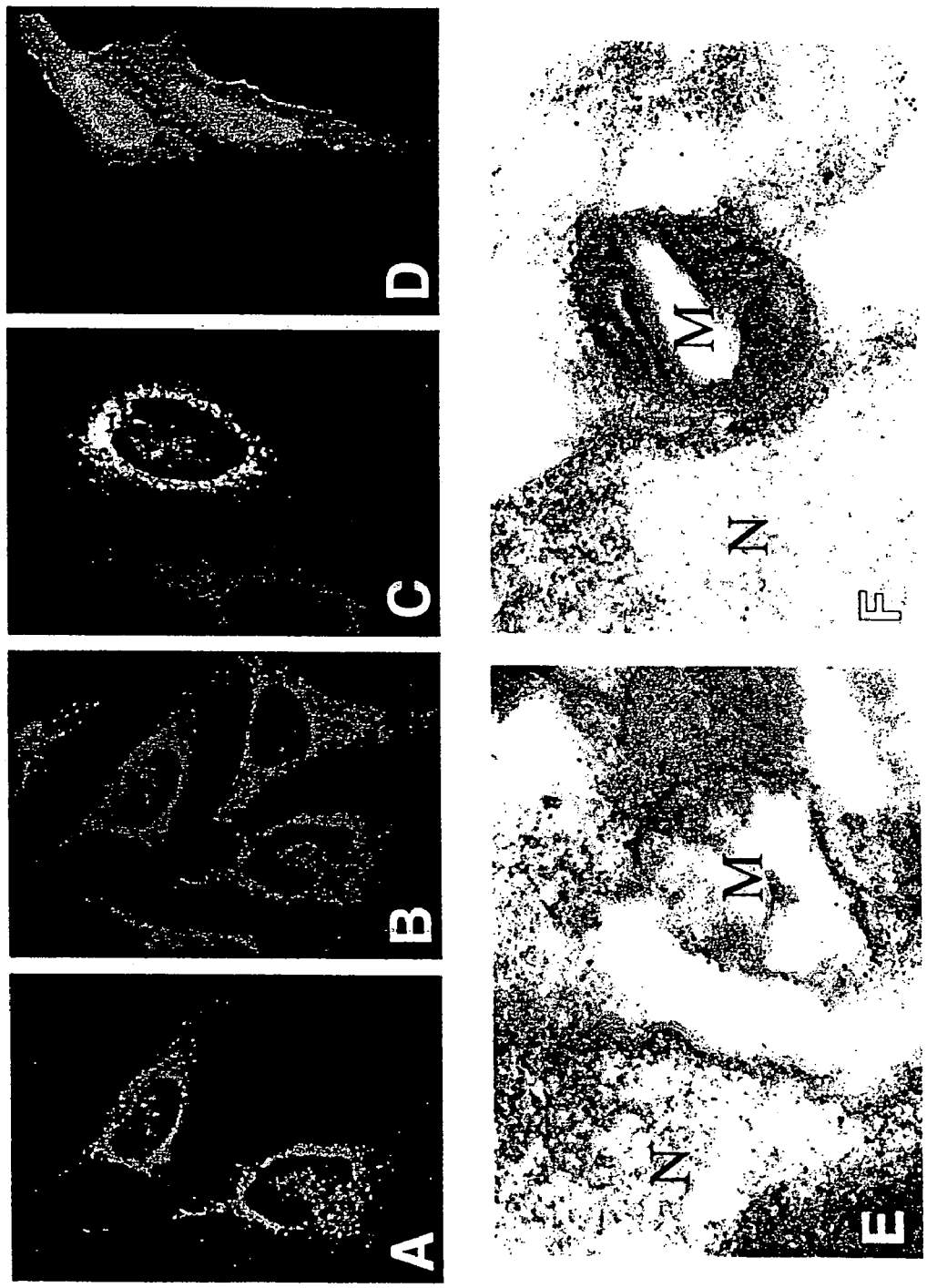

FIGS. 15A-15D are photographs showing HeLa cells transiently transfected with plasmids expressing either pUL37x1myc (FIGS. 15A-15C) or pUL37x1Δ2-23myc (FIG. 15D). The transfected HeLa cells were permeabilized and stained with either 9E10 anti-myc antibody (FIGS. 15A, 15C, and 15D; green fluorescence), or anti-mitochondrial anti-serum (FIGS. 15B and 15C; red fluorescence). Yellow coloring (FIG. 15C) resulted from the superimposition of red and green fluorescence. Control cells transiently transfected with plasmid vector pcDNA3 (empty vector, control) did not stain with the 9E10 anti-myc antibody (not shown).

FIGS. 15E-15F are photographs showing ultra-thin cryo-sections of HeLa/UL37x1myc #3 cells viewed and detected by immunoelectron microscopy, and depicting two representative fields ("M" stands for mitochondria; "N" stands for nuclei). The cryosections were stained first with 9E10 anti-myc antibody and then with secondary antibody-gold conjugates. HeLa/pcDNA3-A control cells stained with the 9E10 anti-myc antibody did not reveal specific mitochondrial labeling (not shown).

Figure 16A:
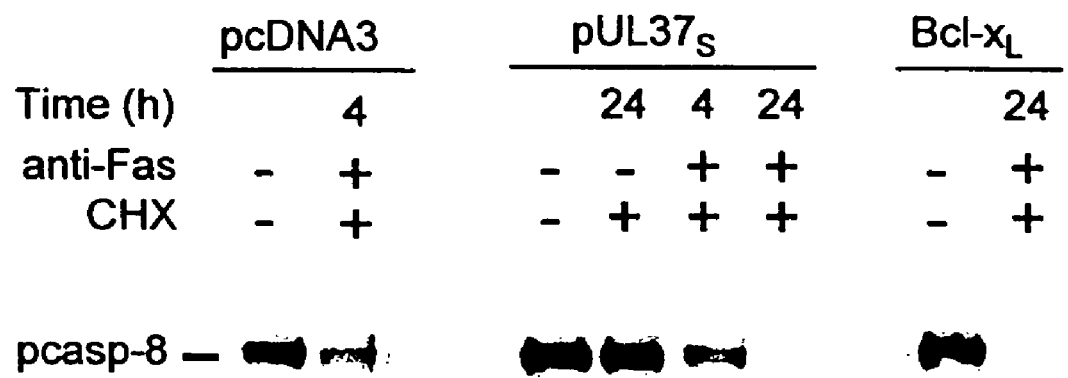

FIG. 16A is a set of photographs showing a Western blot analysis of pro-caspase 8 (55 kDa) expression in HeLa/pcDNA3-A control cells ("pcDNA3"), HeLa/pUL37x1myc cells ("pUL37$_S$"), and HeLa/Bcl-x$_L$ cells ("Bcl-x$_L$"), each treated with CHX ("+"), or anti-Fas antibody ("+"), or both, for 4 or 24 h, or left untreated (−). Lysates of the cells were prepared immediately post-treatment, and pro-caspase 8 was detected by Western blot analysis using 5F7 anti-human caspase 8 antibody ("pcasp-8"; Upstate Biotechnology).

Figure 16B:
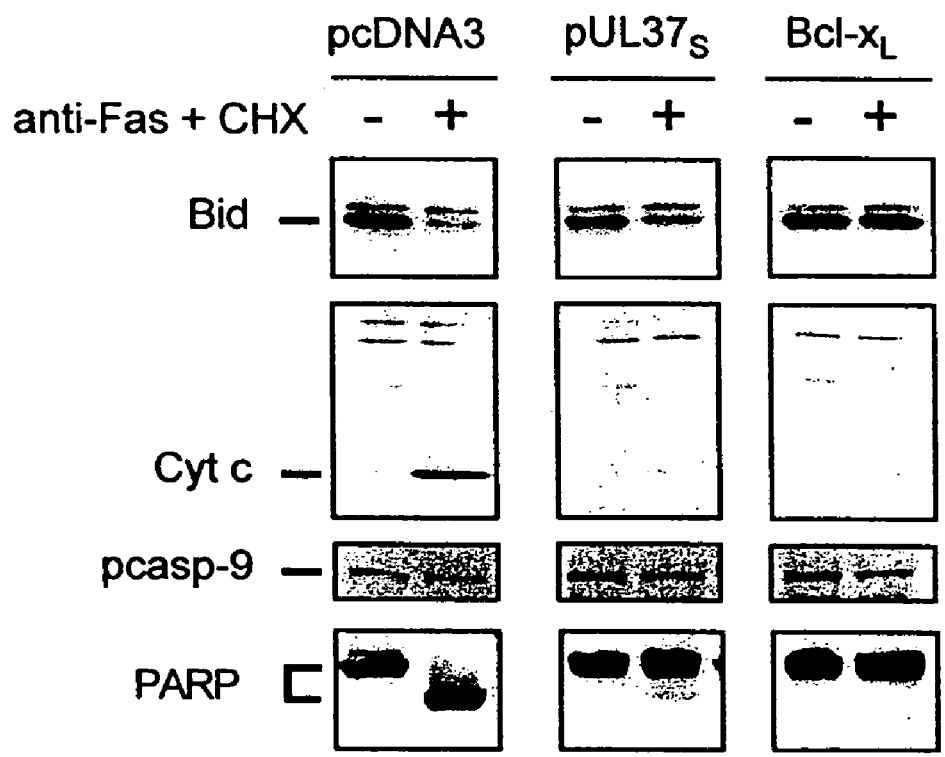

FIG. 16B is a set of photographs showing a Western blot analysis of Bid (12 kDa), cytochrome c (15 kDa) procaspase 9 (48 kDa) and PARP expression in HeLa/pcDNA3-A control cells ("pcDNA3"), HeLa/UL37x1#3 cells ("pUL37$_S$"), and HeLa/Bcl-x$_L$ cells ("Bcl-x$_L$"), treated (+) with anti-Fas antibody+CHX for 4 h, or left untreated (−). S100 extracts of the cells were prepared immediately post-treatment, and Bid, cytochrome c ("Cyt c"), pro-caspase 9 ("pcasp-9"), and PARP were detected by Western blot analysis.

The anti-Bid antibody (C-20 antibody, Santa Cruz Biotechnology) detected a 25 kDa polypeptide corresponding to non-proteolyzed Bid. The anti-PARP antibody detected both intact PARP (116 kDa) and an 85 kDa PARP fragment.

Figure 17:
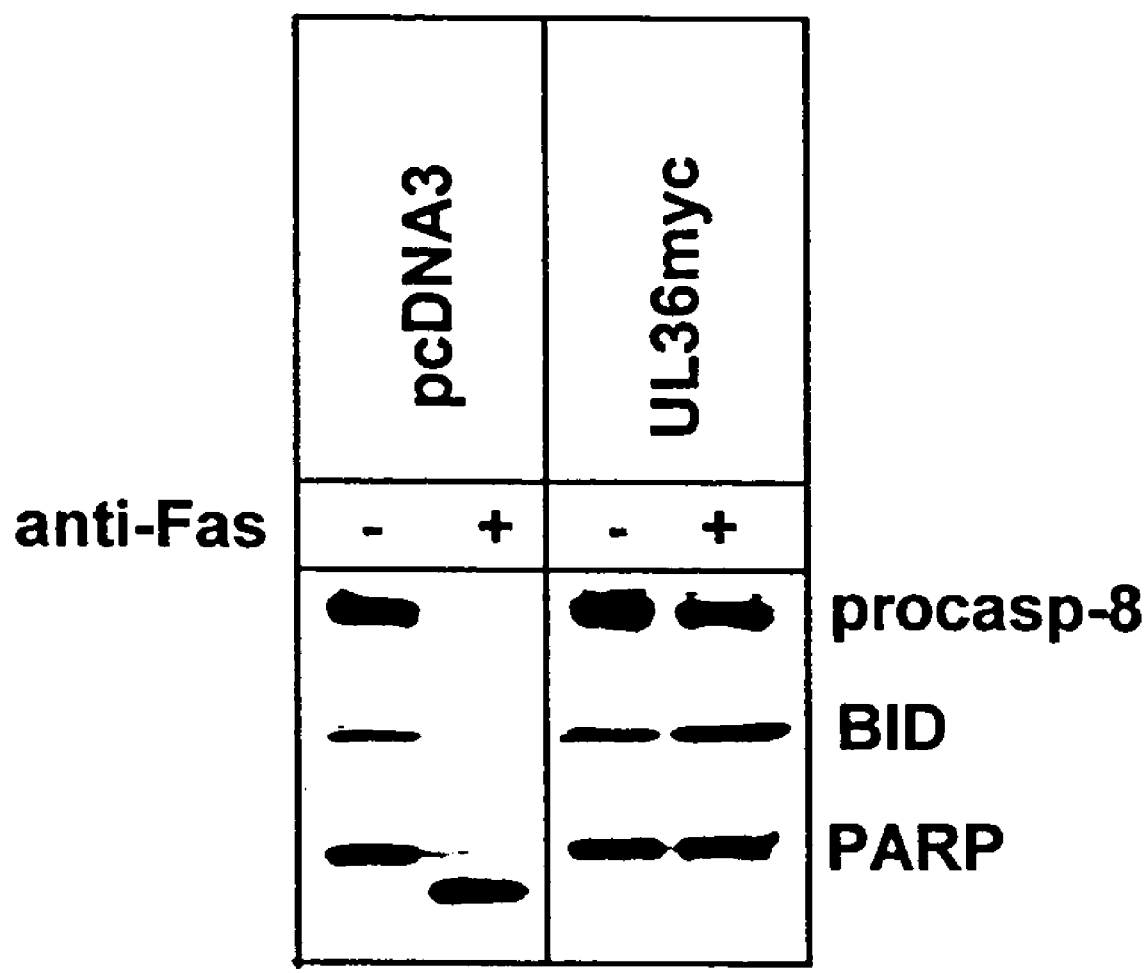

FIG. 17 is a photograph of a Western blot analysis of the effect of pUL36 expression on elements of the Fas-induced apoptotic signaling pathway. HeLa cells were transfected with either empty vector ("pcDNA3," lanes 1 and 2) or UL36myc (lanes 3 and 4). The cells were treated with anti-Fas antibodies for 24 h (lanes 2 and 4), or left untreated (lanes 1 and 3). Cell lysates were prepared, separated by SDS-PAGE and blotted onto nitrocellulose. Pro-caspase 8 ("pcasp-8"), Bid and PARP were then detected by Western analysis.

Figure 18:
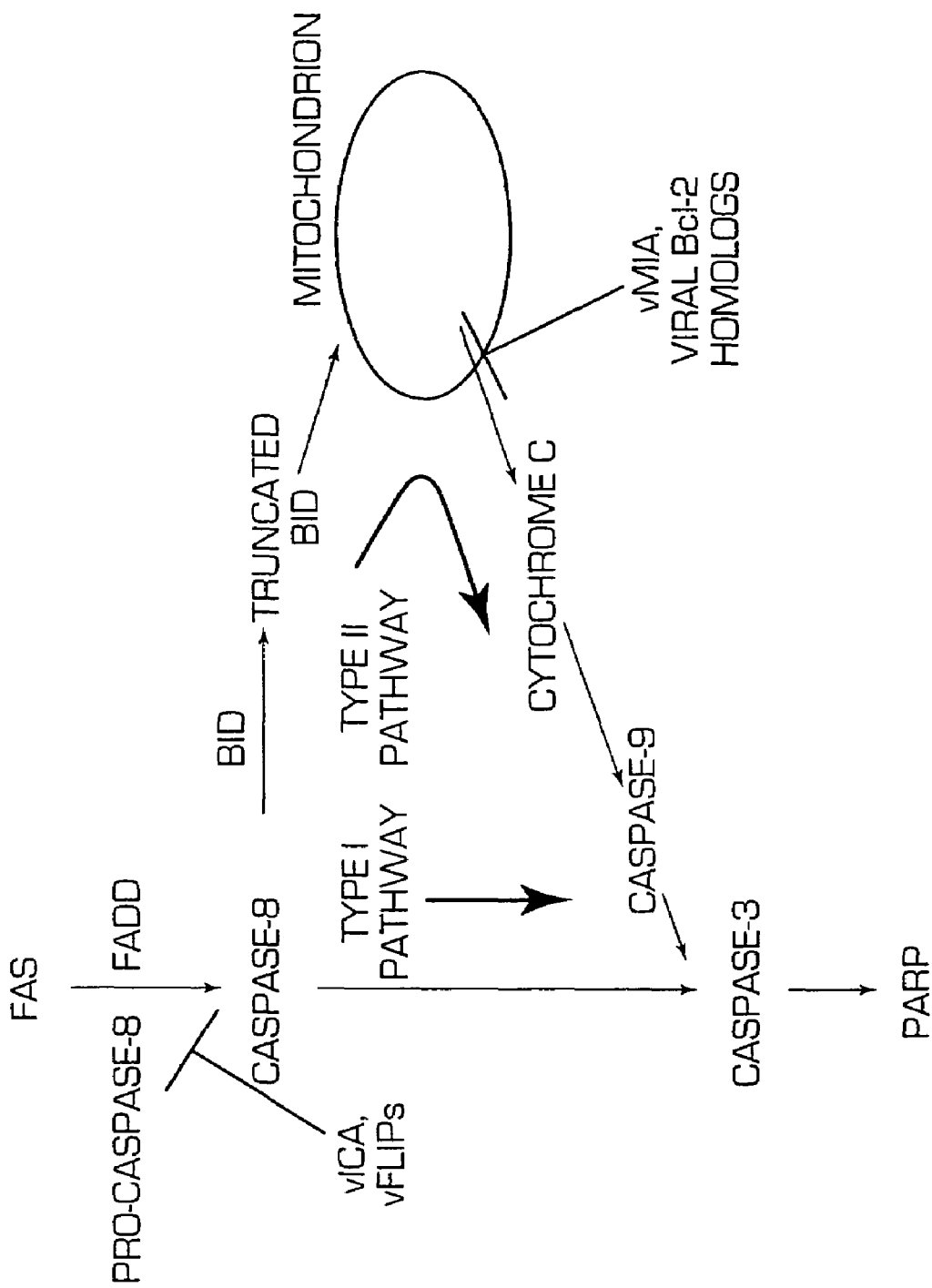

FIG. 18 shows strategies used by CMV and other herpesviruses to block apoptosis. These viruses interfere with at least two steps of the two major apoptotic pathways. vICA (CMV) or viral FLIPs encoded by other herpesviruses block caspase-8 activation, and thereby prevent direct caspase-3 activation, as well as BID truncation, which leads to cytochrome c release from mitochondria with subsequent caspase-9 and caspase-3 activation. vMIA (CMV) or viral Bcl-2 homologs encoded by other herpesviruses inhibit cytochrome c efflux from mitochondria, and thus inhibit subsequent steps of mitochondrial apoptotic signaling pathway.

Figure 19A:
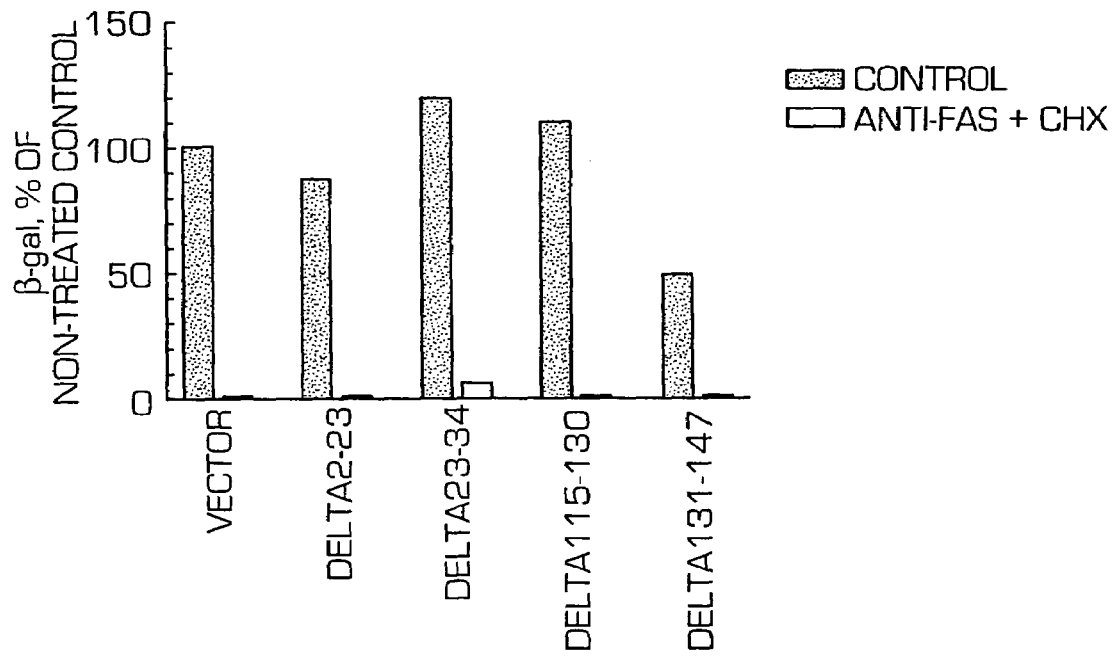
Figure 19B:
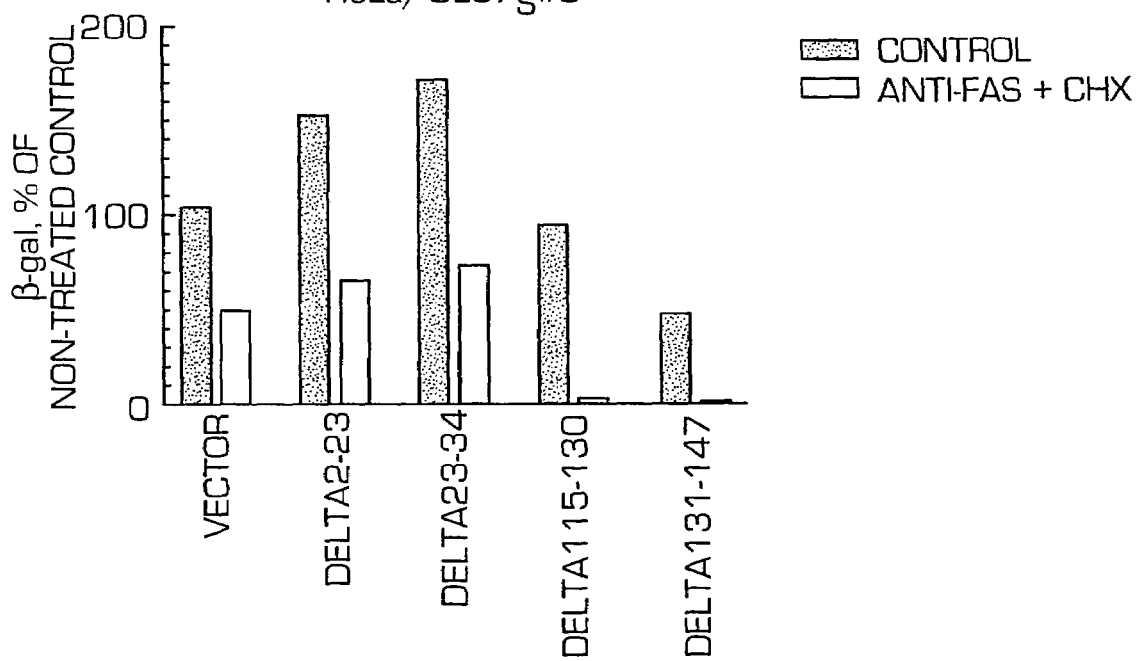

FIGS. 19A and 19B are histograms showing the effect of anti-Fas antibody in the presence of CHX on HeLa/pcDNA3-A cells (FIG. 19A) and HeLa/UL37x1#3 cells (FIG. 19B) transfected with different $pUL37_S$ deletion mutant genes. The open bars represent cells treated with anti-Fas antibody+CHX. The filled bars represent non-treated control cells. Each of the deletion mutants was previously shown to lack anti-apoptotic activity.

Figure 20:

FIG. 20 is a photograph of a Western blot analysis of $pUL37_S$ expression in MRC-5 fibroblasts at 4, 8, 24, and 72 h post-infection with HCMV (Towne$_{RIT}$ strain). Cell lysates of the infected cells were prepared at the indicated times for use in the Western blot analysis. $pUL37_S$ expression was detected by antiserum raised against the 22-amino acid C-terminal peptide of $pUL37_S$ and horse radish peroxidase-labeled anti-rabbit IgG antiserum, using the ECL method (Amersham).

DETAILED DESCRIPTION OF THE INVENTION

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Standard reference works setting forth the general principles of recombinant DNA technology include Sambrook, J., et al. (1989) *Molecular Cloning: A Laboratory Manual, 2d Ed.*, Cold Spring Harbor Laboratory Press, Planview, N.Y.; McPherson, M. J., Ed. (1991) *Directed Mutagenesis: A Practical Approach*, IRL Press, Oxford; Jones, J. (1992) *Amino Acid and Peptide Synthesis*, Oxford Science Publications, Oxford; Austen, B. M. and Westwood, O. M. R. (1991) *Protein Targeting and Secretion*, IRL Press, Oxford. Any suitable materials and/or methods known to those of ordinary skill in the art can be utilized in carrying out the present invention; however, preferred materials and/or methods are described. Materials, reagents and the like to which reference is made in the following description and examples are obtainable from commercial sources, unless otherwise noted.

DESCRIPTION OF THE EMBODIMENTS

The term "polypeptide" is used herein as a generic term to refer to an isolated or synthetic full-length protein; or an isolated or synthetic full-length oligopeptide; wherein the protein or oligopeptide has a minimum size of 2 amino acids.

The term "amino acid" is used herein to denote a single amino acid and/or analogs, and/or modified forms thereof.

The term "polynucleotide" is used herein as a generic term to refer to an isolated full-length DNA or RNA; or synthetic full-length DNA and/or RNA; isolated DNA or RNA oligonucleotides; or synthetic DNA and/or RNA oligonucleotides, wherein such a DNA and/or RNA has a minimum size of 2 nucleotides.

The term "nucleotide" is used herein to denote 5'-dNMP, -dNDP, -dNTP, -rNMP, -rNDP, -rNTP; and/or analogs and/or modified forms thereof.

The term "physiological molecule" is used herein as a generic term to refer to a naturally occurring molecule found in a cell such as a polypeptide, polynucleotide, amino acid, and/or nucleotide. Preferred physiological molecules are, e.g., FADD, FLICE (pro-caspase-8), caspase 3 (cpp32), Apaf-1, Bcl-$x_L$, Bak, ICE, Bax, BNIP-3, and ANT.

The term "accessory" is used herein to denote those physiological molecules that specifically bind to viral polypeptides having anti-apoptotic activity. Examples of such physiological molecules are polypeptide, polynucleotide, DNA, RNA, amino acid, and nucleotide molecules. Preferred accessory polypeptides are, e.g., FADD, FLICE (pro-caspase-8), caspase 3 (cpp32), Apaf-1, Bcl-$x_L$, Bak, ICE, Bax, BNIP-3, and ANT.

The term "compound" is used herein to denote a chemical or biological compound. Examples of such chemical or biological compounds include but are not limited to, polypeptide, polynucleotide, DNA, RNA, amino acid, and/or nucleotide compounds, including but not limited to synthetic forms of such compounds, and/or chemically and/or genetically modified forms of such compounds.

Polynucleotides are "homologous" to the specific HCMV polynucleotides of the present invention if they encode each of the domains required for anti-apoptotic activity of the specific HCMV protein. The activity need not be quantitatively similar or the same. Thus, in the case of $UL37_S$, any polynucleotide comprising a polynucleotide that encodes amino acid residues 5-34 and 118-147 of the native $pUL37_S$ protein would be a "homologue" of, or "homologous" to, $UL37_S$.

Similarly, polypeptides are "homologous" to the specific HCMV polypeptides of the present invention if they contain each of the domains required for anti-apoptotic activity of the specific HCMV polypeptides. The activity need not be quantitatively similar or the same. Also in the case of $pUL37_S$, any polypeptide comprising a polypeptide that contains amino acid residues 5-34 and 118-147 of the native $pUL37_S$ protein would be a "homologue" of, or "homologous" to, $pUL37_S$.

Two polynucleotides share sequence "identity" if the two polynucleotides or designated segments thereof, when optimally aligned with appropriate nucleotide insertions or deletions, are identical in at least about 50% of the nucleotides. "Substantial sequence identity" in the polynucleotide context means that the nucleic acids or their complementary strands, when compared, are identical when optimally aligned with appropriate nucleotide insertions or deletions, in at least about 60% of the nucleotides, usually at least about 70%, more usually at least about 80%, preferably at least about 90%, and more preferably at least about 95 to 98% of the nucleotides. Alternatively, substantial sequence identity exists between a first and second polynucleotide when the first polynucleotide will hybridize under selective hybridization conditions, to the second polynucleotide. Selectivity of hybridization exists when hybridization occurs with a certain degree of specificity rather than being random. Typically, selective hybridization will occur when there is at least about 55% identity over a stretch of at least about 14 nucleotides, preferably at least about 65%, more preferably at least about 75%, and most preferably at least about 90%. See, Kanehisa (1984) *Nuc. Acids Res.*, 12, 203-213.

Two polypeptides share sequence "identity" if the two polypeptides or designated segments thereof, when optimally aligned with appropriate amino acid insertions or deletions, are identical in at least about 50% of the amino acids. "Substantial sequence identity" in the polypeptide context means that the amino acids, when compared, are identical when optimally aligned with appropriate amino acid insertions or deletions, in at least about 60% of the amino acids, usually at least about 70%, more usually at least about 80%, preferably at least about 90%, and more preferably at least about 95 to 98% of the amino acids.

The term "substantially pure" means that the polypeptide or molecule of interest is essentially free from any other detectable biological constituents.

A "fragment" of a molecule (e.g., a molecule such as a polypeptide having anti-apoptotic activity or a polynucleotide encoding such a polypeptide) is meant to refer to any piece or segment of the molecule that is shorter than the full-length (or entire) molecule, wherein: 1) the piece or segment possesses the biological activity of the full-length (or entire) molecule, e.g., possesses the anti-apoptotic activity of the full-length anti-apoptotic polypeptide; or, alternatively, 2) the piece or segment of said full-length (or entire) molecule does not possess the biological activity of the full-length (or entire) molecule, e.g., does not possess the anti-apoptotic activity of the anti-apoptotic polypeptide, and the piece or segment of the full-length (or entire) molecule is useful for screening for and/or identifying compounds that regulate or modulate apoptosis and/or anti-apoptotic activity; and/or the piece or segment of the full-length (or entire) molecule is useful in itself for regulating or modulating apoptosis and/or anti-apoptotic activity. An example of the former fragments is pUL37Δ35-112/Δ148-163 (see Example 20, below). Examples of the latter fragments are deletion mutants pUL37$_S$Δ131-147 and pUL37$_S$Δ115-130 (see Example 13, below).

A "variant" of a molecule is meant to refer to a molecule substantially similar in structure and biological activity or immunological characteristics to either the entire molecule, or to a fragment of the entire molecule. Thus, provided that two molecules possess a similar activity, they are considered variants as that term is used herein even if the compound or secondary, tertiary, or quaternary structure of one of the molecules is not identical to that found in the other, or if the sequence of amino acid residues is not identical.

An "analog" of a molecule is meant to refer to a molecule substantially similar in function to either the entire molecule or to a fragment of the entire molecule.

As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are described, for example, in *Remington's Pharmaceutical Sciences* 17 th Ed. (1990) Mack Publishing Co., Easton, Pa. Procedures for coupling such moieties to a molecule are well known in the art.

By the term "hybrid polypeptide" is intended for the purposes of this invention, polypeptides which are hybrid polypeptides of: 1) the present polypeptides having anti-apoptotic activity, e.g., pUL36, pUL37$_S$, pUL37$_M$, and pUL37$_L$, fragments thereof, and/or functional equivalents or mutants thereof; and 2) other apoptosis-associated polypeptides encoded by genes, for example, FADD, FLICE (pro-caspase-8), caspase 3 (cpp32), Apaf-1, Bcl-x$_L$, Bak, ICE, Bax, BNIP-3, and ANT, fragments thereof, and/or functional equivalents thereof; producing a polypeptide which exhibits enhanced regulation or modulation of apoptosis and/or anti-apoptotic activity compared to that exhibited by the anti-apoptotic polypeptide alone. Such hybrids can be produced, for example, by fusing the first half of the coding region of the cDNA encoding the polypeptide having anti-apoptotic activity, with the second half of the coding region of the cDNA encoding FADD, FLICE (pro-caspase-8), caspase 3 (cpp32), Apaf-1, Bcl-x$_L$, Bak, ICE, Bax, BNIP-3, and ANT, or vice versa.

Additionally, by adding segments of the cDNA encoding FADD, FLICE (pro-caspase-8), caspase 3 (cpp32), Apaf-1, Bcl-x$_L$, Bak, ICE, Bax, BNIP-3, and ANT, to the cDNA encoding the polypeptide having anti-apoptotic activity, or replacing segments of the cDNA encoding the polypeptide having anti-apoptotic activity with segments of the cDNA encoding FADD, FLICE (pro-caspase-8), caspase 3 (cpp32), Apaf-1, Bcl-x$_L$, Bak, ICE, Bax, BNIP-3, and ANT, chimeric gene products of therapeutic value can be generated. One of ordinary skill in the art can readily produce and employ such hybrids using techniques well known in the art. One of ordinary skill in the art can readily determine whether a particular hybrid exhibits enhanced, decreased or intermediate levels of apoptotic activity and/or anti-apoptotic activity using known screening methods and as described herein.

By the term "normal cell behavior" is intended for the purposes of this invention, cells in which apoptosis proceeds normally. Normal cell behavior is observed in an organism which is able to remove senescent, damaged, or abnormal cells that could interfere with organ function or develop into tumors. Apoptosis which proceeds normally represents a coordinated cellular response to noxious stimuli that are not immediately lethal.

As used herein, the term "domain" refers to a domain identified in a polypeptide having anti-apoptotic activity, that may be essential for the interaction of such a anti-apoptotic polypeptide with a physiological molecule involved in the regulation or modulation of apoptosis and/or anti-apoptotic activity, and compounds capable of mimicking the domain's structure and/or function.

"Functional equivalent" is defined as a polypeptide possessing a biological activity or immunological characteristic substantially similar to that of a biologically active or functional domain (as described above), or that of a polypeptide having anti-apoptotic activity, such as pUL36, pUL37$_S$, pUL37$_M$, or pUL37$_L$, and is intended to include "fragments," "variants," "analogs," "homologs," and "chemical derivatives" possessing such activity or characteristic. Functional equivalents of the domain, or polypeptide having anti-apoptotic activity, may not share an identical amino acid sequence. Conservative or non-conservative amino acid substitutions of conventional or unconventional amino acids are possible.

Reference herein to "conservative" amino acid substitution is intended to mean the interchangeability of amino acid residues having similar side chains. For example, glycine, alanine, valine, leucine and isoleucine make up a group of amino acids having aliphatic side chains; serine and threonine are amino acids having aliphatic-hydroxyl side chains; asparagine and glutamine are amino acids having amide-containing side chains; phenylalanine, tyrosine and tryptophan are amino acids having aromatic side chains; lysine, arginine and histidine are amino acids having basic side chains; aspartic acid and glutamic acid are amino acids having acidic side chains; and cysteine and methionine are amino acids having sulfur-containing side chains. Interchanging one amino acid from a given group with another amino acid from that same group would be considered a conservative substitution. Preferred conservative substitution groups include asparagine-glutamine, alanine-valine, lysine-arginine, phenylalanine-tyrosine and valine-leucine-isoleucine.

By the term "degenerative disorder" is intended for purposes of this invention, any disorder characterized by inappropriate cell proliferation or inappropriate cell death or in some cases, both, or aberrant or disregulated apoptosis.

By the term "inappropriate cell proliferation" is intended a statistically significant increase in cell number as compared to the proliferation of that particular cell type in the normal population. Also included are disorders whereby a cell is present and/or persists in an inappropriate location, e.g., the presence of fibroblasts in lung tissue after acute lung injury. For example, such cells include cancer cells which exhibit the properties of invasion and metastasis and are highly anaplastic. Such cells include but are not limited to, cancer cells including, for example, tumor cells.

By the term "inappropriate cell death" is intended a statistically significant decrease in cell number as compared to the presence of that particular cell type in the normal population. Such under-representation may be due to a particular degenerative disorder, including, for example, AIDS (HIV), which results in the inappropriate death of T-cells, autoimmune diseases which are characterized by inappropriate cell death.

By the term "stable" is intended the state achieved when a statistically significant decrease in cell number is no longer observed in the individual being treated, as compared to the cell number observed at the onset of the course of treatment.

The compounds and methods of the present invention can regulate or modulate apoptotic activity and/or anti-apoptotic activity, for example, by inhibiting, diminishing, restoring, or inducing such activity. Such regulation and/or modulation can be determined, for example, by measuring the number of cells of the particular affected cell type that remain stable, increase, or decrease, in comparison to the normal cell population.

Detecting the Expression of Viral Polypeptides

Expression of viral polypeptides, such as HCMV polypeptides, in cells can be detected by a variety of standard protocols for detecting polypeptides known to those of ordinary skill in the art. For example, viral polypeptides can be detected by Western Blot analysis with a polyclonal or monoclonal antibody that recognizes and binds to the viral polypeptides. The antibody can be modified chemically or genetically to facilitate the detection of viral polypeptides. Further, viral polypeptides can be detected by immunofluorescence using a polyclonal or monoclonal antibody that recognizes and binds to the viral polypeptides. Fluorescence of the bound antibody can be generated by tagging the primary antibody with a fluorescent molecule or binding a secondary antibody containing a fluorescent molecule to the primary antibody. Such methods are well known to those of ordinary skill in the art and are described in Current Protocols in Molecular Biology, John Wiley & Sons, 1998; Current Protocols in Immunology, John Wiley & Sons, 1998; the Invitrogen Catalog, 1998; and the Kodak Scientific Imaging Systems Catalog, 1996/1997; each of which is incorporated herein by reference.

A preferred embodiment is the expression of $pUL37_S$ in HCMV-infected eukaryotic cells, for example MRC-5 cells, detected by Western Blot analysis with rabbit polyclonal antibodies that recognize KLH-conjugated polypeptides corresponding to the C-terminal amino acids of $pUL37_S$, wherein such antibodies also recognize $pUL37_L$.

Another preferred embodiment is the expression of pUL36 in HCMV-infected eukaryotic cells, for example MRC-5 cells, detected by Western Blot analysis with rabbit polyclonal antibodies that recognize KLH-conjugated polypeptides corresponding to pUL36.

Methods of Detecting Polypeptides Having Anti-Apoptotic Activity

Apoptosis can be restored, induced, or modulated in cells by treating the cells with an agent that leads to cell death. Suitable agents include, but are not limited to, those agents that bind to Fas receptor (Fas), a tumor necrosis factor receptor (TNF-R), or activate the caspase signal transduction pathway for apoptosis. For example, tumor necrosis factor receptor 1 (TNF-R1)-mediated apoptosis can be restored, induced, or modulated by exposure of cells, such as MRC-5 cells, to TNF-α in the presence of cycloheximide (CHX). Alternatively, Fas-mediated apoptosis can be restored, induced, or modulated by exposure of cells to anti-Fas antibody in the presence of CHX. The degree of cell death or apoptosis can then be measured by a variety of methods such as those described in Sellers, J. R., Cook, S., and Goldmacher, V. S. (1994) *J. Immunol. Meth.* 172, 255-264 and references cited therein; Telford, W. G., King, L. E., and Fraker, P. J. (1994) *J. Immunol. Meth.* 172, 1-16 and references cited therein; Poirier, J., Ed. (1997) *Apoptosis Techniques and Protocols*, Humana Press, Totowa, N.J.; each of which is incorporated herein by reference. Also such methods include those described below, such as the direct visual scoring of surviving cells under a phase microscope.

Further, the time course of apoptosis can be analyzed by measuring the level of expression of phosphatidylserine on the cell surface, as detected, for example, with FITC-labeled Annexin V, and/or by a dye-exclusion test using propidium iodide. These two tests can be performed using a commercially available kit, for example, the ApoAlert Annexin V Apoptosis kit (Clontech), in accordance with the manufacturer's recommendations, and using a flow cytometer (FACScan, Becton-Dickinson) or fluorescent microscope.

Furthermore, the cells can be transfected with an indicator plasmid carrying a reporter gene encoding an indicator molecule, and the degree of cell death or apoptosis can be measured by detection of the expressed indicator molecule. For example, the degree of apoptosis in cells transfected with an indicator plasmid expressing the indicator *E. coli* β-galactosidase can be determined by a β-galactosidase ELISA (Boehringer Mannheim), in accordance with the manufacturer's recommendations. Also, the degree of apoptotic activity can be determined by visually scoring, under a microscope, blue cells expressing β-galactosidase, after staining them with X-gal. As another example, the degree of apoptosis in cells transfected with an indicator plasmid expressing Green Fluorescent Protein can be determined by measuring the fraction of fluorescent cells in the total cell population, using a flow cytometer (FACScan, Becton-Dickinson) or fluorescent microscope.

Further, DNA degradation, indicative of apoptosis, can be examined by exposing the cells to anti-Fas antibody in the presence of CHX. Thereafter, the DNA in the cells is extracted and purified using standard protocols. Any methods detecting cell death or apoptosis can be used such as those described in Sellers, J. R., Cook, S., and Goldmacher, V. S. (1994) *J. Immunol. Meth.* 172, 255-264 and references cited therein; Telford, W. G., King, L. E., and Fraker, P. J. (1994) *J. Immunol. Meth.* 172, 1-16 and references cited therein; Poirier, J., Ed. (1997) *Apoptosis Techniques and Protocols*, Humana Press, Totowa, N.J.; each of which is incorporated herein by reference.

Accordingly, the anti-apoptotic activity of viral polypeptides, i.e., the inhibition or diminution of apoptotic activity, can be detected by measuring the relative levels of apoptotic activity exhibited in one portion of a cell culture transfected with viral polynucleotides encoding at least one polypeptide having anti-apoptotic activity, compared to a second portion of the same cell culture that is not transfected, or is transfected with polynucleotides that do not encode a polypeptide having anti-apoptotic activity (control cells).

For example, one portion of a cell culture can be transfected with a fragment of a HCMV polynucleotide encoding a polypeptide having anti-apoptotic activity. Whereas, a second portion of the same cell culture can be transfected with a polynucleotide that does not encode a polypeptide having anti-apoptotic activity (control cells). Anti-apoptotic activity, i.e., the inhibition or diminution of apoptosis, can then be detected by comparing the degree of apoptotic activity detected in the portion of cells transfected with the viral polynucleotide relative to the degree of apoptotic activity detected in the control cells.

A preferred embodiment is a method of detecting the apoptotic activity of HCMV-infected cells or host cells transfected with a fragment of HCMV polynucleotide encoding at least one of pUL36 (including any unspliced and, alternatively, spliced variants of the polypeptide encoded by UL36), pUL37$_S$, pUL37$_M$, or pUL37$_L$, or encoding at least one fragment of such HCMV polypeptides.

Methods of Screening for and Identifying Viral Polypeptides Having Anti-Apoptotic Activity Various methods can be employed to restore, induce, or modulate apoptosis. For example, the host cells can be treated with anti-Fas antibodies or treated with tumor necrosis factor-α (TNF-α). Both methods of treatment activate the apoptotic signaling pathways involved in the elimination of virally-infected cells in the host animals (Mestan et al., 1986; Vilcek and Sen, 1996; Wong et al., 1986; Kagi et al., 1994; Sieg, et al., 1996; Razvi and Welsh, 1995; each of which is incorporated herein by reference).

Transfection of eukaryotic cells with viral polynucleotides encoding viral polypeptide can prevent anti-Fas antibody- and TNF-α-induced apoptosis. Protection of the host cells from apoptosis indicates that viral gene products, e.g., anti-apoptotic viral polypeptides, prevent apoptosis induced by anti-Fas antibody and TNF-α and, consequently, such protection provides a method of screening for viral polynucleotides encoding polypeptides having anti-apoptotic activity.

In a preferred embodiment, transfection of cells with HCMV polynucleotide prevents anti-Fas antibody- and TNF-α-induced apoptosis. Protection of the host cells from apoptosis indicates that HCMV anti-apoptotic polypeptides prevent apoptosis induced by anti-Fas antibody and TNF-α and, consequently, such protection provides a method of screening for HCMV polynucleotides encoding polypeptides having anti-apoptotic activity, such as pUL36 (or any unspliced or spliced variants of the polypeptide encoded by UL36), pUL37$_S$, pUL37$_M$, and pUL37$_L$.

In a preferred embodiment, HeLa cells transfected with a viral polynucleotide, encoding a polypeptide, are exposed to the anti-Fas monoclonal antibody 7C11+CHX or to TNF-α+CHX, and cell death is measured by visual scoring of the cells under a phase microscope. Alternatively, the induced cell death or apoptosis of the HeLa cells, can be examined by a dye-exclusion test on a flow cytometer. Fas-mediated apoptosis is accompanied by the characteristic apoptotic events: 1) surface blebbing, as observed under a phase microscope (not shown); 2) emergence of phosphatidylserine, an early marker of apoptosis in the outer layer of the cell plasma membrane; 3) DNA degradation (not shown); and 4) protection by a caspase inhibitor, for example, Z-VADfmc.

In the course of viral infection, the cells can gradually develop resistance to TNF-R1 and Fas-mediated apoptosis. Although early in viral infection, i.e., on day 0 and day 1 of infection, the cells can still be sensitive to anti-Fas antibody+CHX- and TNF-α+CHX-induced apoptosis. By day 2 most of the cells in the infected culture can become insensitive to these stimuli, which is evident by microscopic examination of cell death (FIG. 1). A flow-cytometric PI dye-exclusion test and the test for the surface expression of phosphatidylserine by apoptotic cells can confirm that a major fraction of virally-infected cells (72 h post-infection) retains the capacity to exclude the dye, and not express phosphatidylserine following exposure to anti-Fas antibody+CHX (data not shown). Thus, such findings provide a method of screening for viral polypeptides having anti-apoptotic activity and viral polynucleotides encoding such polypeptides.

A preferred embodiment is a method of screening for HCMV polypeptides having anti-apoptotic activity and HCMV polynucleotides encoding such polypeptides. An example of such HCMV polypeptides is pUL36 (and any unspliced and alternatively spliced variants of the polypeptide encoded by UL36), pUL37$_S$, pUL37$_M$, and pUL37$_L$.

Suitable candidate polypeptides can be identified by using an assay where an increased expression of a marker gene product, such as β-galactosidase or a fluorescent polypeptide, is indicative of anti-apoptotic activity. In such an assay, a first portion of cells from a culture of cells is co-transfected with an expression plasmid encoding a marker polypeptide and an expression plasmid vector containing a DNA insert encoding a candidate polypeptide. In parallel, as a control, a second portion of cells from the same culture is co-transfected with the expression plasmid encoding a marker polypeptide and the "empty" expression plasmid vector which lacks the DNA insert encoding a candidate polypeptide ("empty vector").

The cells are then treated with an agent, such as anti-Fas antibody or TNF-α, under conditions that induce apoptosis. The expression of the marker polypeptide in the induced cells is then measured after a sufficient amount of time for apoptosis to be completed (typically overnight). Any candidate polypeptide encoded by the DNA insert contained in the plasmid expression vector that supports the increased expression of the marker polypeptide compared to that of the empty vector is then selected as a candidate polypeptide and subjected to further testing for anti-apoptotic activity.

Figure 5:
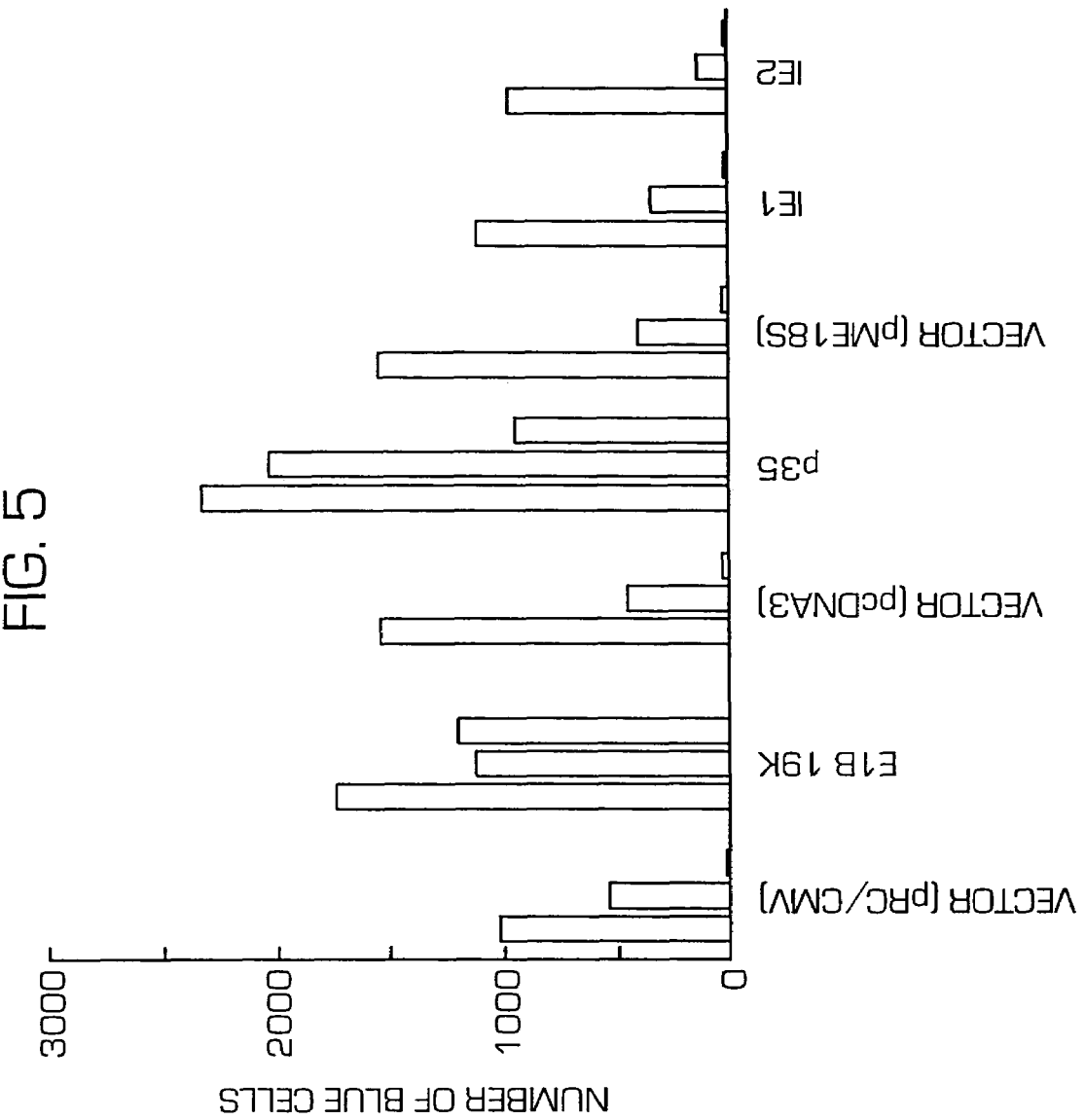
FIG. 5 is a histogram showing the effect of anti-Fas antibody, in the presence of CHX, on HeLa cells expressing the HCMV polypeptide IE1 or IE2. In the histogram, the results are represented in sets of three filled bars, wherein the left bar represents the control cells (untreated), the middle bar represents the cells treated with CHX, and the right bar represents the cells treated with anti-Fas antibody+CHX. As a positive control, other HeLa cells were transfected with either the adenovirus E1B 19K gene or the baculovirus p35 gene, both encoding anti-apoptotic polypeptides. As a negative control, additional HeLa cells were transfected with empty expression plasmid vectors, pME18S, pRC/CMV or pcDNA3. All replicates were also transfected with a vector carrying the α-galactosidase reporter gene (pCMVβ).
Figure 6A:
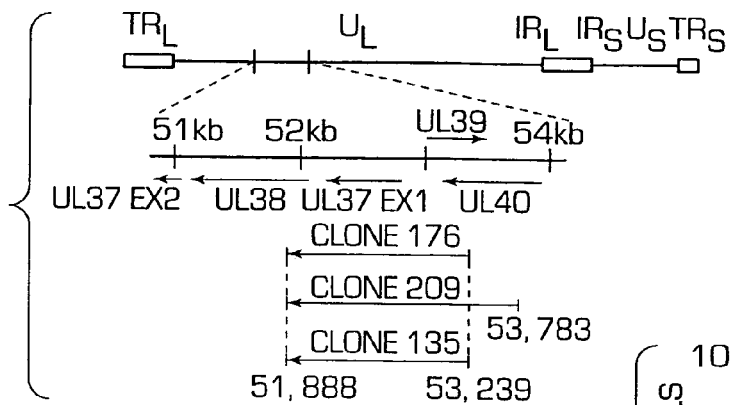
FIG. 6A is a schematic map showing the structure of the HCMV (AD169) genome and UL37 region and associated open reading frames, and HCMV DNA inserts (in plasmids) isolated from three independent library pools and designated clones 176, 209, and 135. The arrows indicate the orientation of the inserts relative to the promoter in the expression vector.
Figure 6B:
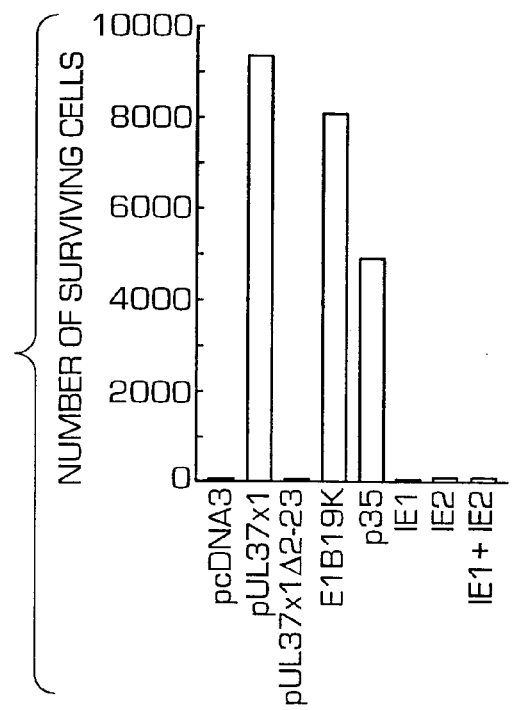
FIG. 6B is a histogram showing the number of surviving cells at 24 h post-transfection wherein the cells were transiently transfected with expression plasmids (1 μg) encoding pUL37$_S$myc ("pUL37x1"), pUL37$_S$Δ2-23myc (pUL37x1Δ2-23), E1B19K, baculovirus p35 ("p35"), HCMV IE1 ("IE1"), HCMV IE2 ("IE2"), or a 1:1 mixture of the plasmids containing IE1 and IE2 ("IE1+IE2"), or pcDNA3 (empty vector, control). 24 h post-transfection the cells were exposed to anti-Fas antibody+CHX for an additional 24 h and the surviving cells were scored under a microscope.

Two examples of known anti-apoptotic polypeptides, the adenoviral E1B 19k and the baculoviral p35, that were subjected to such an assay are shown in FIG. 5. The results of the assay indicate that the E1B 19K sample diluted 1:10,000 with the empty vector is a suitable candidate for additional testing and illustrate the utility of such an assay in identifying suitable candidate polypeptides. Similarly, FIG. 6B shows the results of such an assay performed on expression plasmid vectors containing HCMV genomic DNA inserts encoding candidate polypeptides. Any pool of plasmids expressing a level of the marker gene product above background encode candidate polypeptides that are to be tested further for anti-apoptotic activity (see text below for further details).

Methods of Screening for and Identifying Polynucleotides Encoding Polypeptides Having Anti-Apoptotic Activity To screen for and identify viral polynucleotides encoding a polypeptide having anti-apoptotic activity, a DNA library transfected into eukaryotic cells, for example HeLa cells, can be screened. The ability of the HeLa cells to undergo Fas- or TNF-R1-mediated apoptosis is similar to that of MRC-5 fibroblasts. HeLa cells undergo apoptosis when exposed to either an anti-Fas antibody+CHX, or TNF-α+CHX. In a preferred embodiment anti-Fas antibody, 7C11, is used to induce apoptosis in HeLa cells, in the presence of CHX.

In order to construct a DNA library, viral polynucleotide is partially digested with at least one restriction enzyme and then ligated into a plasmid expression vector. For example, viral DNA can be partially digested with Sau3AI and ligated into the pZeoSV2(+) plasmid expression vector. The average insert size of the library is typically 3.5 kb (the range 1.7-13 kb).

In a preferred embodiment, the DNA library is constructed using HCMV DNA. The sequences of most of the predicted HCMV genes either contain no introns or contain exons that are located in close proximity to each other (Chee et al., 1990, which is incorporated herein by reference). Consequently, HCMV DNA containing a full-length gene sequence may be represented in a single plasmid, in a library containing an average insert size of 3.5 Kb.

The screening of the library is based on the present inventors' finding that even a very low concentration (e.g., as low as 0.1% to 1% of the total DNA transfected) of a transfected expression plasmid carrying an anti-apoptotic gene, such as adenoviral E1B 19K, baculovirus p35 (FIG. 5), human Bcl-$x_L$, or human Bcl-2, mixed with a high concentration of a control vector, that does not encode a polypeptide having anti-apoptotic activity, offered a detectable protection of HeLa cells against anti-Fas antibody-induced apoptosis in the presence of CHX. Thus, in the preferred embodiment, 212 pools of the library plasmids (with an average complexity of 500 colonies/pool) are prepared and the anti-apoptotic activity of these pools of plasmids is compared in HeLa cells. The pools giving the strongest β-galactosidase signals are then divided into lower complexity sub-pools and evaluated in a similar test.

Finally, individual plasmids from the sub-pools with the highest β-galactosidase activity are re-tested, and those possessing anti-apoptotic activity are isolated. Positive isolates exhibit strong anti-apoptotic activity comparable to those plasmids carrying the Bcl-$x_L$ and E1B 19K genes introduced into cells by a similar transient transfection protocol. For example, 5 to 15% of cell populations transiently transfected with plasmids carrying the Bcl-$x_L$ and E1B 19K genes survive apoptosis induced by anti-Fas antibody+CHX, while nearly all cells (greater than 99.9%) in control cultures transfected with the control vector die, as observed under a microscope.

The DNA inserts of the positive clones can be identified by polynucleotide sequencing. In a preferred embodiment, these inserts represent two regions of the HCMV genome. The first region contains exon 1 of the UL37 gene with a hypothetical ORF between nucleotides 52,706-52,215 of the complementary strand of the AD169 genome (Tenney and Colberg-Poley, 1991a, b) coding for a potential polypeptide which is designated as pUL37$_S$. S stands for "short" since UL37 codes for another polypeptide product, pUL37$_L$ ("L" stands for long) translated from a spliced mRNA covering UL37 exons 1, 2, and 3. The second region contains an ORF encoded on the complementary strand in exons 1 and 2 of UL36 representing nucleotides 49,776-48,246 of the AD169 genome (Tenney and Colberg-Poley, 1991a, b). The polypeptide pUL36 is encoded within this region. In addition, variants of pUL36, including unspliced and alternatively spliced variants of pUL36, or other polypeptides may be encoded within this region.

The polypeptide pUL37$_L$ has been previously reported to be expressed by human cells infected with HCMV, and it has been proposed that most of the exon 1 sequence has no functional significance for replication of HCMV transactivating activity or intracellular localization (Zhang et al., 1996, which is incorporated herein by reference). Moreover, neither the expression of the hypothetical polypeptide pUL36 in any cells nor its possible function has been reported.

A preferred embodiment is a method of screening for HCMV polynucleotides encoding polypeptides having anti-apoptotic activity.

Methods of Isolating and Cloning Polynucleotides Encoding a Polypeptide Having Anti-Apoptotic Activity Genomic or cDNA clones encoding an anti-apoptotic polypeptide may be isolated from clone libraries (e.g., OriGene Technologies, Inc., Rockville, Md.) using hybridization probes designed on the basis of known nucleotide sequences and using conventional hybridization screening methods (e.g., Benton, W. D. and Davis, R. W., 1977; and Goodspeed et al., 1989; each of which is incorporated herein by reference). Where a cDNA clone is desired, clone libraries containing cDNA derived from viral RNA or from RNA isolated from cells expressing viral polypeptides, are preferred. Alternatively, synthetic polynucleotide sequences corresponding to the desired viral sequences may be constructed by chemical synthesis of oligonucleotides.

Additionally, the polymerase chain reaction (PCR), using primers based on the known viral sequence, may be used to amplify DNA fragments from genomic DNA, mRNA pools, or from cDNA clone libraries. U.S. Pat. No. 4,683,195 and U.S. Pat. No. 4,683,202 describe the PCR method. Additionally, PCR methods employing one primer that is based on the known viral sequence and a second primer that is not based on the known viral sequence, may be used. For example, a second primer that is homologous to or complementary to a vector sequence or sequence external to the viral sequence, may be used.

It is apparent to one of ordinary skill in the art that nucleotide substitutions, deletions, and additions may be incorporated into the polynucleotides of the invention. Nucleotide sequence variation may result from sequence polymorphisms of alleles, minor sequencing errors, and the like of the polynucleotide encoding an anti-apoptotic polypeptide. However, such nucleotide substitutions, deletions, and additions should not substantially disrupt the ability of the polynucleotide to hybridize to the known polynucleotide sequences, under hybridization conditions that are sufficiently stringent to result in specific hybridization.

Specific hybridization is defined herein as the formation of hybrids between a probe polynucleotide (e.g., a polynucleotide of the invention which may include substitutions, deletions, and/or additions) and a specific target polynucleotide (e.g., a polynucleotide of the invention, such as a polynucleotide encoding an anti-apoptotic polypeptide), wherein the probe preferentially hybridizes to the specific target such that, for example, a single band corresponding to one or more of the isoforms of an alternatively spliced mRNA species can be identified on a Northern blot of RNA prepared from a suitable cell source (e.g., cells expressing the anti-apoptotic polypeptide).

Polynucleotides of the invention and recombinantly produced polynucleotides, or analogs thereof, may be prepared on the basis of the sequence data, according to methods known in the art and described in Sambrook et al. (1989) *Molecular Cloning: Laboratory Manual, 2nd Ed.* Cold Spring Harbor, N.Y. and *Berger and Kimmel, Methods in Enzymology* (1987) Volume 152, Guide to Molecular Cloning Techniques, Academic Press, Inc., San Diego, Calif.; each of which is incorporated herein by reference.

Polynucleotides of the invention may be short oligonucleotides (e.g., 15-200 bases long), such as for use as hybridization probes and PCR (or LCR) primers. Polynucleotide sequences of the invention may also comprise part of a larger polynucleotide (e.g., a cloning vector comprising a clone) and may be fused, by polynucleotide linkage, in frame with another polynucleotide sequence encoding a different polypeptide (e.g., glutathione S-transferase or β-galactosidase) for encoding expression of a fusion polypeptide. Typically, the polynucleotides of the invention comprise at least 25 consecutive nucleotides which are substantially identical to a naturally-occurring polynucleotide of the invention, more usually the polynucleotides of the invention comprise at least 50 to 100 consecutive nucleotides which are substantially identical to a naturally-occurring polynucleotide sequence encoding an anti-apoptotic polypeptide. However, it will be recognized by those of ordinary skill in the art that the minimum length of a polynucleotide required for specific hybridization to a target sequence will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothioate, etc.), among others. See the discussion on sequence identity and homology at the beginning of this section (i.e., Description of the Embodiments).

If desired, PCR amplimers for amplifying substantially full-length cDNA copies may be selected at the discretion of the practitioner. Similarly, amplimers to amplify single exons or portions of the particular polynucleotide of the invention may be selected.

Each of these sequences may be used as hybridization probes or PCR amplimers to detect the presence of a particular species of RNA, for example to diagnose a viral disease characterized by the presence of an elevated or reduced level of a particular species of RNA in, for example lymphocytes, or to perform tissue typing (i.e., identify tissues characterized by the expression of a particular species of RNA), and the like. The sequences may also be used for detecting genomic polynucleotide sequences in a DNA sample, such as for forensic DNA analysis (e.g., by RFLP analysis, PCR product length(s) distribution, etc.) or for diagnosis of diseases characterized by amplification and/or rearrangements of a particular gene.

Methods for Screening for and Identifying Domains of Anti-Apoptotic Polypeptides Required for Anti-Apoptotic Activity and Mitochondrial Localization Polynucleotides encoding polypeptides exhibiting anti-apoptotic activity may be mutated such that the resulting polypeptides have lost their anti-apoptotic activity. To screen for and identify domains of anti-apoptotic polypeptides that are required for anti-apoptotic activity, a series of deletion mutants that span the entire open reading frame (ORF) of a gene encoding a polypeptide shown to have anti-apoptotic activity is generated. Expression vectors encoding deletion mutants, and wild-type controls, are then expressed in eukaryotic cells, for example HeLa cells, and screened for anti-apoptotic activity. In a preferred embodiment, the assay for anti-apoptotic activity is conducted via a transient transfection assay wherein the ability of the HeLa cells to undergo Fas- or TNF-R1-mediated apoptosis, depending on the identity of the deletion mutant it is expressing, is judged. HeLa cells undergo apoptosis when exposed to either an anti-Fas antibody+CHX, or TNF-α+CHX. In a preferred embodiment the anti-Fas antibody, 7C 11, is used to induce apoptosis in HeLa cells, in the presence of CHX. Cells expressing a functional copy of an anti-apoptotic polypeptide will not undergo anti-Fas antibody or TNF-α induced apoptosis. In contrast, deletion mutants expressing a non-functional form of the polypeptide will undergo anti-Fas antibody or TNF-α induced apoptosis.

The deletion mutants are constructed using commercially available kits, for example, the GeneEditor™ in vitro site directed mutagenesis kit (Promega) and the QuikChange™ site-directed mutagenesis kit (Stratagene). The starting material may be any polynucleotide encoding an anti-apoptotic protein, for example the HCMV gene UL37x1. The deletion mutants can be contained within an appropriate eukaryotic expression vector, such as pcDNA3.

The identity of the polynucleotide encoding the deletion mutants may be confirmed using a standard DNA sequencing method.

The screening of the mutants is based on the finding that even a very low concentration (e.g., as low as 0.1% to 1% of the total DNA transfected) of a transfected expression plasmid carrying an anti-apoptotic gene, such as adenoviral E1B 19K, baculovirus p35 (FIG. 5), human Bcl-$x_L$, or human Bcl-2, mixed with a high concentration of a control vector, that does not encode a polypeptide having anti-apoptotic activity, offered a detectable protection of HeLa cells against anti-Fas antibody-induced apoptosis in the presence of CHX. For example, 5 to 15% of cell populations transiently transfected with plasmids carrying the Bcl-$x_L$ and E1B 19K genes survive apoptosis induced by anti-Fas antibody+CHX, while nearly all cells (greater than 99.9%) in control cultures transfected with the control vector die, as observed under a microscope.

The deletion mutants may also be engineered to express an epitope tag fused to the deletion mutant. A preferred epitope tag is the myc epitope tag. Because some anti-apoptotic proteins localize to the mitochondria, the epitope tags can be used to determine whether the deletion mutants are localized to the mitochondria.

Again, HeLa cells transiently expressing the wild-type and deletion mutants can be exposed to either an anti-Fas antibody+CHX, or TNF-α+CHX. In a preferred embodiment the anti-Fas antibody, 7C11, is used to induce apoptosis in HeLa cells, in the presence of CHX. The cells may then be visually observed under a phase microscope. In a preferred embodiment, the myc tagged deletion mutants and wild-type control are detected with 9E10 anti-myc monoclonal antibody and counterstained with anti-human mitochondria antibody, mitotracker dye, or with one of the following endoplasmic reticulum markers: anti-calnexin, anti-calreticulin, or anti-PDI antibodies.

Methods of Screening for and Identifying a Polypeptide, Having Anti-Apoptotic Activity, Transiently Expressed in Eukaryotic Cells The anti-apoptotic activity of a specific polypeptide can be assayed for by transient expression in eukaryotic cells. Cells that transiently express a specific polypeptide are useful for characterizing the structural and functional properties of the polypeptide having anti-apoptotic activity, and also useful for characterizing the antiviral compounds that interact with or bind to the polypeptide and interfere with the anti-apoptotic activity of the polypeptide. For example, such an assay for detecting the anti-apoptotic activity of a specific viral polypeptide can be used to screen candidate antiviral compounds for their ability to interfere with the anti-apoptotic activity of a specific viral polypeptide and, thereby, induce or restore apoptosis. Further, the assay is useful in identifying and characterizing the functional domains of a specific polypeptide. For example, the specific polypeptide and polynucleotide sequence critical for anti-apoptotic activity or for intermolecular interactions of a specific polypeptide can be identified and characterized using such an assay. Moreover, the assay provides a method of identifying and characterizing the manner or region in which an antiviral compound interacts or binds to the viral polypeptide, under physiological conditions.

Figure 7B:
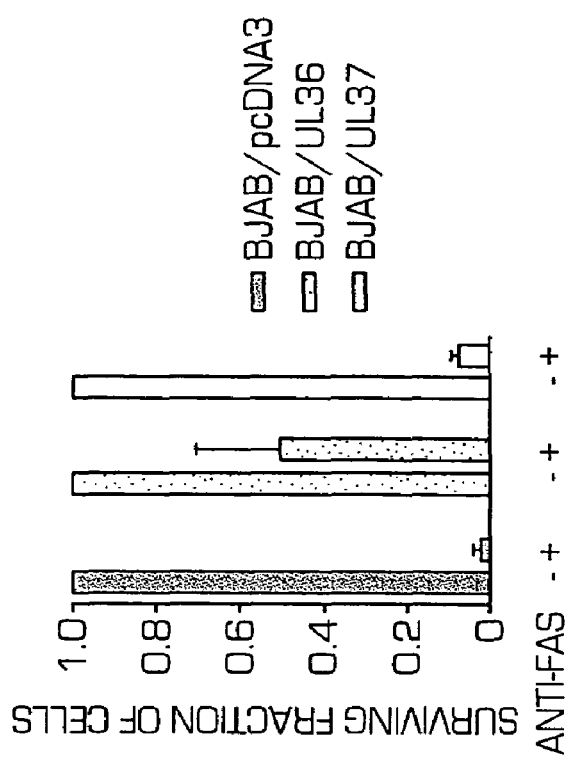
FIG. 7B is a histogram showing the number of surviving cells wherein the BJAB cells were transiently transfected with expression plasmids (1 μg) encoding either UL36, UL37 or the pcDNA3 empty vector. 24 hours after transfection, the cells were treated with anti-Fas antibody+CHX for an additional 24 h, or left untreated (−) and then scored under a microscope for surviving cells.

In a preferred embodiment, the anti-apoptotic activity of HCMV polypeptides $pUL37_S$ and pUL36 (or any unspliced or alternatively spliced variants of the polypeptide encoded by UL36) is confirmed by generating, individually, the regions of DNA closely covering the ORFs by PCR, ligating the PCR-generated fragment into the expression vector pCR3.1-uni, sequencing the cloned polynucleotide fragment, and testing the clone for anti-apoptotic activity in HeLa cells. Using this approach, the present inventors demonstrated that genomic sequences covering ORF $UL37_S$ or ORF UL36 protect HeLa cells against anti-Fas antibody+CHX-induced apoptosis (FIG. 7B). Further, the anti-apoptotic activity of any other polypeptides that may be encoded by the UL36 region, defined by nucleotides 49,776-48,246 of the HCMV AD169 genome, may be identified using this same approach.

In another preferred embodiment, the DNA covering the ORF of $pUL37_L$ is generated by PCR from a cDNA library prepared from HCMV-infected cells, ligated into an expression vector, sequenced, and several clones tested for anti-apoptotic activity in HeLa cells. Using this approach, the present inventors isolated clones having DNA sequences encoding an ORF that is shorter than that of $pUL37_L$, demonstrated that the polypeptide encoded by this ORF has anti-apoptotic activity, and designated the novel polypeptide $pUL37_M$.

Figure 6C:
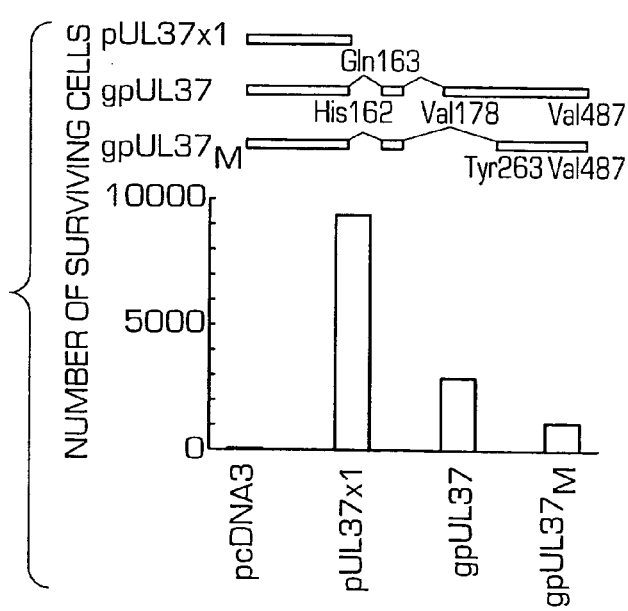
FIG. 6C is a schematic showing the alternatively spliced forms of UL37 pre-mRNA resulting in the mRNAs that encode pUL37$_S$ ("pUL37x1"), pUL37$_M$ ("gpUL37$_M$"), and pUL37$_L$ ("gpUL37"). The amino acid sequence numbers given for pUL37$_M$ correspond to the amino acid sequence numbers of pUL37$_L$. Underneath the schematic, in FIG. 6C, is a histogram showing the number of surviving cells wherein the cells were transfected with expression plasmids (1 μg) encoding pUL37$_S$myc ("pUL37x1"), pUL37$_M$ ("gpUL37$_M$"), pUL37$_L$ ("gpUL37"), or pcDNA3 (empty vector, control). 24 h post-transfection the cells were exposed to anti-Fas antibody+CHX for an additional 24 h, and the surviving cells were scored under a microscope.

In another preferred embodiment, the DNA covering the ORF of $pUL37_L$ is generated by PCR from a cDNA library made from HCMV-infected cells, ligated into an expression vector, sequenced, and the clone tested for anti-apoptotic activity in HeLa cells. The cDNA rather than genomic DNA is used to express $pUL37_L$ in order to prevent the expression of $pUL37_S$. Using this approach, the present inventors demonstrated that $pUL37_L$ is also anti-apoptotic (FIG. 6C, column 3).

Methods of Screening for and Identifying a Polypeptide, Having Anti-Apoptotic Activity, Stably Expressed in Eukaryotic Cells The anti-apoptotic activity of a specific polypeptide can be assayed for in eukaryotic cells stably transformed with a polynucleotide specifically encoding the polypeptide. A stably transformed cell line that continuously expresses the specific polypeptide is useful for characterizing the structural and functional properties of the polypeptide having anti-apoptotic activity, and also useful for characterizing the antiviral compounds that interact with or bind to the polypeptide and interfere with the anti-apoptotic activity of the polypeptide. For example, the assay is useful in identifying and characterizing the functional domains of a specific polypeptide. Also, the specific polypeptide and polynucleotide sequence critical for anti-apoptotic activity or for intermolecular interactions of a specific polypeptide can be identified and characterized using such an assay. Moreover, such an assay for detecting the anti-apoptotic activity of a specific viral polypeptide can be used to screen candidate antiviral compounds for their ability to interfere with the anti-apoptotic activity of a specific viral polypeptide and, thereby, induce or restore apoptosis. Also, the assay provides a method of identifying and characterizing the manner or region in which an antiviral compound interacts or binds to the viral polypeptide, under physiological conditions.

Clones encoding a polypeptide, having anti-apoptotic activity, can be stably transfected into eukaryotic cells using standard protocols known to those of ordinary skill in the art (e.g., see Sambrook et al., 1989, which is incorporated herein by reference) or by using commercially available transfection kits such as those sold by Stratagene, La Jolla, Calif., or Qiagen, Valencia, Calif. Such clones generated by stable transfection can continuously (as opposed to transiently) express the encoded polypeptide. Positives, i.e., cells stably transfected, are selected in a medium containing a selection agent, for example G418 or puromycin, that permits only stably transfected cells to survive.

The surviving clones, for example G418 or puromycin resistant clones, are then screened for the expression of the encoded polypeptide and the positive cells expressing the encoded polypeptide are isolated and subcultured. As an example, the transfected cells can be screened for the expressed polypeptide by Western Blot analysis using antibody that recognizes the polypeptide. Further, cells stably transfected with a control polynucleotide not encoding a polypeptide having anti-apoptotic activity, can be used as a negative control in the detection of the expressed polypeptide, such as in a Western blot analysis, and in experiments studying the anti-apoptotic activity of the clones. An example of a control polynucleotide is an expression vector that does not carry an inserted polynucleotide encoding a polypeptide having anti-apoptotic activity.

In a preferred embodiment, HeLa clones continuously (as opposed to transiently) express the version of $pUL37_S$ tagged with the C-terminal myc-peptide (amino acids 408-421 within the carboxy terminal domain of human c-Myc) generated by stable transfection with either an expression plasmid containing $UL37_S$ alone, or in a mixture with an expression plasmid coding for puromycin-N-acetyl-transferase such as pPUR (Clontech, Palo Alto, Calif.). Following the transfection, drug-resistant clones are selected in medium containing G418 (0.7 mg/ML) or in medium containing puromycin (1 µg/ml), and then the clones are screened for the expression of pUL36-myc-tagged and $pUL37_S$-myc-tagged polypeptides, respectively, by Western analysis with 9E10 anti-Myc antibody (Santa Cruz Biotechnology, Inc., Santa Cruz, Calif.). In using this approach, the present inventors isolated four clones that expressed $pUL37_S$-myc (designated as HeLa/$UL37_S$). These clones were then used to conduct further studies reported in Example 9. Also, four G418-resistant clones of HeLa cells stably transfected with pcDNA3/myc (empty vector, control) were isolated by similar procedures, two with G418 (HeLa/G418) and two with puromycin (HeLa/puro), and used as a negative control in the Western blot analysis and experiments studying the anti-apoptotic activity of the clones.

The sensitivity of the HeLa/$pUL37_S$ towards Fas- and TNF-R1-mediated apoptosis was tested. The four clones of each type were tested and all displayed a similar degree of anti-apoptotic activity. Virtually none of the HeLa/pUL37$_S$ cells underwent apoptosis induced by anti-Fas antibody+ CHX or TNF-α+CHX, while virtually all control cells (transfected with the pcDNA3/myc) died.

Methods of Screening for and Identifying Compounds, Such as Physiological Molecules, that Specifically Bind to Polypeptides Having Anti-Apoptotic Activity Physiological molecules, such as polypeptides, polynucleotides, RNA, DNA, amino acids, and nucleotides, specifically bind to viral polypeptides, having anti-apoptotic activity, and are potentially important apoptosis regulatory molecules. Such physiological molecules are also referred to herein as accessory molecules. Such accessory molecules may participate in the signaling or induction of apoptosis. Thus, the specific interaction of viral anti-apoptotic polypeptides with such molecules may prevent the molecule from functioning, thereby, interfering with apoptosis.

Methods of identifying such physiological molecules that interact specifically with viral polypeptides having anti-apoptotic activity have utility in the development of compounds and methods of screening for antiviral compounds. For example, antiviral compounds that diminish the specific binding of physiological molecules to viral polypeptides having anti-apoptotic activity could interfere with such activity and, thereby, induce or restore apoptosis.

Further, the identification and analysis of such physiological molecules is facilitated by the use of fragments of the viral polypeptides having anti-apoptotic activity. For example, a specific portion or fragment of the viral polypeptide having anti-apoptotic activity, such as a functional domain, may be used for screening for a physiological molecule that specifically binds to a specific sequence or domain of the viral polypeptide, and for characterizing the interaction of the physiological molecule with a specific sequence or domain of the viral polypeptide.

In addition, such viral polypeptides having anti-apoptotic activity may be modified using chemical methods or genetic engineering methods known in the art such as those described and referenced herein below under Modifications of Polynucleotides and Polypeptides. As an example, the polypeptides may be modified by the attachment of linkers that join two or more of the viral polypeptides, for the purposes of screening for and characterizing such physiological molecules. For example, two or more of the viral polypeptides having anti-apoptotic activity may be joined together by a peptide linker. As another example, the polypeptides may be modified by means of genetic engineering so that two or more of the polypeptides are joined together when expressed as a fusion polypeptide.

An embodiment is a method of identifying physiological molecules that specifically bind to viral polypeptides having anti-apoptotic activity. In addition, such viral polypeptides having anti-apoptotic activity may be modified using chemical methods or genetic engineering methods known in the art such as those described and referenced herein below under Modifications of Polynucleotides and Polypeptides.

Another embodiment is a method of identifying physiological molecules that specifically bind to HCMV polypeptides having anti-apoptotic activity. In addition, such HCMV polypeptides having anti-apoptotic activity may be modified using chemical methods or genetic engineering methods known in the art such as those described and referenced herein below under Modifications of Polynucleotides and Polypeptides.

Another embodiment is a method of identifying physiological molecules that specifically bind to at least one of HCMV polypeptides pUL36 (or any unspliced or alternatively spliced variants of the polypeptide encoded by UL36), pUL37$_S$, pUL37$_M$, or pUL37$_L$. In addition, such HCMV polypeptides may be modified using chemical methods or genetic engineering methods known in the art such as those described and referenced herein below under Modifications of Polynucleotides and Polypeptides.

A preferred embodiment is a method of identifying polypeptides that specifically bind to at least one of HCMV polypeptides pUL36, pUL37$_S$, pUL37$_M$, or pUL37$_L$. In addition, such HCMV polypeptides may be modified using chemical methods or genetic engineering methods known in the art such as those described and referenced herein below under Modifications of Polynucleotides and Polypeptides.

Another embodiment is a method of identifying amino acids that specifically bind to at least one of HCMV pUL36, pUL37$_S$, pUL37$_M$, or pUL37$_L$. In addition, such HCMV polypeptides may be modified using chemical methods or genetic engineering methods known in the art such as those described and referenced herein below under Modifications of Polynucleotides and Polypeptides.

An embodiment is a method of identifying polynucleotides, including DNA and RNA, that specifically bind to at least one of HCMV polypeptides pUL36, pUL37$_S$, pUL37$_M$, or pUL37$_L$. In addition, such HCMV polypeptides may be modified using chemical methods or genetic engineering methods known in the art such as those described and referenced herein below under Modifications of Polynucleotides and Polypeptides.

An embodiment is a method of identifying nucleic acids (such as polynucleotides or nucleotides) that specifically bind to at least one of HCMV polypeptides pUL36, pUL37$_S$, pUL37$_M$, or pUL37$_L$. In addition, such HCMV polypeptides may be modified using chemical methods or genetic engineering methods known in the art such as those described and referenced herein below under Modifications of Polynucleotides and Polypeptides.

A preferred method of isolating a physiological molecule that specifically binds to a viral polypeptide having anti-apoptotic activity is by contacting the viral polypeptide in a cell extract to an affinity reagent, such as an antibody, that binds to the viral polypeptide, and isolating the resultant immune complexes. For example, at least one of HCMV polypeptides pUL36, pUL37$_S$, pUL37$_M$, or pUL37$_L$ can be contacted in a cell extract to an antibody that binds, respectively, to at least one of the HCMV polypeptides, and the resultant immune complexes isolated. Other molecules, such as derivatives of avidin or biotin, that bind to at least one of the HCMV polypeptides, may be used as an affinity tag. In addition, such HCMV polypeptides may be modified using chemical methods or genetic engineering methods known in the art such as those described and referenced herein below under Modifications of Polynucleotides and Polypeptides.

The isolated immune complexes may contain an accessory molecule, such as a polypeptide or polynucleotide, bound to the viral polypeptide having anti-apoptotic activity. The bound accessory molecule may be identified and isolated by its displacement from the immune complexes with either a denaturing agent or other standard methods (e.g., see *Current Protocols in Molecular Biology* on CD-ROM (1998) John Wiley & Sons, Inc., which is incorporated herein by reference). Other standard methods for freeing and isolating the bound accessory molecule include the use of a displacing reagent such as a solution of inorganic or organic electrolytes at low or high concentrations and at different pH values, or a chaotropic agent.

In the case where the physiological molecule is a polypeptide, preferably the denaturing agent is a reducing agent. The denatured and preferably reduced polypeptides can then be resolved electrophorectically on a polyacrylamide gel. The putative accessory polypeptides can be identified on the polyacrylamide gel by one or more of various well known methods (e.g., Coomassie staining, Western blotting, silver staining, etc.), and isolated by resection of a portion of the polyacrylamide gel containing the relevant identified polypeptide, and elution of the polypeptide from the gel portion.

As an example of freeing and isolating the accessory molecule, the inventors lysed and then treated cells that had continuously expressed pUL37$_S$myc (HeLa/UL37$_S$) with anti-myc antibody. The immunocomplexes were then collected with protein G agarose affinity beads and then analyzed by sodium dodecyl sulfate polyacrylamide gel electrophoresis (SDS-PAGE). Polypeptide bands on the gel were visualized by silver-stain. HeLa/pcDNA3 were used as a control. At least three polypeptide bands of the HeLa/UL37$_S$ immunocomplexes were visualized on the gel that were not present in the HeLa/pcDNA3 immunocomplexes. The apparent sizes of these three bands correspond to approximately 33-35 kDa, 115 kDa, and 145 kDa. The three polypeptides in these three bands could then be isolated from the polyacrylamide gel and their amino acid sequences (total or partial) determined by standard methods (e.g., see *Current Protocols in Molecular Biology* on CD-ROM 1998) Chapter 10, John Wiley & Sons, Inc., which is incorporated herein by reference).

A yeast double-transformation assay (Chien et al, 1991, which is incorporated by reference) can be used to identify accessory polypeptides that specifically bind to viral polypeptides having anti-apoptotic activity, under physiological conditions. For example, the double-transformation assay can be used to identify accessory polypeptides that specifically bind to at least one of HCMV polypeptides pUL36, pUL37$_S$, pUL37$_M$, or pUL37$_L$, under physiological conditions, forming an intermolecular polypeptide complex. In addition, such HCMV polypeptides may be modified using chemical methods or genetic engineering methods known in the art such as those described and referenced herein below under Modifications of Polynucleotides and Polypeptides.

In a preferred embodiment, the GAL4 fusion polypeptide comprises a HCMV polypeptide having anti-apoptotic activity, such as pUL36, pUL37$_S$, pUL37$_M$, and pUL37$_L$. In addition, such HCMV polypeptides having anti-apoptotic activity may be modified using chemical methods or genetic engineering methods known in the art such as those described and referenced herein below under Modifications of Polynucleotides and Polypeptides. The other GAL 4 fusion polypeptide comprises a polypeptide encoded by a cDNA that is a member of a library, for example, a human cDNA library.

Alternatively, an *E. coli*/BCCP interactive screening system (Germino et al. (1993) *Proc. Natl. Acad. Sci.* (*U.S.A.*) 90, 1639, which is incorporated herein by reference) can be used to identify the viral polypeptide binding sequences. Also, an expression library, such as the λgt11 cDNA expression library (Dunn et al., 1989, which is incorporated by reference), can be screened with a labeled viral anti-apoptotic polypeptide, such as HCMV polypeptide pUL36, pUL37$_S$, pUL37$_M$, and pUL37$_L$, to identify cDNAs encoding polypeptides that specifically bind to such a viral polypeptide. In addition, such viral polypeptides having anti-apoptotic activity may be modified using chemical methods or genetic engineering methods known in the art such as those described and referenced herein below under Modifications of Polynucleotides and Polypeptides.

For these procedures, cDNA libraries usually comprise eukaryotic cDNA populations, such as animal (including mammalian) cDNA populations, typically human, mouse, or rat and may represent cDNA produced from RNA and one cell type, tissue, or organ, and one or more developmental stages. Specific binding for screening cDNA expression libraries is usually provided by including one or more blocking agents (e.g., albumin, nonfat dry milk solids, etc.) prior to and/or concomitant with contacting the labeled viral anti-apoptotic polypeptide (and/or labeled antibody that recognizes such a viral polypeptide).

A putative accessory polypeptide may be identified as an accessory polypeptide by demonstration that the polypeptide binds to a viral polypeptide having anti-apoptotic activity. Examples of such viral polypeptides include HCMV polypeptides pUL36, pUL37$_S$, pUL37$_M$, and pUL37$_L$, and modified forms of such HCMV polypeptides. Such binding may be shown in vitro by various means, including, but not limited to, binding assays employing a putative accessory polypeptide that has been renatured subsequent to isolation by a polyacrylamide gel electrophoresis method.

Alternatively, binding assays employing a recombinant or chemically synthesized putative accessory polypeptide may be isolated and all or part of its amino acid sequence determined by chemical sequencing, such as Edman degradation. The amino acid sequence information may be used to chemically synthesize the putative accessory polypeptide. The amino acid sequence may also be used to produce a recombinant putative accessory polypeptide by: 1) isolating a cDNA clone encoding the putative accessory polypeptide by screening a cDNA library with degenerate oligonucleotide probes according to the amino acid sequence data, 2) expressing the cDNA in a host cell, and 3) isolating the putative accessory polypeptide.

Putative accessory polypeptides that bind viral anti-apoptotic polypeptides, such as HCMV polypeptides pUL36, pUL37$_S$, pUL37$_M$, and pUL37$_L$, or modified forms of the polypeptides, in vitro, are identified as accessory polypeptides. Accessory polypeptides may also be identified by cross-linking in vivo with bifunctional cross-linking reagents (e.g., dimethylsuberimidate, glutaraldehyde, etc.), wherein the subsequent isolation of the cross-linked products includes the viral anti-apoptotic polypeptide. For a general discussion of cross-linking, see Kunkel et al. (1998) *Mol. Cell. BioChem.* 34, 3, which is incorporated herein by reference. Preferably, the bifunctional cross-linking reagent will produce cross-links which may be reversed under specific conditions after isolation of the cross-linked complex so as to facilitate isolations of the accessory polypeptide from the viral anti-apoptotic polypeptide. Isolations of cross-linked complexes that include a viral anti-apoptotic polypeptide are preferably accomplished by binding an antibody that binds the viral polypeptide with an avidity of at least $1 \times 10^7$ M$^{-1}$ to a population of cross-linked complexes and recovering only those complexes that bind to the antibody with an avidity of at least $1 \times 10^7$ M$^{-1}$. Polypeptides that are cross-linked to a viral anti-apoptotic polypeptide, such as pUL36, pUL37$_S$, pUL37$_M$, and pUL37$_L$, are identified as accessory polypeptides.

Accordingly, screening assays can be developed for identifying candidate antiviral compounds that inhibit or diminish the specific binding of a viral anti-apoptotic polypeptide, such as pUL36, pUL37$_S$, pUL37$_M$, and pUL37$_L$, to an accessory polypeptide under suitable binding conditions. Such suitable binding conditions are readily determined by those of ordinary skill in the art.

Similarly, screening assays can be developed for identifying putative accessory polynucleotides, including accessory DNA and RNA, that bind to viral anti-apoptotic polypeptides, such as pUL36, pUL37$_S$, pUL37$_M$, and pUL37$_L$. These screening assays can be carried out using standard procedures and assays described, for example, in: Current Protocols in Molecular Biology, John Wiley & Sons, Inc., 1995, F. M. Ausubel et al., Eds., which is incorporated herein by reference. Moreover, such protein-DNA or protein-RNA interactions can be characterized, and the isolation of the specific polynucleotides that interact with the anti-apoptotic polypeptides can be performed using standard procedures and assays as described, for example, in: T. D. Levine et al., Mol. Cell. Biol. 13, 3494-3504, 1993; and L. M. Dember et al., J. Biol. Chem. 271, 2783-2788, 1996; each of which is incorporated herein by reference.

Methods of Inhibiting, Diminishing or Modulating the Expression of a Polynucleotide Encoding a Polypeptide Having Anti-Apoptotic Activity, Using an Antisense Oligonucleotide Additional embodiments directed to interfering with the expression of viral polynucleotides encoding polypeptides having anti-apoptotic activity, for example UL36 and UL37, include methods that employ specific antisense polynucleotides complementary to all or part of the sequences encoding the anti-apoptotic polypeptide, such as pUL36, pUL37$_S$, pUL37$_M$, and pUL37$_L$. Such complementary antisense polynucleotides may include nucleotide substitutions, additions, deletions, or transpositions, so long as specific hybridization to the relevant target sequence corresponding to the sequences encoding the viral anti-apoptotic polypeptide is retained as a functional property of the polynucleotide. Complementary antisense polynucleotides include soluble antisense DNA or RNA oligonucleotides that can hybridize specifically to the viral RNA species and prevent or diminish transcription of the viral RNA species and/or translation of the encoded polypeptide (Ching et al., 1989; Loreau et al. (1990); Broder et al., 1990; Holcenberg et al. WO 91/11535; U.S. Ser. No. 07/530,165; WO91/09865; WO91/04753; WO90/13641; and EP386563; each of which is incorporated herein by reference).

The antisense polynucleotides therefore inhibit or diminish production of polypeptides having anti-apoptotic activity, such as pUL36, pUL37$_S$, pUL37$_M$, and pUL37$_L$. Antisense polynucleotides that prevent transcription and/or translation of RNA corresponding to the anti-apoptotic polypeptides may inhibit or diminish anti-apoptotic activity and, thereby, induce or restore apoptosis. Antisense polynucleotides of various lengths may be produced, although such antisense polynucleotides typically comprise a sequence of approximately at least 25 consecutive nucleotides that are substantially identical to a naturally-occurring viral polynucleotide sequence encoding an anti-apoptotic polypeptide, such as the sequences of UL36 and UL37.

Antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific RNA species. In some embodiments the antisense polynucleotides comprise methylphosphonate moieties. For general methods relating to antisense polynucleotides, see *Antisense RNA and DNA* (1988), D. A. Melton, Ed., Cold Spring Harbor Laboratory, Cold Spring Harbor, N.Y.

Retroviral vectors expressing a portion of the UL36 or UL37 genes in the anti-sense orientation can be constructed and used to infect one portion of a cell population, e.g., MRC-5 cells. As a control, a similar retroviral vector containing an irrelevant DNA insert (i.e., any DNA insert that is not homologous to the HCMV UL36 or UL37 polynucleotide sequences and does not up- or down-regulate production of UL36 or UL37 mRNAs) can be used to infect a second portion of the same cell population. The cell populations can then be selected in the presence of a selection agent, e.g., G418. Cells surviving the selection, e.g., G418-resistant cells, have been successfully infected, indicating that the vector DNA was integrated into the genome of the cells. These cells are then exposed to virus, having anti-apoptotic activity, and tested for the development of apoptosis. The testing can be performed by any of the methods described for detecting cell death and/or apoptosis (for example, those reviewed in Sellers, J. R., Cook, S., and Goldmacher, V. S. (1994) *J. Immunol. Meth.* 172, 255-264 and references cited therein; Telford, W. G., King, L. E., and Fraker, P. J. (1994) *J. Immunol. Meth.* 172, 1-16 and references cited therein; Poirier, J., Ed. (1997) *Apoptosis Techniques and Protocols*, Humana Press, Totowa, N.J.; each of which is incorporated herein by reference): 1) by examining the extent of DNA degradation; and 2) by detecting the cell surface expression of phosphatidylserine.

Methods of Screening for and Identifying Compounds that Inhibit, Diminish or Modulate the Specific Binding of a Physiological Molecule to Polypeptides Having Anti-Apoptotic Activity A basis of the present invention is the finding that anti-apoptotic polypeptides, such as pUL36, pUL37$_S$, pUL37$_M$, and pUL37$_L$, can form a complex, under physiological conditions, with cellular polypeptides involved in the apoptosis signaling pathway. This finding indicates that the viral anti-apoptotic polypeptide can function as a modulator of apoptosis through such intermolecular interactions. Such functional modulation can serve to couple a signal transduction pathway, via the viral anti-apoptotic polypeptide, to an apoptosis regulatory polypeptide (e.g., FADD, FLICE (caspase 8), caspase 3, Apaf-1, Bcl-x$_L$, Bcl-2, Bak, ICE, Bax, BNIP-3, and ANT) or other physiological molecule (e.g., polynucleotide recognized by the anti-apoptotic polypeptide) and, thereby, permit the viral polypeptide to regulate or modulate apoptosis, e.g., inhibit or diminish apoptosis.

Assays for detecting the ability of antiviral compounds to inhibit or diminish the binding of anti-apoptotic polypeptides to physiological molecules involved in the apoptosis signaling pathway, such as FADD, FLICE (caspase 8), caspase 3, Apaf-1, Bcl-x$_L$, Bcl-2, Bak, ICE, Bax, BNIP-3, and ANT, provide for facile high-throughput screening of agent banks (e.g., compound libraries, peptide libraries, and the like) to identify antagonists or agonists to the viral anti-apoptotic polypeptide or a physiological molecule that interacts with the viral polypeptide (e.g., FADD, FLICE (caspase 8), caspase 3, Apaf-1, Bcl-x$_L$, Bcl-2, Bak, ICE, Bax, BNIP-3, and ANT, or polynucleotides recognized by the viral polypeptide). Such antagonists and agonists may interfere with the anti-apoptotic activity of the viral polypeptides and, thereby, regulate or modulate apoptosis, e.g., induce or restore apoptosis in virally-infected cells and prevent viral replication. Thus, such compounds are useful in the treatment of viral diseases, and such methods are useful for screening for antiviral compounds, and may comprise, e.g., polypeptide, polynucleotide, amino acid, nucleotide, and chemical compounds.

Administration of an efficacious dose of a compound capable of specifically inhibiting or diminishing complex formation between the anti-apoptotic polypeptide and physiological molecule, (i.e., the intermolecular interaction or binding between the viral anti-apoptotic polypeptide and a physiological molecule involved in the apoptosis signaling pathway) to a patient can be used as a therapeutic or prophylactic method for treating pathological conditions (e.g., HCMV mononucleosis; congenital HCMV infection which may cause fetus abnormalities; HCMV infection in the immunocompromised host, such as AIDS patients, bone marrow transplant recipients, organ transplant recipients which frequently results in HCMV hepatitis; HCMV pneumonitis; HCMV esophagitis; HCMV colitis; HCMV retinitis; HCMV disseminated disease, which is often fatal) which are effectively treated by interfering with anti-apoptotic activity, e.g., inhibiting or diminishing anti-apoptotic activity and, thereby, inducing or restoring apoptosis and preventing viral replication.

In vitro polypeptide binding assays generally take one of two forms: immobilized anti-apoptotic polypeptides can be used to bind to labeled physiological molecule, e.g., a cellular polypeptide, or conversely, the immobilized physiological molecule, e.g., a cellular polypeptide, can be used to bind labeled anti-apoptotic polypeptides. In addition to these examples, there are many other types of binding assays, including the detection of the binding of two unlabeled molecules (e.g., polypeptides) using Biacore technology (Biacore Inc., Piscataway, N.J.), or disruption of binding of two molecules (e.g., polypeptides) with a third molecule (e.g., a polypeptide) which competes with binding to one of the first two molecules (e.g., polypeptides).

Typically, a labeled polypeptide is contacted with an immobilized polypeptide under aqueous binding conditions and the extent of binding is determined by measuring the amount of immobilized labeled polypeptide. In each case, the labeled polypeptide is contacted with the immobilized polypeptide under aqueous conditions that permit specific binding of the polypeptides to form a specific intermolecular complex, in the absence of added agent. Particular aqueous conditions may be selected by the practitioner according to conventional methods. For general guidance, the following buffered aqueous conditions may be used: 10-250 mM NaCl, 5-50 mM Tris HCl, pH 5-8, with optional addition of divalent cation(s) and/or metal chelators and/or nonionic detergents and/or membrane fractions. It is appreciated by those of ordinary skill in the art that additions, deletions, modifications (such as pH) and substitutions (such as KCl substituting for NaCl or buffer substitution) may be made to these basic conditions. Modifications can be made to the basic binding reaction conditions so long as specific binding of anti-apoptotic polypeptides to physiological molecules, e.g., cellular polypeptides, occurs in the control reaction(s). Conditions that do not permit specific binding in control reactions (no agent included) are not suitable for use in binding assays.

Preferably, at least one polypeptide species is labeled with a detectable marker. Suitable labeling includes, but is not limited to, radiolabeling by incorporation of a radiolabeled amino acid (e.g., $^{14}$C-labeled leucine, $^{3}$H-labeled glycine, $^{35}$S-labeled methionine), radiolabeling by post-translational radioiodination with $^{125}$I or $^{131}$I, (e.g., Bolton-Hunter reaction and chloramine T), labeling by post-translational phosphorylation with $^{32}$P (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker.

Additionally, in some embodiments an anti-apoptotic polypeptide may be used in combination with an accessory polypeptide (e.g., a cellular polypeptide which forms a complex with the anti-apoptotic polypeptide, in vivo). In this case it is preferred that different labels are used for each polypeptide species, so that binding of individual and/or heterodimeric and/or multimeric complexes can be distinguished. For example, but not for limitation, an anti-apoptotic polypeptide, such as pUL36, pUL37$_S$, pUL37$_M$, or pUL37$_L$, may be labeled with fluorescein and an accessory polypeptide, such as FADD, FLICE (caspase 8), caspase 3, Apaf-1, Bcl-x$_L$, Bcl-2, Bak, ICE, Bax, BNIP-3, and ANT, may be labeled with a fluorescent marker that fluoresces with either a different excitation wavelength or emission wavelength, or both. Alternatively, double-label scintillation counting may be used, wherein an anti-apoptotic polypeptide is labeled with one isotope (e.g., $^{3}$H) and a second polypeptide species (e.g., FADD, FLICE (caspase 8), caspase 3, Apaf-1, Bcl-x$_L$, Bcl-2, Bak, ICE, Bax, BNIP-3, and ANT) is labeled with a different isotope (e.g., $^{14}$C) that can be distinguished by scintillation counting using discrimination techniques.

Labeled polypeptide(s) are contacted with immobilized polypeptide(s) under aqueous conditions, e.g., as described here, in this section. The time and temperature of incubation of a binding reaction may be varied, so long as the selected conditions permit specific binding to occur in a control reaction where no agent is present. Preferable embodiments employ a reaction temperature of about at least 15 degrees Centigrade, more preferably about 35 to 42 degrees Centigrade, and a time of incubation of approximately at least 15 seconds, although longer incubation periods are preferable so that, in some embodiments, a binding equilibrium is attained. Binding kinetics and the thermodynamic stability of heterodimer complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other methods (Creighton, Ed. (1984) *Proteins, Structures and Molecular Principles*, W.H. Freeman and Company, N.Y.).

Specific binding of the labeled polypeptide (e.g., FADD, FLICE (caspase 8), caspase 3, Apaf-1, Bcl-x$_L$, Bcl-2, Bak, ICE, Bax, BNIP-3, and ANT) to the immobilized polypeptide (e.g., an anti-apoptotic polypeptide), is determined by including unlabeled competitor polypeptide(s) (e.g., albumin). After a binding reaction is completed, labeled polypeptide(s) that is/are specifically bound to immobilized polypeptide is detected. For example and not for limitation, after a suitable incubation period for binding, the aqueous phase containing non-immobilized polypeptide is removed and the substrate containing the immobilized polypeptide species and any labeled polypeptide bound to it is washed with a suitable buffer (optionally containing unlabeled blocking agents), and the wash buffer(s) removed. After washing, the amount of detectable label remaining specifically bound to the immobilized polypeptide is determined (e.g., by optical, enzymatic, autoradiographic, or other radiochemical means).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays. However, reaction conditions are selected so as to permit specific binding between an anti-apoptotic polypeptide and a physiological molecule in a control binding reaction. Blocking agents are included to inhibit nonspecific binding of labeled protein to immobilized polypeptide and/or to inhibit nonspecific binding of labeled polypeptide to the immobilization substrate.

In embodiments where a polypeptide is immobilized, covalent or noncovalent linkage to a substrate may be used. Covalent linkage chemistries include, but are not limited to, well-characterized methods known in the art (Kadonaga and Tijan, 1986). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of polypeptides to a substrate includes, but is not limited to, bonding of the polypeptide to a charged surface and binding with specific antibodies.

In one class of embodiments, parallel binding reactions are conducted, wherein one set of reactions serves as control and at least one other set of reactions includes various quantities of agents, mixtures of agents, or biological extracts, that are being tested for the capacity to inhibit or diminish binding of an anti-apoptotic polypeptide to a cellular polypeptide.

A preferred embodiment is a method of identifying antiviral compounds that inhibit or diminish the specific binding of a physiological molecule to an HCMV polypeptide having anti-apoptotic activity, using an in vitro binding assay.

Another preferred embodiment is a method of identifying antiviral compounds that diminish the specific binding of a physiological molecule to at least one of pUL36, pUL37$_S$, pUL37$_M$, or pUL37$_L$, using an in vitro binding assay. Such physiological molecules comprise polypeptide, polynucleotide (DNA and/or RNA), amino acid, and/or nucleotide molecules.

Another preferred embodiment is a method of identifying antiviral compounds that diminish the specific binding of a cellular polypeptide, involved in the apoptosis signaling pathway, to at least one of pUL36, pUL37$_S$, pUL37$_M$, or pUL37$_L$, using an in vitro binding assay.

Another preferred embodiment is a method of identifying antiviral compounds that diminish the specific binding of FADD, FLICE (caspase 8), caspase 3, Apaf-1, Bcl-x$_L$, Bcl-2, Bak, ICE, Bax, BNIP-3, and ANT, to at least one of pUL36, pUL37$_S$, pUL37$_M$, or pUL37$_L$, using an in vitro binding assay.

Another preferred embodiment is a method of identifying antiviral compounds that diminish the specific binding of a cellular polynucleotide, such as a cellular DNA or RNA, to at least one of pUL36, pUL37$_S$, pUL37$_M$, or pUL37$_L$, using an in vitro binding assay.

Screening assays can be developed for identifying antiviral compounds (e.g., polypeptides such as non-functional forms of anti-apoptotic polypeptides, and monoclonal and/or polyclonal antibodies), polynucleotide (DNA and/or RNA), amino acid, and/or nucleotide compounds, including analogs and/or modified forms of such compounds, and/or including synthetic and/or chemical compounds) that diminish the specific binding of a physiological molecule (e.g., a polypeptide, polynucleotide, amino acid, and/or nucleotide) to a viral anti-apoptotic polypeptide, such as pUL36, pUL37$_S$, pUL37$_M$, and/or pUL37$_L$. These screening assays can be carried out using standard procedures and assays described, for example, in: Ausubel et al., Eds. (1995) *Current Protocols in Molecular Biology*, John Wiley & Sons, Inc., which is incorporated herein by reference.

Numerous biochemical assays have been developed to screen for molecules that disrupt specific polypeptide interactions (e.g., interactions of viral polypeptides having anti-apoptotic activity) with physiological molecules (e.g., polypeptides, polynucleotides, amino acids, and/or nucleotides). Some of these assays are designed to be conducted in a multiwell plate format (e.g., a 96-well plate) and utilize the enzyme-linked immunosorbent assay (ELISA) for quantitation. For example, in one assay, 96-well microtiter plates are coated with an avidin derivative to which a biotinylated molecule (e.g., comprising a physiological molecule) is bound. A GST- or His$_6$-fusion polypeptide (e.g., comprising a viral polypeptide having anti-apoptotic activity that can interact with the biotinylated molecule) is added in the presence or absence of test compounds (i.e., candidate antiviral compounds). The plates are incubated to allow binding and then unbound GST-fusion or His$_6$-fusion polypeptide is removed by washing. The amount of the fusion polypeptide specifically bound to the tethered molecule is determined by an ELISA using an anti-GST antibody or a poly-his-binding reagent conjugated to horseradish peroxidase. Compounds which block the interaction between the biotinylated molecule and the fusion polypeptide cause a decrease in the ELISA signal. Thus, a decrease in the ELISA signal is indicative of a diminution in the binding of the physiological molecule to the viral polypeptide having anti-apoptotic activity.

Moreover, the diminution of such binding activity by a putative antiviral compound can be characterized, and the isolation of such an antiviral compound can be performed using standard procedures and assays as described, for example, in: T. D. Levine et al., Mol. Cell. Biol. 13, 3494-3504, 1993; and L. M. Dember et al., *J. Biol. Chem.* 271, 2783-2788, 1996; each of which is incorporated herein by reference.

Methods of Screening for and Identifying Compounds that Specifically Bind to Polypeptides Having Anti-Apoptotic Activity, in an In Vitro Binding Assay Antiviral compounds such as: polypeptide (e.g., monoclonal and/or polyclonal antibodies), polynucleotide (e.g., DNA and/or RNA), amino acid, and/or nucleotide compounds; analogs and/or modified forms of such compounds; and/or synthetic and/or chemical compounds; that specifically bind to viral polypeptides having anti-apoptotic activity, may interfere with the anti-apoptotic function of the viral polypeptides and thereby lead to the induction of apoptosis, inhibiting, or diminishing viral replication. Such antiviral compounds may be identified in the same manner as described above for the identification of accessory polypeptides or polynucleotides that bind specifically to such viral polypeptides. In addition, such antiviral compounds may be identified by using the ELISA-based assay described above.

As an example, 96-well microtiter plates can be coated with an avidin derivative to which a biotinylated molecule (e.g., comprising a test compound) is bound. A GST- or His$_6$-fusion polypeptide (e.g., comprising a viral polypeptide having anti-apoptotic activity) is then added to the plates. The plates are incubated to allow binding and then unbound GST-fusion or His$_6$-fusion polypeptide is removed by washing. The amount of the fusion polypeptide specifically bound to the tethered molecule is determined by an ELISA using an anti-GST antibody or a poly-HIS-binding reagent conjugated to horseradish peroxidase. There is an increase the ELISA signal when the fusion polypeptide is bound to the tethered molecule. Thus, an increase in the ELISA signal is indicative of the binding of the test molecule to the viral polypeptide having anti-apoptotic activity.

Moreover, the binding activity of the putative antiviral compound can be characterized, and the isolation of such an antiviral compound can be performed using standard procedures and assays as described, for example, in: T. D. Levine et al., Mol. Cell. Biol. 13, 3494-3504, 1993; and L. M. Dember et al., J. Biol. Chem. 271, 2783-2788, 1996; each of which is incorporated herein by reference.

A preferred embodiment is a method of identifying antiviral compounds that specifically bind to HCMV polypeptides having anti-apoptotic activity, or modified forms of such polypeptides, using an in vitro binding assay.

Another preferred embodiment is a method of identifying antiviral compounds that specifically bind to HCMV polypeptides pUL36, $pUL37_S$, $pUL37_M$, and $pUL37_L$, or modified forms of such polypeptides, using an in vitro binding assay.

Suitable candidate antiviral compounds may be identified by screening of various commercially available synthetic or semi-synthetic and natural libraries which are widely available, or by rational drug design based on polypeptide sequence homologies, X-ray structures or any standard methods that identify molecules that are likely to bind to the viral polypeptide having anti-apoptotic activity based on the analysis of the structures of the polypeptide and the compound. For further details and references see below Methods in Rational Drug Design.

Methods of Screening for and Identifying Compounds that Specifically Bind to Polypeptides Having Anti-Apoptotic Activity in a Double-Transformation Assay The double-transformation assay is also called the "Two-Hybrid System," and permits the rapid screening of a large number of cellular polypeptides for the identification and isolation of polypeptides that bind specifically to a known polypeptide of interest, in vivo (S. Fields and O. K. Song, 1989, which is incorporated herein by reference). Further, the assay has been widely used in the study of intermolecular polypeptide interactions in cells. The assay merely relies on the ability of two polypeptides to bind to each other and is not reliant on detailed or specific knowledge of the polypeptide structure, function, or sequence identity. This intermolecular polypeptide interaction results in the reconstitution of a transcriptional activator and the induction of a reporter gene product, which is easily detected by standard, routine assays. The double-transformation assay not only permits the identification, but also the isolation of polypeptides that specifically interact with and bind to a known polypeptide of interest, such as pUL36, $pUL37_S$, $pUL37_M$, and $pUL37_L$, in a particular cell type, such as B cells.

Detection of the binding of a candidate polypeptide with a known polypeptide is dependent on the restoration of a transcriptional activator, such as yeast GAL4. Many transcriptional activators, such as yeast GAL4, consist of two functional domains; a DNA-binding domain and an activation domain. The pool of polynucleotide molecules encoding polynucleotides that may potentially interact with the known polypeptide, and the polynucleotide encoding the known polypeptide itself, are inserted into separate vectors. One vector encodes the DNA-binding domain such that an inserted polynucleotide molecule is expressed as a hybrid polypeptide containing the DNA-binding domain. Whereas, another vector encodes the activation domain such that an inserted polynucleotide molecule is expressed as a hybrid polypeptide containing the activation domain.

As a preferred embodiment, an HCMV polynucleotide encoding at least one of pUL36, $pUL37_S$, $pUL37_M$, or $pUL37_L$, is inserted into a vector containing the DNA-binding domain, whereas, the pool of polynucleotide molecules encoding polypeptides that may potentially bind to at least one of pUL36, $pUL37_S$, $pUL37_M$, or $pUL37_L$ (HCMV polypeptides), are inserted into a vector containing the activation domain (candidate polypeptides). Thus, the HCMV hybrid polypeptide contains the DNA-binding domain and the candidate hybrid polypeptides contain the activation domain. Consequently, under these conditions, when a candidate polypeptide binds to at least one of the HCMV polypeptides, the two hybrid polypeptides combine to reconstitute a functional GAL4 transcriptional activator that induces the expression of a reporter gene fused to a GAL4 binding site and carried in the host yeast strain. Such positive candidate polypeptides, that bind to at least one of the HCMV polypeptides, are then detected by assaying for expression of the reporter gene.

Using the double-transformation assay, positives can be easily identified and distinguished from negatives and, thus, a large number of polypeptides can be readily screened. The product of the reporter gene is easily detected by employing a variety of standard and routine assays, some including color indicators. An example of a reporter gene is lacZ. Consequently, when a HCMV-binding polypeptide binds to the viral polypeptide, to reconstitute a functional GAL4 transcriptional activator, this specific polypeptide interaction induces the expression of the lacZ reporter gene. The product of lacZ expression, β-galactosidase, is then detected by the addition of the reagent X-gal which turns the yeast cell blue in color. Thus, a positive blue yeast cell, containing a candidate polypeptide that binds to at least one of the HCMV polypeptides, is easily identified and distinguished from a background of white yeast cells that do not contain polypeptides that bind to the HCMV polypeptides.

Further, kits for performing the double-transformation assays are commercially available. The commercially available kits include all the necessary reagents, strains, and instructions for carrying out such reactions, and come complete with instructions and standardized conditions for carrying out the assay in a step-wise manner. For example, Clontech has been marketing kits containing all the necessary reagents and strains since 1993 (Clontech, 1993/1994 Catalog). In addition, many laboratory manuals include the necessary protocols for transformation and expression.

The transformation and expression of a large number of polynucleotides is routine and requires only standard procedures. Further, it is entirely feasible to screen a large number of polypeptides, expressed from a large number of polynucleotides, for a specific activity, e.g., binding to HCMV polypeptides having anti-apoptotic activity. Such screening, identification, and isolation of polypeptides with the desired activity, can be accomplished using routine experimentation.

Further, in order to identify the polypeptides of a particular cell type, e.g., B-cell, that interact specifically with a known polypeptide, e.g., pUL36, $pUL37_S$, $pUL37_M$, and $pUL37_L$, a cDNA library made from RNA of that particular cell type can be used. Such libraries, and kits for preparing such libraries, are also readily available from commercial sources.

For commercial libraries, the complexity is typically in the range of $1\text{-}5\times10^6$ (Clontech, 1993/1994 Catalog). For example, see pages 18-33 of the 1993/1994 Clontech Catalog. In order to adequately cover this range of complexity, about $10^6$ transformants should be generated. The generation of $10^6$ transformants is easily achieved, since the typical frequency of double transformation of yeast is within the range of $10^3$ to $10^4$ transformants per 1 µg of plasmid DNA. Consequently, under these conditions, in order to screen $1\text{-}5\times10^6$ cDNA clones, only 100-500 µg of plasmid DNA is needed.

A preferred embodiment, is a method of identifying novel antiviral compounds that specifically bind to HCMV polypeptides having anti-apoptotic activity in a double-transformation assay.

Another preferred embodiment, is a method of identifying novel antiviral compounds that specifically bind to HCMV polypeptides pUL36, $pUL37_S$, $pUL37_M$, and $pUL37_L$ in a double-transformation assay.

Methods of Screening for and Identifying Compounds that Restore, Induce, or Modulate Apoptosis and/or Inhibit, Diminish, or Modulate Anti-apoptotic Activity, in Cells As a preferred embodiment, a candidate antiviral compound can be screened for its ability to restore, induce, or modulate apoptosis (detected with any marker of apoptosis) in any HCMV-infected cell line, and/or inhibit, diminish, or modulate anti-apoptotic activity in such HCMV-infected cell lines. Such antiviral compounds can be screened in an animal cell, including human or other mammalian cell, or any other eukaryotic cell, including yeast, that expresses either $pUL37_S$ or pUL36 or another polypeptide that has a sequence motif or a similar functional domain, or a similar function. The cells expressing such polypeptides would then be treated with the candidate antiviral compound and challenged with: 1) an anti-Fas antibody, Fas-ligand, or TNF-α, in the presence or absence of CHX; or 2) any other agent that activates the caspase signaling apoptotic pathway and; consequently, the restoration, induction. or modulation of apoptosis activity and/or the inhibition, diminution, and/or modulation of anti-apoptotic activity is assayed for.

As another preferred embodiment, a candidate antiviral compound may be screened for its ability to inhibit or diminish the interaction of $pUL37_S$, pUL36, or any other polypeptide having an anti-apoptotic function or motif, with FADD, FLICE (caspase 8), caspase 3, Apaf-1, $Bcl\text{-}x_L$, Bcl-2, Bak, ICE, Bax, BNIP-3, and ANT, or any other polypeptide having an apoptotic function or motif. Screening for such interaction, e.g., intermolecular polypeptide interaction, may be performed using a variety of standard screening protocols including immuno-assays, double-transformation assays, assays inhibiting enzymatic activity of any caspase or a related enzyme, or any other protein binding assay described herein.

Suitable candidate antiviral compounds may be identified by screening of various commercially available synthetic, semi-synthetic, and/or natural libraries which are widely available, or by rational drug design based on polypeptide sequence homologies, X-ray structures or any standard methods that identify molecules that are likely to bind to the viral polypeptide having anti-apoptotic activity based on the analysis of the structures of the polypeptide and the compound. For further details and references see below Methods in Rational Drug Design.

Pharmaceutical Compositions

Pharmaceutical compositions containing a therapeutically effective amount of the therapeutic compounds are useful for treating patients suffering from degenerative disorders or diseases characterized by inappropriate cell death or inappropriate cell proliferation, or aberrant or disregulated apoptosis. Pharmaceutical compositions according to the invention thus will contain a therapeutically effective amount of the present therapeutic compounds and may optionally contain one or more pharmaceutically acceptable carriers and/or excipients, known to those of ordinary skill in the art. Delivery, dosage and frequency, and length of the course of treatment can be readily optimized for a particular patient by one of ordinary skill in the art. For example, the present pharmaceutical composition can be formulated as sterile aqueous or nonaqueous suspensions or emulsions, as described above, for example for solutions for intravenous administration.

The quantities of reagents determined to be an effective amount for treatment will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al., Eds. (1990) *Goodman and Gilman's: The Pharmacological Bases of Therapeutics*, 8th Ed., Pergamon Press; and *Remington's Pharmaceutical Sciences*, 17th Ed. (1990), Mack Publishing Co., Easton, Pa. Methods for administration are also discussed therein, e.g., for oral, intravenous, intraperitoneal, or intramuscular administration, transdermal diffusion, and others.

If the pharmaceutical composition is formulated for oral delivery and contains a peptide or peptide-like compound as the active agent, then the formulation must include a means for protecting the agent from the proteolytic enzymes of the digestive system. Typically, the agent is encased in a liposome structure or chemically derivatized so that the enzymes are prevented from cleaving the amide bonds of the peptide, resulting in the agent's degradation.

The pharmaceutical compositions can be administered by intravenous, parenteral, intraperitoneal, intramuscular, oral, or local administration, such as by aerosol or transdermally, for therapeutic treatment, or delivered by the means of contact discussed below under "Therapeutic Applications." The pharmaceutical compositions can be administered in a variety of unit dosage forms depending upon the method of administration. For example, unit dosage forms suitable for oral administration include powder, tablets, pills, capsules and dragees.

The pharmaceutical compositions will often be administered intravenously. Thus, this invention provides compositions for intravenous administration which comprise a solution of the polypeptide dissolved or suspended in an acceptable carrier, preferably an aqueous carrier. Slow release formulations, or slow release delivery vehicles will often be utilized for continuous administration. "Pharmaceutically acceptable carriers" will include water, saline, buffers, and other compounds described, e.g., in the Merck Index, Merck & Co., Rahway, N.J. These compositions will sometimes be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, preferably about 20% (see, *Remington's Pharmaceutical Sciences,* 17th Ed., 1990).

The compositions containing the compounds can be administered for prophylactic and/or therapeutic treatments. In therapeutic applications, compositions are administered to a patient already suffering from a degenerative disorder or disease, as described below under "Therapeutic Applications," in an amount sufficient to cure or at least alleviate the symptoms of the degenerative disorder or disease and its complications. An amount adequate to accomplish this is defined as "therapeutically effective dose." Amounts effective for this use will depend on the severity of the disease and the weight and general state of the patient, and can be determined by one of ordinary skill in the art.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight, and can be determined by one of ordinary skill in the art.

Therapeutic Applications: Methods of Treating Cells Using Compounds that Regulate or Modulate Apoptosis or Anti-Apoptotic Activity Programmed cell death is a process in which cells undergo nuclear condensation and fragmentation during normal development of healthy tissues and organs. The process is essential in maintaining the balance between growth of new cells and elimination of old cells. When apoptosis does not work properly, either by causing cells to die prematurely or by preventing them from dying when scheduled, various disorders develop.

The present therapeutic compounds are useful for treating degenerative disorders and diseases characterized by inappropriate cell death or inappropriate cell proliferation, or aberrant or disregulated apoptosis. Particular disorders may involve different cell types whereby it may be desirable to restore or induce apoptosis in one cell type while inhibiting or diminishing apoptosis in the other. For example, it may be desirable to inhibit or diminish apoptosis in lung tissue cells in a patient suffering from acute lung injury by delivering a therapeutic compound of the invention, such as a polypeptide having anti-apoptotic activity (or by effecting expression of such a polypeptide in those cells) while inducing apoptosis in fibroblast cells which may be present in the lung due to the inflammatory response by delivering another therapeutic compound of the invention such as a compound that inhibits and diminishes anti-apoptotic activity.

Moreover, the therapeutic compound can be delivered alone, in combination with or during the course of treatment with other acceptable therapies known in the art for treating a particular disorder. For example, the present therapeutic compounds can be delivered to restore or induce apoptosis in a cancer patient who is also undergoing classic cancer therapy including, for example, radiation therapy, chemotherapy, and treatment with anti-cancer drugs including, for example, topoisomerase inhibitors, alkylating agents, antimetabolites, and hormone antagonists. Further, the present therapeutic compounds can also be delivered concurrently with gene therapy. For example, the present therapeutic compounds can be administered to a patient suffering from a degenerative disorder or disease of the central nervous system while the patient is concurrently undergoing gene therapy to replenish neutrophic hormones.

Premature widespread apoptosis (inappropriate cell death) causes much of the damage associated with degenerative disorders or diseases including, for example, AIDs, chemotherapy and radiation, and tissue atrophy. In AIDs patients, lymphocytes are activated even in the asymptomatic phase of the HIV infection, and those cells die prematurely by apoptosis. Such disorders may be treated by delivery of compounds of the invention that inhibit or diminish apoptosis, such as polypeptides having anti-apoptotic activity or polynucleotides encoding such polypeptides.

Those of ordinary skill in the art will appreciate that delivery of the various polypeptides having anti-apoptotic activity, or polynucleotides encoding such polypeptides, of the invention to particular target cells or tissues, as described herein, is intended to comprehend the delivery of the polypeptides themselves as well as the expression by the target cells or tissues of the polynucleotide sequences encoding those polypeptides by various known means and in accordance with the teachings of the present specification.

Degenerative disorders and diseases characterized by inappropriate cell proliferation, or aberrant or disregulated apoptosis, include cancer, autoimmune disorders, tissue hypertrophy, and inflammatory disorders including inflammation arising from acute tissue injury including, for example, acute lung injury. These disorders can be treated by delivering the compounds of the present invention that inhibit, diminish, or modulate anti-apoptotic activity.

Cancers arise when changes in DNA cause the anomalous accumulation of cells. The comparative rates of cell division and cell deaths determine how fast a cancer grows. Some cancer cells divide more slowly than normal cells, but the cancer may still expand because of prolonged cell life span. Apoptosis is an efficient method for preventing malignant transformation because it removes cells with genetic lesions. Defective apoptosis can promote cancer development, both by allowing accumulation of dividing cells and by obstructing removal of genetic variants with enhanced malignant potential. The present therapeutic compounds, including polypeptides having anti-apoptotic activity, or polynucleotides encoding such polypeptides, can be delivered to cancer patients to restore, induce, or modulate apoptosis.

Many types of cancer can be treated by delivering the present therapeutic compounds of the present invention, including for example, carcinomas, sarcomas, and leukemia/lymphomas, including for example, carcinomas such as adenocarcinomas, squamous carcinomas, carcinoma of the organs including breast, colon, head, neck, etc.; sarcomas including chondrosarcoma, melanosarcoma, etc.; and leukemia and lymphomas including acute lymphomatic leukemia, acute myelogenous leukemia, non-Hodgkin's lymphoma, Burkitt's lymphoma, B-cell lymphomas, T-cell lymphomas, etc. Other conditions amenable to treatment using the present therapeutic compounds include fungal infections.

The present therapeutic compounds can be used to treat autoimmune diseases. Random gene recombination and somatic hypermutation can potentially generate autoreactive T and B lymphocytes throughout life. Under normal conditions immature lymphocytes that bind autoantigens die by apoptosis. However, a defect in the deletion of these lymphocytes predisposes one to autoimmunity.

The present therapeutic compounds can be delivered to patients suffering from autoimmune disorders to restore or induce apoptosis in autoreactive T lymphocytes, for example, in patients suffering from systemic lupus erythematosus.

Other autoimmune diseases amenable to treatment by inhibiting or diminishing, or restoring or inducing apoptosis, through the administration of the present therapeutic compounds include, for example, rheumatoid arthritis, myasthenia gravis, Grave's disease, Hashimoto's thyroiditis, insulin-resistant diabetes, allergic rhinitis, asthma, functional autonomic abnormalities, juvenile insulin-dependent diabetes, Addison's disease, idiopathic hypoparathyroidism, spontaneous infertility, premature ovarian failure, pemphigus, Bullous pemphigoid, primary biliary cirrhosis, autoimmune hemolytic anemia, idiopathic thrombocytopenic purpura, idiopathic neutropenia, Goodpasture's syndrome, rheumatoid arthritis and Sjogren's syndrome.

The present therapeutic compounds can be used to treat inflammation resulting from acute lung injury, by restoring or inducing apoptosis. The disease process begins with an explosive inflammatory response in the alveolar wall. In the aftermath of the resulting tissue destruction, extensive fibroproliferation of the alveolar air space ensues, consisting of fibroblasts, capillaries and their connective tissue products (Fukuda, Y., et al., 1987). An important mechanism for the systematic elimination of the foregoing is apoptosis, i.e., programmed cell death.

The present therapeutic compounds can also be used to treat degenerative disorders or diseases due to premature or excessive cell loss during aging which can lead to organ dysfunction and disease. Such degenerative disorders and diseases include degenerative diseases of the central nervous system due to aging or other factors which result in the death of neurons. The present therapeutic compounds, e.g., the polypeptide having anti-apoptotic activity, or the polynucleotide encoding such a polypeptide, can be delivered to a patient suffering from such a degenerative disease to inhibit or diminish apoptosis. Further, the present therapeutic compounds can be delivered concurrently with gene therapy to provide genes encoding neutrophic hormones including, for example, nerve growth factor. Other conditions amenable to treatment utilizing the present therapeutic compounds include, for example, Alzheimer's disease.

One of ordinary skill in the art can readily identify other degenerative disorders and diseases characterized by inappropriate cell death or inappropriate cell proliferation, or aberrant or disregulated apoptosis, which are amenable to treatment using the present therapeutic compounds. The therapeutic compounds comprise polypeptide, polynucleotide (e.g., DNA and/or RNA), amino acid, nucleotide, and/or chemical compounds, including analogs and/or modified forms of such compounds, and/or synthetic and/or chemical compounds. More particularly, the present therapeutic compounds comprise, e.g., a polypeptide having anti-apoptotic activity and/or polynucleotide encoding such a polypeptide; and/or a fragment, functional equivalent, hybrid, and/or mutant of such a polypeptide or polynucleotide, each of which can be delivered to a target cell.

Alternatively, e.g., therapeutic compounds according to the invention can be delivered by infecting the target cell with a vector containing a polynucleotide encoding one or more of the foregoing. The present therapeutic compounds can be delivered to the desired target cell as discussed below, for example, by choosing a receptor on the target cell surface which is specific for that cell type. The present therapeutic compounds can be delivered alone or in combination with other acceptable drug therapies. Further, the present therapeutic compounds can be delivered concurrently with other acceptable therapies specific for the particular degenerative disorder or disease being treated. For example, the present therapeutic compounds can be delivered concurrently with chemotherapeutic agents, gene therapy, or the like.

Moreover, the therapeutic compound may be delivered to the target area, and/or delivered and presented to the target cell's surface, and/or delivered into the cell membrane, and/or delivered across the membrane into the cell, whether, e.g., it is the anti-apoptotic polypeptide itself or the a polynucleotide encoding the polypeptide. Such delivery can be accomplished through different modes of contact of the therapeutic compound with the target area and/or cells. The particular mode of contact can also be readily selected by one of ordinary skill in the art. The cells can be contacted, for example, by pressure mediated delivery, by gene gun delivery, liposome delivery, ex vivo delivery; or by oral, intravenous, subcutaneous, or intramuscular administration. The present therapeutic compound can be delivered alone or in combination with and/or concurrently with other suitable drugs and/or courses of therapy.

The site of contact and the cells will be selected by one of ordinary skill in the art based upon an understanding of the particular degenerative disorder or disease being treated. In addition, the dosage, dosage frequency, and length of course of treatment, can be determined and optimized by one of ordinary skill in the art depending upon the particular degenerative disorder or disease being treated.

One method of delivering the therapeutic compounds of the present invention to the cell's surface, and/or into the cell's membrane, and/or into the cell itself, is by attaching the compound (e.g., a polypeptide having anti-apoptotic activity) to a ligand for which the target cell contains receptor sites. Thus, the therapeutic compound can be delivered by being carried along with the ligand. The choice of a carrier ligand will depend on several factors, as discussed herein and known to those of ordinary skill in the art. Suitable tissue-specific receptors include: Brain: nerve growth factor receptor (NGF-R); breast: prolactin receptor; stomach: gastrin receptor; skin: melanocyte stimulating hormone receptor (MSH-R), liver: asialoglycoprotein receptor; thyroid: thyroid stimulating hormone receptor (TSH-R); ovaries: luteinizing hormone receptor (LH-R), testis: human chorionic gonadotrophin receptor (hCG-R), T-cells: T-cell receptors; B cells: CD19; lung hyaluronate receptor CD44 isoform 4V (Mackay et al., 1994). In this regard, it will be appreciated that the ligand may be an antibody or fragment specific for the receptor, to which may be conjugated the therapeutic compound of the invention, such as the polypeptide having anti-apoptotic activity.

It may be desirable to employ biologically active fragments of the biologically active polypeptides according to the invention which are less likely to interfere with the ligand-receptor interaction, and which may be more easily transported across the cell membrane.

When a therapeutic compound of the invention is to be transported to the cell's surface, and/or into the cell membrane, and/or across the cell membrane into the cell as described above and the ligand is an antibody, it will be preferred to diagnostically or therapeutically label the therapeutic compound in such a way that the label will be relatively more effective when the therapeutic compound is bound, such as, for example, by means analogous to those described herein in the context of antibody transport.

It is also possible to utilize liposomes having the therapeutic compounds (e.g., antisense oligonucleotides) of the present invention in the membrane of the liposomes to specifically deliver the present therapeutic compounds to the target cells and/or target area. These liposomes can be produced so that they contain, in addition to the therapeutic compound, such other therapeutic compounds including drugs, radioisotopes, lectins and toxins, which would be released to the target cells and/or at the target site.

A preferred manner for delivering the polynucleotides encoding anti-apoptotic activity of the present invention (and/or their functional equivalents and/or hybrids and/or mutants) for diagnostic and/or therapeutic purposes is by the use of viral vectors. Suitable viral vectors for gene transfer include retroviruses (reviewed in Miller, et al., 1993) including human immunodeficiency virus (HIV), adenovirus derivatives (e.g., see Erzurum et al., 1993; Zabner et al., 1994; and Davidson et al., 1993; adeno-associated virus (AAV) (e.g., see Flotte et al., 1993) and herpes virus vectors (e.g., see Anderson et al., 1993). Other suitable viruses can be readily selected and employed by those of ordinary skill in the art. Other methods for DNA delivery include liposome mediated gene transfer (e.g., see Alton et al., 1993; and Nabel et al. 1993).

The use of viral vectors for introduction of genes into eukaryotic cells, including animal cells, e.g., human cells or other mammalian cells, is also reviewed, for example, in Varmus, 1988; Eglitis et al., 1988; Jaenisch, 1988; and Bernstein et al., 1985.

For the purposes of the present invention, it may be preferred to employ an attenuated viral or retroviral strain. Thus, for example, it is possible to use as vectors for the DNA sequences of the invention retroviruses having attenuated cytopathicity, such as HIV-2.sub.ST (Kong et al., 1988) or HIV-2.sub.UC1 (Evans et al., 1988), which enter neural cells by a CD4-dependent mechanism (Funke et al., 1987). The neurobiology of HIV infections is described, for example, in Johnson et al., 1988. Those of ordinary skill in the art will be able to target different cell populations having known susceptibilities to viruses by the exercise of routine skill. For example, CD4 is known to have a variant transcript in the human brain, with its highest content in forebrain (Maddon et al., 1986). Possible methods to target retroviral gene expression to specific cell types are reviewed by Boris-Lawrie and Temin (1993) Curr. Opin. Gellet. Dev. 3, 102-109.

Ideally, then, the choice of a gene or polynucleotide delivery system will be made by those of ordinary skill in the art, keeping in mind the objectives of efficient and stable gene transfer, with an appropriate level of gene expression, in a tissue-appropriate manner, and without any adverse effects (e.g., see Wolff et al., 1988.) With respect to delivery to a central nervous system target, many viral vectors, including HIV, offer the advantage of being able to cross the blood-brain barrier (Johnson et al., 1988).

Of special interest is the delivery of the therapeutic compounds of the present invention by ex vivo contact. The protocols known to one of ordinary skill in the art may be used for delivery of the therapeutic compounds of the present invention by ex vivo contact. Such protocols are described in detail in U.S. Pat. No. 5,547,932 of Curiel et al. and in the article by Simons and Mikhak, 1998, each incorporated herein by reference.

Numerous protocols well known to one of ordinary skill in the art may be used to deliver the therapeutic compounds of the present invention and for treatment of patients, using the therapeutic compounds of the present invention, wherein the patients have a degenerative disorder and disease characterized by inappropriate cell death or inappropriate cell proliferation, or aberrant or disregulated apoptosis. For example, such protocols well known to one of ordinary skill in the art are described in detail by the National Institutes of Health (NIH) in the issue of Recombinant DNA Research, Volume 17, Documents Relating to "NIH Guidelines for Research Involving Recombinant DNA Molecules," December 1992-June 1993, published January, 1995, (NIH Publication No. 95-3898, U.S. Department of Health and Human Services, Public Health Services, NIH, incorporated herein by reference); in particular, Human Gene Transfer Protocol (HGTP) No. 9303-038 by Heslop, H. E., et al.; HGTP No. 9303-040 by Simons, J.; HGTP No. 9306-034 by Seigler, H. F.; and HGTP 9306-046 by Barranger, J. A.

Diagnostic Applications of Compounds that Regulate or Modulate Apoptosis or Anti-Apoptotic Activity Antibodies raised against the present polypeptides having anti-apoptotic activity, fragments, functional equivalents, or hybrids or mutants thereof can be used to detect the respective polypeptides having anti-apoptotic activity in a human tissue sample, as well as to diagnose degenerative disorders or disease associated with the expression of the respective polypeptides having anti-apoptotic activity. Further, such antibodies can also be used to monitor the progress of degenerative disorders or disease associated with the expression of the respective polypeptides having anti-apoptotic activity.

Any source of human cells is suitable for use in the diagnostic testing in the present invention. The cells can be isolated from any human tissue including for example, heart, lung, tumor cells, brain, placenta, liver, skeletal muscle, kidney and pancreas. Extraction of polypeptides from the cell sample may be performed by any of the many means known in the art. For example, cells may be lysed by a detergent by mechanical means. If desired, nucleic acids can be removed from the cell preparation by enzymatic digestion or by precipitation. Such means are well known in the art.

Antibodies can be generated which are immunoreactive with the polypeptides having anti-apoptotic activity by the methods set forth herein. Appropriate antibodies can then be screened using the products of genes encoding polypeptides having anti-apoptotic activity.

The extracted polypeptides from the cell sample may be contacted with the antibody under suitable conditions for antibody-antigen complex formation. Generally, such conditions are physiological conditions. The polypeptide extract may be bound to a solid support such a nitrocellulose filter or a microtiter plate.

The antibody will generally have or bear a label which is a radio label, a florescent label, or an enzyme conjugate, which under appropriate conditions produces, for example, a colored reaction product. Antibodies and antibody labeling are described herein and known to those of ordinary skill in the art. Alternatively, if the antibody is not labeled, it can be detected by means of a second antibody from another species which is reacted with the first antibody. Suitable assay techniques, labels and means of detection are discussed herein.

A parallel sample to the test sample is employed to provide the control. The control sample consists of an equivalent amount of polypeptides extracted from cells, preferably in the same manner as those of the test sample. The amount of polypeptide can readily be determined by employing techniques well known in the art, including, for example, the Lowry or Bradford techniques. The cells used for preparing the control sample may be selected from: 1) cells of the same cell type as the test cells isolated from a normal human not suffering from the degenerative disorder; 2) cells of the same cell type as the test sample isolated from an established normal cell line; and 3) cells from the human who is being tested, which is a cell type that is different from the cell type of the test cells.

Test samples can also be screened for elevated levels of mRNA transcribed from the gene encoding a polypeptide having anti-apoptotic activity, according to methods well known in the art. For example, RNA extracted from B-cells may be used, or alternatively mRNA may be isolated from total cellular RNA. The mRNA may be purified, for example, by affinity chromatography on oligo (dT) cellulose which binds to the poly (A) tract at the 3' end of most mRNA. As is well known to those of ordinary skill in the art, it is essential that ribonuclease activity be minimized during preparation and assaying.

A DNA probe may be selected from any of the polypeptide coding sequences of the gene encoding the polypeptide having anti-apoptotic activity. Preferably, the probe will be selected from sequences of the 5' or first exon of the gene so that RNA can be detected. Preferably, the probe contains at least 15 nucleotides of the gene sequence encoding the polypeptide having anti-apoptotic activity. In order to perform the hybridization, it is desirable that the probe be single stranded. Thus, if the probe is double stranded, it should be denatured to a single stranded form. Means for denaturing are well known in the art, including alkali or heat treatment. The probe can then be contacted with the RNA derived from the cell sample under conditions where homologous RNA-DNA hybrids form and are stable. Such conditions are well known in the art. Means for detecting hybrids are many and well known, but often involve the use of radiolabeled probes and nucleases which degrade single stranded DNA. Other methods known in the art may be used.

Control samples can be derived from any of these cell sources described above for use in the antibody diagnostic tests. Samples and controls should preferably be prepared in parallel under similar conditions.

The diagnostic methods and compounds of the present invention are useful for determining whether a disease or degenerative disorder is linked to abnormal expression of the polypeptide having anti-apoptotic activity, to the expression of mutants of the anti-apoptotic polypeptide, as well as for determining the effect of over expression or loss of expression of the anti-apoptotic polypeptide in animal models such as transgenic mice and/or homozygous null mice. Methods for determining whether a disease/degenerative disorder is linked to abnormal expression of the anti-apoptotic polypeptide include analyzing the expression of the anti-apoptotic polypeptide in diseased cells or tissue as compared to normal cells or tissue by for example, Northern and/or Western blots, as well as by other assay methods readily chosen and employed by those of ordinary skill in the art. Once It has been determined that a disease or degenerative disorder is linked to abnormal expression of the anti-apoptotic polypeptide, the disease or disorder can be diagnosed in an individual.

Methods of Enhancing the Stability, Growth, and/or Productivity of Cells

Numerous protocols well known to one of ordinary skill in the art may be used to deliver the compounds of the present invention to cells for enhancing the stability, growth, and/or productivity of the cells. For example, such protocols are described in detail by Knott et al., 1996; Terada et al., 1997; Chung et al, 1998; Kim et al., 1998; Bierau et al., 1998; Simpson et al., 1998; Bierau et al., 1998; Ishaque and Al-Rubeai, 1998; each incorporated herein by reference.

The stability, growth, and/or productivity of cells may be enhanced using the compounds of the present invention, for example, by transfection or retrovirus infection of a polynucleotide encoding a polypeptide having anti-apoptotic activity, and expressing the polypeptide in the cells; wherein the cells under normal conditions do not express such a polypeptide. Examples of such cells are hybridomas, fibroblasts, lymphoid cells, haematopoietic cells, cells derived from the embryonic central nervous system, and cells derived from normal, dysplastic, or neoplastic tissue.

In particular, the stability, growth, and/or productivity of the cells may be enhanced, for example, by transfection or retrovirus infection of a polynucleotide encoding at least one of HCMV polypeptides pUL36, $pUL37_S$, $pUL37_M$, or $pUL37_L$, or encoding at least one fragment thereof, or a homologue of such HCMV polypeptide or fragment thereof, and expressing the polypeptide in the cells; wherein the cells under normal conditions do not express such a polypeptide.

Production and Application of Antibodies

Anti-apoptotic polypeptides or analogs thereof, may be used to immunize an animal for the production of specific antibodies. These antibodies may comprise a polyclonal antiserum or may comprise a monoclonal antibody produced by hybridoma cells. For general methods to prepare antibodies, see E. Harlow and D. Lane (1988) *Antibodies: A Laboratory Manual*, Cold Spring Harbor Laboratory, Cold Spring Harbor, N.Y., which is incorporated herein by reference.

For example, but not for limitation, a recombinant-produced viral polypeptide having anti-apoptotic activity, can be injected into a mouse along with an adjuvant following immunization protocols known to those of ordinary skill in the art so as to generate an immune response. Typically, approximately at least 1-50 μg of a polypeptide or analog is used for the initial immunization, depending upon the length of the polypeptide. Alternatively or in combination with a recombinantly produced polypeptide, a chemically synthesized peptide having a sequence of the viral polypeptide may be used as an immunogen to raise antibodies which bind to it. Immunoglobulins which bind the recombinant polypeptide with a binding avidity of at least $1\times10^7$ $M^{-1}$ can be harvested from the immunized animal as an antiserum., and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly produced polypeptide, or chemically synthesized polypeptide, with an avidity of at least $1\times10^6$ $M^{-1}$. Animals other than mice and rats may be used to raise antibodies; for example, goats, rabbits, sheep, and chickens may also be employed to raise antibodies reactive with a specific polypeptide. Transgenic mice having the capacity to produce substantially human antibodies also may be immunized and used for a source of antiserum and/or for making monoclonal secreting hybridomas.

Bacteriophage antibody display libraries may also be screened for binding to a specific polypeptide, for example pUL36, $pUL37_S$, $pUL37_M$, or $pUL37_L$, or a fusion polypeptide comprising a polypeptide sequence of a particular epitope (generally at least 3 to 5 contiguous amino acids). Generally such polypeptides and the fusion polypeptide portions consisting of specific anti-apoptotic polypeptide sequences for screening antibody libraries comprise about at least 3 to 5 contiguous amino acids of a specific polypeptide, frequently at least 7 contiguous amino acids of the polypeptide, usually comprise at least 10 contiguous amino adds of the polypeptide, and most usually comprise a polypeptide sequence of at least 14 contiguous amino acids.

Combinatorial libraries of antibodies have been generated in bacteriophage lambda expression systems which may be screened as bacteriophage plaques or as colonies of lysogens (Huse et al., 1989; Caton and Koprowski, 1990; Mullinax et al., 1990; Persson et al., 1991; McCafferty J., et al. (1992)

Patent No. WO 92/01047; and Griffiths, A. D., et al. (1999) U.S. Pat. No. 5,885,793, each of which is incorporated herein by reference). Various embodiments of bacteriophage antibody display libraries and lambda phage expression libraries have been described, e.g., by Kang et al. (1991) *Proc. Natl. Acad. Sci.* (U.S.A.) 88, 4363; Clackson et al. (1991) *Nature* 352, 624; McCafferty et al. (1990) *Nature* 348, 552; Burton et al. (1991) *Proc. Natl. Acad. Sci.* (U.S.A.) 88, 10134; Hoogenboom et al. (1991) *Nucleic Acids Res.* 19, 4133; Chang et al. (1991) *J. Immunol.* 147, 3610; Breitling et al. (1991) *Gene* 104, 147; Marks et al. (1991) *J. Mol. Biol.* 222,581; Barbas et al. (1992) *Proc. Natl. Acad. Sci.* (U.S.A.) 89, 4457; Hawkins and Winter (1992) *J. Immunol.* 22, 867; Marks et al. (1992) *Biotechnology* 10, 779; Marks et al. (1992) *J. Biol. Chem.* 267, 16007; Lowman et al. (1991) *Biochemistry* 30, 10832; Lerner et al. (1992) *Science* 258, 1313; each of which is incorporated herein by reference. Typically, a bacteriophage antibody display library is screened with a polypeptide, such as a viral polypeptide having anti-apoptotic activity, that is immobilized (e.g., by covalent linkage to a chromatography resin to enrich for reactive phage by affinity chromatography) and/or labeled (e.g., to screen plaque or colony lifts).

Polypeptides which are useful as immunogens, for diagnostic detection of antibodies in a sample, for diagnostic detection and quantitation of an anti-apoptotic polypeptide in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other polypeptides of humans, mice, or other contaminants.

For some applications of these antibodies, such as identifying immunocrossreactive polypeptides, the desired antiserum or monoclonal antibody(ies) is/are not monospecific. In these instances, it may be preferable to use a synthetic or recombinant fragment of the full-length anti-apoptotic polypeptide as an antigen rather than using the full-length native polypeptide. More specifically, where the object is to identify immunocrossreactive polypeptides that comprise a particular structural moiety, such as a binding domain, it is preferable to use as an antigen a fragment corresponding to part or all of a commensurate structural domain in the anti-apoptotic polypeptide.

If an antiserum is raised to a fusion anti-apoptotic polypeptide, such as a fusion protein comprising immunogenic epitopes of a particular HCMV polypeptide, fused to β-galactosidase or glutathione S-transferase, the antiserum is preferably preadsorbed with the non-HCMV fusion partner (e.g., β-galactosidase or glutathione S-transferase) to deplete the antiserum of antibodies that react, i.e., specifically bind to, the non-HCMV portion of the fusion polypeptide that serves as the immunogen. Monoclonal or polyclonal antibodies which bind to the anti-apoptotic polypeptide can be used to detect the presence of such polypeptides in a sample, such as a Western blot of denatured polypeptides (e.g., a nitrocellulose blot of an SDS-PAGE) obtained from a cell extract, or from serum, tissue, or lymphocyte sample of a patient. Preferably quantitative detection is performed, such as by densitometric scanning and signal integration of a Western blot. The monoclonal or polyclonal antibodies will bind to the denatured anti-apoptotic polypeptide epitopes and may be identified visually or by other optical means with a labeled second antibody or labeled *Staphylococcus aureus* protein A by methods known in the art.

One use of such antibodies is to screen cDNA expression libraries, preferably containing cDNA derived from human or murine mRNA from various tissues, for identifying clones containing cDNA inserts which encode structurally-related, immunocrossreactive polypeptides, that are candidate anti-apoptotic-polypeptide-binding factors or anti-apoptotic-related polypeptides. Such screening of cDNA expression libraries is well known in the art, and is further described in Young et al. (1983) *Proc. Natl. Acad. Sci.* (U.S.A.) 80, 1194-1198, which is incorporated herein by reference as well as other published sources. Another use of such antibodies is to identify and/or purify immunocrossreactive polypeptides that are structurally or evolutionarily related to the native anti-apoptotic polypeptide or to the corresponding anti-apoptotic polypeptide fragment (e.g., functional domain; binding domain) used to generate the antibody. The antibodies of the invention can be used to measure levels of a specific polypeptide in a cell or cell population, for example in a cell explant (e.g., lymphocyte sample) obtained from a patient. The antibodies can be used to measure the corresponding polypeptide level by various methods, including but not limited to: 1) standardized ELISA on cell extracts; 2) immunoprecipitation of cell extracts followed by polyacrylamide gel electrophoresis of the immunoprecipitated products and quantitative detection of the band(s) corresponding to the specific polypeptide; and 3) in situ detection by immunohistochemical staining with the antibodies and detection with a labeled second antibody. The measurement of the level of the specific polypeptide in a cell or cell population is informative regarding the apoptosis status of the cell or cell population.

Various other uses of such antibodies are to diagnose virally-induced diseases (e.g., HCMV mononucleosis; congenital HCMV infection which may cause fetus abnormalities; HCMV infection in the immunocompromised host, such as AIDS patients, bone marrow transplant recipients, organ transplant recipients which frequently results in HCMV hepatitis; HCMV pneumonitis; HCMV esophagitis; HCMV colitis; HCMV retinitis; HCMV disseminated disease, which is often fatal), and for therapeutic application (e.g., as cationized antibodies or by targeted liposomal delivery) to treat such diseases, and the like.

A preferred embodiment is a polyclonal or monoclonal antibody that recognizes at least one of HCMV polypeptides pUL36, $pUL37_S$, $pUL37_M$, or $pUL37_L$.

Of special interest to the present invention are antibodies which are produced in humans, or are "humanized," i.e., non-immunogenic in a human, by recombinant or other technology such that they will not be antigenic in humans, or will be maintained in the circulating serum of a recipient for a longer period of time. Humanized antibodies may be produced, for example by replacing an immunogenic portion of an antibody with a corresponding, but non-immunogenic portion, i.e., chimeric antibodies, (Robinson et al., International Patent Publication PCT/US86/02269; Akira et al., European Patent Application 184,187; Taniguchi, M., European Patent Application 171,496; Morrison et al., European Patent Application 173,494; Neuberger et al., PCT Application WO 86/01533, Cabilly et al., European Patent Application 125, 023; Better et al., 1988; Liu et al., 1987; Liu et al., 1987; Sun et al., 1987; Nishimura et al., 1987; Wood et al., 1985; Shaw et al., 1988). General reviews of "humanized" chimeric antibodies are provided by Morrison S. L., 1985 and by Oi et al., 1986. Suitable "humanized" antibodies can be alternatively produced as described by Jones et al., 1986; Verhocyan et al., 1988; and Beidler et al., 1988. Resurfaced antibodies as described by Pedersen et al., U.S. Pat. No. 5,639,641, are especially preferred.

Isolation and Synthesis of Polynucleotides and Polypeptides

The instant polynucleotides and polypeptides may be obtained as described herein, that is by recombinant means, or may be used to obtain homologous polynucleotides and polypeptides by hybridization, for example, an instant polynucleotide can be used as a probe of a gene bank or library to identify clones with suitable homology therewith.

Also, within the confines of available technology, the polynucleotides and polypeptides may be synthesized in vitro using, for example, solid phase oligonucleotide and oligopeptide synthetic methods known in the art. In particular, oligonucleotides, such as antisense oligonucleotides, can be synthesized on an Applied BioSystems oligonucleotide synthesizer according to specifications provided by the manufacturer.

Methods for PCR amplification are described in the art (H. A. Erlich, Ed. (1992) *PCR Technology: Principles and Applications for DNA Amplification*, Freeman Press, New York, N.Y.; Innis, Gelfland, Snisky, and White, Eds. (1990) *PCR Protocols: A Guide to Methods and Applications*, Academic Press, San Diego. Calif.; Mattila et al., 1991; Eckert, K. A. and Kunkel, T. A., 1991; McPherson, Quirkes, and Taylor (1991) *PCR Methods and Applications* 1, 17; PCR, IRL Press, Oxford; and U.S. Pat. No. 4,683,202; each of which is incorporated herein by reference).

Modification of Polynucleotides and Polypeptides

Modified polynucleotides and polypeptides are defined as those polynucleotides and polypeptides that, within the confines of available technology, may be chemically or genetically modified using chemical and genetic engineering methods known in the art. Examples of methods known in the art include, but are not limited to, those described in Ausubel et al., Eds. (1995) *Current Protocols in Molecular Biology*, John Wiley & Sons, Inc.; Sambrook et al. (1989) *Molecular Cloning: A Laboratory Manual*, 2d Ed., Cold spring harbor Laboratory Press, Cold Spring Harbor, N.Y.; and Creighton, Ed. (1984) *Proteins, Structures and Molecular Principles*, W.H. Freeman and Company, New York; each of which is incorporated herein by reference.

Relevant chemical modifications of polynucleotides include substitutions of normal phosphodiester bonds with one of the following types of bonds: 1) phosphotriester, methylphosphonate, phosphorothioate, as described in C. A. Stein and Y. C. Cheng, Science 261, 1004-1012, 1993 and incorporated herein by reference; 2) use of unnatural bases such as C-5 propynyl-2'-deoxyuridine or C-5 propynyl-2'-deoxycytidine; 3) use of unnatural sugars such as 2'-fluororibose or 2'-O-methylribose, as described in R. W. Wagner, Nature 372, 333-335, 1994 and incorporated herein by reference; and 4) peptide nucleic acids (PNA) containing amide-containing backbones with nucleobases attached thereto, such as those described in Egholm, M., et al., J. Am. Chem. Soc. 114, 1895-1897, 1992; and Hyrup, B., et al., Bioorg. Med. Chem., 4, 5-23, 1996; each of which is incorporated herein by reference.

In particular, it may be advantageous to employ a peptide analog of pUL36, pUL37$_S$, pUL37$_M$, or pUL37$_L$ as a pharmaceutical agent or as a commercial assay or research reagent. For example, a peptide analog of pUL36, pUL37$_S$, pUL37$_M$, or pUL37$_L$, having high affinity for binding FADD, FLICE (caspase 8), caspase 3, Apaf-1, Bcl-x$_L$, Bcl-2, Bak, ICE, Bax, BNIP-3, and ANT, may be used as a competitive inhibitor of (or competitive compound that diminishes) the intermolecular polypeptide complex formation by competing with native HCMV polypeptide for binding to FADD, FLICE (caspase 8), caspase 3, Apaf-1, Bcl-x$_L$, Bcl-2, Bak, ICE, Bax, BNIP-3, and ANT.

As an example, the HCMV polypeptides may be modified by the attachment of linkers that join two or more of the viral polypeptides together, for the purposes of screening for and characterizing physiological molecules that interact with such viral polypeptides. For example, two or more of the viral polypeptides having anti-apoptotic activity may be joined together by a peptide linker. As a further example, the polypeptides may be modified by means of genetic engineering so that two or more of the polypeptides are joined together when expressed as a fusion polypeptide.

Production and Application of Peptidomimetics

In addition to polypeptides consisting only of naturally-occurring amino acids, peptide analogs are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere, J., 1986; Veber and Freidinger, 1985; and Evans et al., 1987; each of which is incorporated herein by reference) and are usually developed with the aid of computerized molecular modeling.

Peptide mimetics that are structurally similar to therapeutically useful peptides may be used to produce an equivalent therapeutic or prophylactic effect. Generally, peptidomimetics are structurally similar to a paradigm polypeptide, i.e., a polypeptide that has a biochemical property or pharmacological activity (e.g., pUL36, pUL37$_S$, pUL37$_M$, and pUL37$_L$), but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. (1983) in *Chemistry and Biochemistry of Amino Acids, Peptides, and Proteins*, B. Weinstein, Ed., Marcel Dekker, New York, p. 267; Spatola, A. G. (1983) *Vega Data, Peptide Backbone Modifications*, Vol. 1, Issue 3 (general review); Moreley, J. S. (1980) *Trends Pharm. Sci.* 463-468 (general review); Hudson, D. et al. (1979) *Int. J. Pept. Prot. Res.* 14, 177-185 (—CH$_2$NH—, —CH$_2$CH$_2$—); Spatola, A. F., et al. (1986) *Life Sci.* 38, 1243-1249 (—CH$_2$—S—); Hann, M. M. (1982) *J. Chem. Soc. Perkin Trans. I* 307-314 (—CH=CH—, cis and trans); Almquist, R. G. et al. (1980) *J. Med. Chem.* 23, 1392-1398 (—COCH$_2$—); Jennings-White, C. et al., (1982) *Tetrahedron Lett.* 23, 2533 (—COCH$_2$—); Szelke, M., et al., European Appln. EP 45665, CA: 97:39405 (—CH(OH)CH$_2$—); Holladay, M. W., et al. (1983) *Tetrahedron Lett.* 24, 4401-4404 (—CH(OH)CH$_2$—); and Hruby, V. J., (1982) *Life Sci.* 31, 189-199 (—CH$_2$—S—); each of which is incorporated herein by reference.

A particularly preferred non-peptide linkage is —CH$_2$NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivatization (e.g., labeling) of peptidomimetics should not abolish the desired biological or pharmacological activity of the peptidomimetic.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch, 1992, which is incorporated herein by reference); for example, by adding internal cysteine residues capable of forming intramolecular disulfide bridges which cyclize the peptide. Cyclic peptides comprising the sequence -WGR- and/or -QDN- and/or -FRDG-frequently are preferred.

The amino acid sequences of the HCMV polypeptides, pUL36, pUL37$_S$, pUL37$_M$, and pUL37$_L$, identified herein will enable those of ordinary skill in the art to produce polypeptides corresponding to the HCMV polypeptide sequences and sequence variants thereof. Such polypeptides may be produced in prokaryotic or eukaryotic host cells by expression of polynucleotides encoding one of the HCMV polypeptide sequences identified herein, frequently as part of a larger polypeptide. Alternatively, such oligopeptides may be synthesized by chemical methods.

Methods for expression of heterologous polypeptides in recombinant hosts, chemical synthesis of polypeptides, and in vitro translation are well known in the art and are described further in Sambrook et al. (1989) *Molecular Cloning: A Laboratory Manual*, 2nd Ed., Cold Spring Harbor N.Y.; Berger and Kimmel (1987) *Methods in Enzymology*, Volume 152, Guide to Molecular Cloning Techniques, Academic Press, Inc., San Diego, Calif.; Merrifield, J. (1969) *J. Am. Chem. Soc.* 91, 501; Chaiken I. M. (1981) *CRC Crit. Rev. BioChem.* 11, 255; Kaiser et al. (1989) *Science* 243, 187; Merrifield, B. (1986) *Science* 232, 342; Kent, S. B. H. (1988) *Ann. Rev. BioChem.* 57, 957; and Offord, R. E. (1980) *Semisynthetic Proteins*, Wiley Publishing; each of which is incorporated herein by reference.

Peptides of a specific sequence can be produced typically by direct chemical synthesis, and used as antiviral compounds to competitively inhibit or diminish the interaction of pUL36, pUL37$_S$, pUL37$_M$, and pUL37$_L$ with a physiological molecule that specifically binds to at least one of the HCMV polypeptides. Such synthetic peptides are frequently produced as modified peptides, with nonpeptide moieties attached by covalent linkage to the N-terminus and or C-terminus.

In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylations (e.g., methylation) and carboxyterminal modifications such as amidation, as well as other terminal modifications, including cyclization, may be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Such peptides may be used therapeutically to treat disease by interfering with the anti-apoptotic activity of viral polypeptides and/or regulating apoptosis in a cell population of a patient.

Methods of Rational Drug Design

HCMV polypeptides pUL36, pUL37$_S$, pUL37$_M$, and pUL37$_L$, especially those portions of the HCMV polypeptides which form direct or specific contact with cellular polypeptides, such as FADD, FLICE (caspase 8), caspase 3, Apaf-1, Bcl-x$_L$, Bcl-2, Bak, ICE, Bax, BNIP-3, and ANT, can be used for the rational drug design of candidate antiviral drugs. Using the methods of the present invention to identify and isolate heterodimer complexes formed between one of the HCMV polypeptides and a specific cellular polypeptide, such as FADD, FLICE (caspase 8), caspase 3, Apaf-1, Bcl-x$_L$, Bcl-2, Bak, ICE, Bax, BNIP-3, and ANT, permits the production of substantially pure complexes and computational models that can be used for protein X-ray crystallography or other methods of structure analysis, such as the DOCK program (Kuntz et al., 1982; and Kuntz I. D., 1992, each of which is incorporated herein by reference) and variants thereof. Potential therapeutic drugs may be designed rationally on the basis of structural information thus provided.

Thus, the present invention may be used to design drugs, including drugs with a capacity to interfere with the anti-apoptotic activity of viral polypeptides, by preventing the viral polypeptide having anti-apoptotic activity from specifically binding and forming a heterodimer complex with a physiological molecule and, thereby, induce or restore apoptosis in the host cells.

In one embodiment, such drugs are designed to prevent the formation of the heterodimer complex by preventing the viral polypeptide, having anti-apoptotic activity, from specifically binding to a physiological molecule such as a cellular polypeptide.

In a preferred embodiment, such drugs are designed to interfere with the anti-apoptotic activity of HCMV polypeptides and, thereby, induce or restore apoptosis in the host cells. In particular, the drug would bind directly to the viral polypeptide and prevent it from forming a specific heterodimer complex with a physiological molecule such as a cellular polypeptide.

In another preferred embodiment, such drugs are designed to prevent at least one of the HCMV polypeptides pUL36, pUL37$_S$, pUL37$_M$, or pUL37$_L$, from specifically binding to and forming a heterodimer complex with at least one of FADD, FLICE (caspase 8), caspase 3, Apaf-1, Bcl-x$_L$, Bcl-2, Bak, ICE, Bax, BNIP-3, and ANT.

As another preferred embodiment, an antiviral compound may be obtained by employing the rational design of a compound that would interfere with the anti-apoptotic activity of HCMV polypeptides pUL36, pUL37$_S$, pUL37$_M$, and pUL37$_L$ and, thereby, induce or restore apoptosis in the host cells. The antiviral compound could interfere with the anti-apoptotic activity of such polypeptides by, for example, disrupting the specific binding of a physiological molecule with such polypeptides or could bind directly to the viral polypeptide and diminish the anti-apoptotic function of the polypeptide.

In one variation on the design, such drugs are structural mimics of the binding domain of the viral polypeptide, such as an HCMV polypeptide, having anti-apoptotic activity or the binding domain of a cellular polypeptide that specifically interacts with such a viral polypeptide.

As a preferred embodiment, a candidate antiviral compound may be obtained by employing the rational design of a compound that would be complementary to the structural domain of either pUL36, pUL37$_S$, pUL37$_M$, or pUL37$_L$, or the domain of a cellular polypeptide having a domain that interacts with a HCMV anti-apoptotic polypeptide, and inhibits or diminishes the specific interaction between the viral polypeptide and the cellular polypeptide.

The design of compounds that preferentially interact with and disrupt the formation or stability of the heterodimer complex formed between a viral polypeptide having anti-apoptotic activity and a polypeptide that specifically interacts with the viral polypeptide, can be developed using computer analysis of three dimensional structures. A set of molecular coordinates can be determined using: 1) crystallographic data, 2) data obtained by other physical methods, 3) data generated by computerized structure prediction programs operating on the deduced amino acid sequence data, or, preferably, a combination of these data.

A preferred embodiment is the design of compounds that interact preferentially with a heterodimer complex formed between an HCMV polypeptide having anti-apoptotic activity and a cellular polypeptide that specifically interacts with the viral polypeptide, developed using computer analysis of three dimensional structures.

Another preferred embodiment is the design of compounds that interact preferentially with a heterodimer complex formed between any one of HCMV polypeptides pUL36, pUL37$_S$, pUL37$_M$, and pUL37$_L$, and a cellular polypeptide, such as FADD, FLICE (caspase 8), caspase 3, Apaf-1, Bcl-x$_L$, Bcl-2, Bak, ICE, Bax, BNIP-3, and ANT, developed using computer analysis of three dimensional structures.

Examples of physical methods that may be used to define structure are, for example, two-dimensional homonuclear correlated spectroscopy (COSY). For those of ordinary skill in the art, one-dimensional NMR spectroscopy, COSY provides the kind of information available from a single-frequency decoupling experiment (e.g., which spins are scalar coupled to one another). In a COSY plot, the 1 dimensional spectrum lies along the diagonal, and the off-diagonal elements are present at the intersection of chemical shifts of groups that are J coupled. The "fingerprint" region contains ($^1$HN, $^1$H-) cross-peaks from the peptide backbone. The degree of resolution of the "fingerprint" region of the COSY map obtained in H$_2$O is a good predictor of the success of sequence-specific assignments to be obtained without recourse to isotopic labeling.

Transferred nuclear Overhauser Effect (TRNOE) spectra ($^1$H NMR) relies on different two dimensional NOE spectra, and, in essence, looks at the conformation of the ligand just after it has dissociated from the polypeptide. The use of TRNOE presumes, however, that the bound and free ligands are in fast exchange on the chemical shift time scale, which translates to a ligand K$_D$ greater than or equal to about $1\times10^{-4}$ M. TRNOE methods are useful to crosscheck and augment the distance information obtained by other approaches.

It is not intended that the present invention be limited by the particular method used to obtain structural information. Furthermore, it is not intended that the present invention be limited to a search for any one type of drug; one or more of the compounds may be naturally-occurring or may be synthetic, or may be a chemically modified form of a naturally occurring molecule.

In some embodiments, it is desirable to compare the structure of the viral polypeptides, having anti-apoptotic activity, such as the HCMV polypeptides pUL36, pUL37$_S$, pUL37$_M$, and pUL37$_L$, to the structure(s) of other polypeptides. This structural comparison will aid in the identification of and selection of drugs that either selectively affect specific polypeptides, e.g., pUL36, pUL37$_S$, pUL37$_M$, and pUL37$_L$, or have a broad spectrum effect on more than one species of related polypeptide (e.g., other related anti-apoptotic viral polypeptides, in particular, other related anti-apoptotic HCMV polypeptides).

EXPERIMENTAL EXAMPLES

The invention will now be illustrated by reference to non-limiting examples. Unless otherwise stated, all percents, ratios, parts, etc. are by weight.

Example 1

Induction and Detection of Apoptotic Activity.

Tumor necrosis factor receptor 1 (TNF-R1)-mediated apoptosis was induced by exposure of HeLa and MRC-5 cells to tumor necrosis factor-α (TNF-α) (Sigma, 10-60 ng/mL)+ CHX (10-30 µg/mL). Fas-mediated apoptosis was induced by exposure of cells to an anti-Fas antibody (Coulter, 7C11 antibody at 0.2-4 µg/mL)+CHX (10-30 µg/mL). The degree of cell death was determined by the visual scoring of surviving cells, in representative fields, under a phase microscope. A similar degree of cell death occurred in fibroblasts when examined 5 to 28 h after the start of exposure, or a similar degree of cell death occurred in HeLa cells when examined 9-28 h after the start of exposure. Further, a similar degree of cell death for a given reagent was produced when any concentration within the range indicated above was used.

The time-course of apoptosis was also analyzed by examining the expression of phosphatidylserine on the cell surface, as detected with FITC-labeled Annexin V, and by a dye-exclusion test using propidium iodide. These two tests were performed with an ApoAlert Annexin V Apoptosis kit (Clontech) in accordance with the manufacturer's recommendations, on a flow cytometer (FACScan, Becton-Dickinson).

DNA degradation in MRC-5 cells was examined as follows. $10^6$ MRC-5 cells were either exposed for 12 h to anti-Fas antibody in the presence of cycloheximide or not exposed (control). The cells were then resuspended by trypsinization, sedimented, and the pellet resuspended in 10 mL of lysis buffer (1% NP-40, 20 mM EDTA, 50 mM Tris.HCl, pH 7.5). After a 10 sec incubation at room temperature, the suspension was centrifuged in an Eppendorf centrifuge (5 min, 15,000 g), and the supernatant separated from the pellet and retained. Thereafter, the pellet was resuspended in 10 mL of the lysis buffer, centrifuged, and the resulting supernatant combined with the previously retained supernatant. Sodium dodecyl sulfate (at a final concentration of 1%), RNase A (Sigma, at a final concentration of 5 mg/mL), and Proteinase K (Sigma, at a final concentration of 2.5 mg/mL) were then added to the combined supernatant, and the mixture incubated at 56° C., for 2 h. Ammonium acetate (at a final concentration of 2.5 M) and 2 volumes of ethanol were then added, mixed, and the mixture stored overnight, at –20° C. After the overnight precipitation, the DNA was sedimented by centrifugation in an Eppendorf centrifuge, for 30 min, at 14,000 rpm, then electrophoretically resolved on a 1% agarose gel, and visualized by ethidium bromide staining.

The degree of cell death in cells transfected with an indicator plasmid expressing *E. coli* β-galactosidase was determined by either a β-galactosidase ELISA (Boehringer Mannheim), in accordance with the manufacturer's recommendations, or by visually scoring, under a microscope, positive blue cells, expressing β-galactosidase, after staining them with X-gal.

The degree of cell death in cells transfected with an indicator plasmid expressing Green Fluorescent Protein was determined by measuring the fraction of fluorescent cells in the total cell population, on a flow cytometer (FACScan, Becton-Dickinson).

Example 2

Detection of Intracellular Polypeptides.

Cells were trypsinized, washed in Tris buffered saline, resuspended in a lysis buffer (150 mM NaCl, 5 mM EDTA, 50 mM Tris.HCl pH 8.0, 1% Triton X-100), freshly supplemented with phenylmethylsulfonyl fluoride (0.1 mM), leupeptin (1 µg/mL) and pepstatin (1 µg/mL), incubated on ice for 30 minutes, and centrifuged at 16,000 g for 15 minutes, at 4° C. Cytochrome c and procaspase 9 were detected in S-100 fractions of cells (Li et al., 1997, which is incorporated herein by reference).

The intracellular polypeptides were detected by Western blot analysis. Samples containing protein were electrophoretically resolved under reduced conditions, on Laemmli SDS-PAGE (Novex), after equal amounts of protein were loaded per well of the gel, detected using a standard Western blot protocol and a luminol-based ECL Western Blotting system (Amersham). The following antibodies were used in the Western blot analysis: anti-human Bid C-20 (Santa Cruz Biotechnology), 5F7 anti-human caspase 8 (Upstate Biotechnology), C210 anti-PARP (Biomol), 7H, 8.2; C12 anti-cytochrome c (Pharmigen), B40 anti-human caspase 9 (Pharmigen), FITC-anti-mouse IgG (Sigma), HRP-anti-mouse IgG-$F_c$ (Pierce), HRP-anti-mouse IgG$_{2b}$ (Boehringer Mannheim), HRP-anti-rabbit IgG, and HRP-anti-mouse Ig (Amersham).

Example 3

Detection of Anti-Apoptotic Activity in Virally-Infected Cells.

Two methods were used for the induction of apoptosis. The host cells were treated with anti-Fas antibodies or treated with tumor necrosis factor-α (TNF-α). Both methods of treatment activate the apoptotic signaling pathways involved in the elimination of virally-infected cells in the host animals (Mestan et al., 1986; Vilcek and Sen, 1996; Wong et al., 1986; Kagi et al., 1994; Sieg, et al., 1996; and Razvi and Welsh, 1995; each of which is incorporated herein by reference).

These experiments were performed on MRC-5, a normal human fibroblast cell line which can be productively infected by HCMV in cell culture. The present inventors first examined whether infection of cells with HCMV alters the cell's sensitivity to Fas- or TNF-R1-mediated apoptosis. In the absence of HCMV infection, MRC-5 diploid fibroblasts readily underwent apoptosis within the first 24 h of their exposure to either an anti-Fas antibody or to TNF-α, in the presence of cycloheximide (CHX) (FIG. 1). FIG. 2A shows that MRC-5 cells died (disintegrated and then disappeared from the plate) within the first 24 h of their exposure to the anti-Fas monoclonal antibody 7C 11, or to TNF-α as observed under a phase microscope. These reagents killed cells only in the presence of cycloheximide (CHX). CHX alone did not kill cells (not shown).

Both Fas- and TNF-R1-mediated MRC-5 cell death exhibited typical features of apoptosis such as the emergence of phosphatidylserine in the outer layer of the cell plasma membrane, surface blebbing, and DNA degradation, and was prevented by the caspase inhibitor Z-VADfmk. For example, anti-Fas antibody-induced cell death of MRC-5 cells was examined by a dye-exclusion test on a flow cytometer (FIG. 2B), and the results were consistent with those obtained by visual microscopic examination. Fas-mediated cell death was accompanied by the characteristic apoptotic events such as: 1) surface blebbing, as observed under a phase microscope (not shown); 2) emergence of phosphatidylserine, an early marker of apoptosis in the outer layer of the cell plasma membrane (FIG. 2C); 3) DNA degradation (not shown); and 4) protection by the caspase inhibitor Z-VADfmc (FIGS. 2A-2C).

MRC-5 cells were infected with HCMV and tested for changes in their sensitivity to anti-Fas antibody- or TNF-α-induced apoptosis. Following 0, 1, 2, or 3 days of infection, cells were treated either with anti-Fas antibody or TNF-α in the presence of CHX for 24 hours and surviving cells were counted under the microscope. Treatment on day 0 and day 1 post-infection still killed most cells, but by day 2 of the infection, the effect of treatment was almost completely inhibited, and most cells remained alive, as was evident by microscopic examination for cell death (FIG. 1). The Flow-cytometric PI dye-exclusion test and the test for the surface expression of phosphatidylserine by apoptotic cells confirmed that a major fraction of HCMV-infected cells (72 h post-infection) retained their capacity to exclude the dye, and did not express phosphatidylserine following their exposure to anti-Fas antibody+CHX (data not shown). These results suggest that one or more factors encoded by HCMV block both Fas- and TNF-α-mediated cell death in infected cells.

The present inventors examined whether infection of cells with HCMV alters the cell's sensitivity to Fas- or TNF-R1-mediated apoptosis and demonstrated that infection with HCMV protects against such apoptosis.

Example 4

Determination that the Gene(s) Responsible for the Resistance to Apoptosis is Transcribed Early in the Course of the Viral Replication, and Inhibitors of Viral Replication Diminish but do not Abolish the Resistance to Apoptosis in HCMV-Infected Cells.

The finding by the present inventors that MRC-5 cells become resistant to apoptosis only at a late stage of HCMV infection suggests that such resistance is mediated by: 1) a late HCMV gene; or 2) by an early or an immediate-early HCMV gene, the product of which accumulated to the level sufficient to protect cells from apoptosis only by day 2 of infection. To discriminate between these two mechanisms, MRC-5 cells were infected with HCMV in the presence (or absence) of inhibitors of viral DNA polymerase, such as phosphonacetic acid or gancyclovir (Huang, 1975; Crumpacker, 1996) which prevent the expression of the late genes of HCMV in the host cell (Mocarski, 1996).

MRC-5 cells uninfected (FIG. 3A) or infected with HCMV (FIG. 3B) were either untreated, or treated with either phosphonacetic acid or gancyclovir at a concentration sufficient to inhibit viral replication (Huang, 1975; Crumpacker, 1996). Two days later these cells were challenged with either anti-Fas antibody+CHX or TNF-α+CHX (FIGS. 3A and 3B). Although nearly all non-infected MRC-5 cells underwent apoptosis, irrespective of the presence or absence of phosphonacetic acid or gancyclovir, a major fraction of cells exposed to HCMV survived the challenge with the apoptotic stimuli in the absence of the viral DNA polymerase inhibitors. Further, a somewhat smaller but still large fraction of cells survived in the presence of the inhibitors. Thus, the insensitivity of HCMV-infected cells to apoptosis was not abolished by these drugs. These results indicate that the gene(s) responsible for this resistance to apoptosis is transcribed early in the course of the viral replication.

Example 5

Determination that the Infection of MRC-5 Fibroblasts with HCMV does not Lead to the Disappearance of Fas from the Surface of Infected Cells.

HCMV-infected cells can become insensitive toward anti-Fas antibody-induced apoptosis if the cells no longer express Fas on the cell surface, or if the expression of Fas in HCMV-infected cells is lost following exposure of the cells to CHX. However, the present inventors found that the infection of MRC-5 fibroblasts with HCMV does not lead to the disappearance of Fas from the surface of infected cells.

Figure 4A:
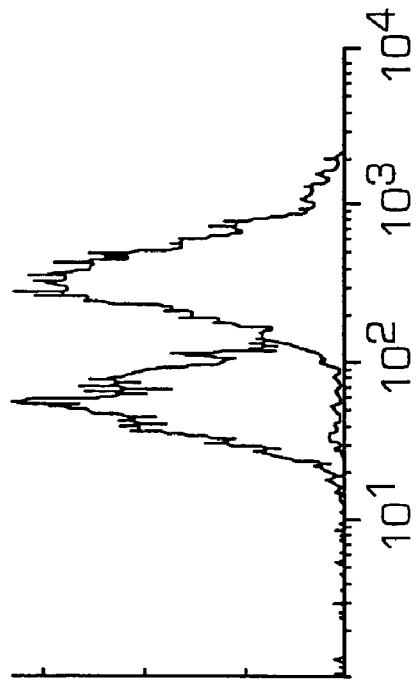
FIGS. 4A-4D document expression of cell surface Fas on MRC-5 cells. Fas levels were examined on cells by flow cytometry, after staining with anti-Fas antibody and a secondary FITC-conjugated antiserum (filled histograms). In control samples, the primary antibody was omitted (open histograms). HCMV-infected cells were treated (FIG. 4D) or not treated (FIG. 4B) with CHX, and compared to non-infected cells treated (FIG. 4C) or not treated with CHX (FIG. 4A).
Figure 4B:
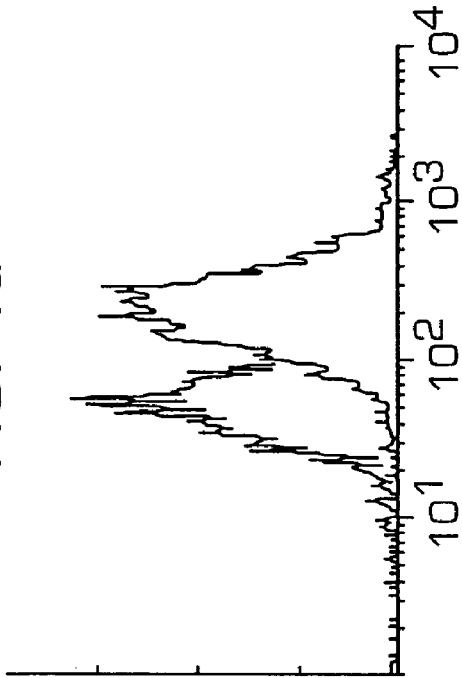
Figure 4C:
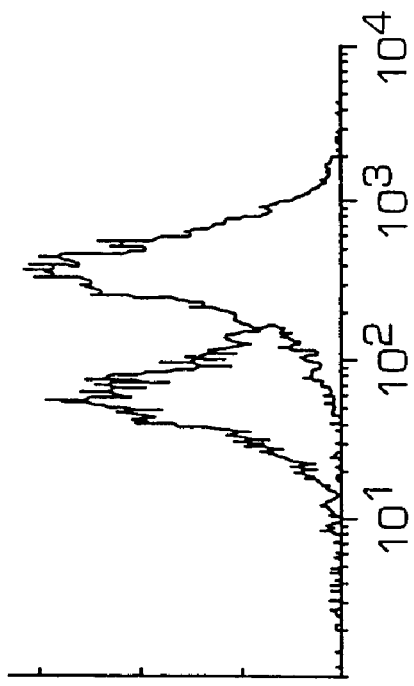
Figure 4D:
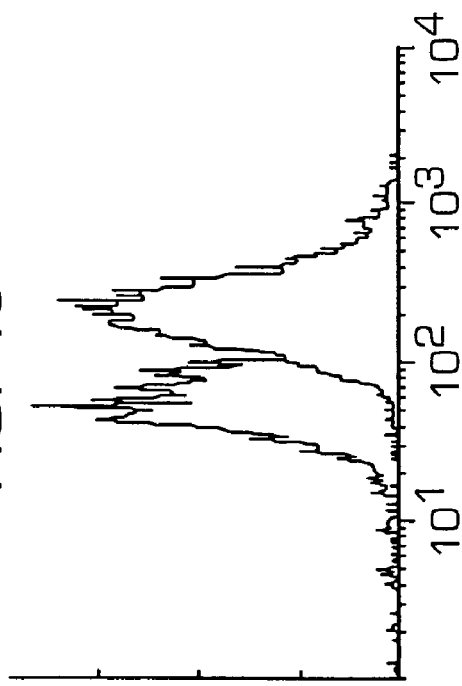

The expression of Fas on the surface of HCMV-infected cells (FIGS. 4B and 4D) treated (FIG. 4D) or not treated (FIG. 4B) with CHX was compared to those of non-infected cells (FIGS. 4A and 4C) treated (FIG. 4C) or not treated with CHX (FIG. 4A). The cells were incubated with anti-Fas antibody or a negative control, a non-specific IgM, at 4° C., for 20 min, then with FITC-labeled anti-murine IgM antiserum, and cell-associated fluorescence was examined on a flow cytometer. Expression of Fas antigen on the surface of HCMV-infected cells (FIGS. 4B and 4D) was only modestly diminished compared to that of non-infected MRC-5 cells (FIGS. 4A and 4C). Further, CHX-treated cells (FIGS. 4C and 4D) did not differ in their Fas-expression from the respective non-CHX-treated cells (FIGS. 4A and 4B).

Example 6

Determination that IE1 and IE2 do not Protect Cells Against Fas- and TNF-R1-Mediated Apoptosis, and Other HCMV Polypeptides are Responsible for the Resistance to Apoptosis.

It was previously reported that immediate early HCMV polypeptides IE1 and IE2 could protect HeLa cells against apoptosis induced by TNF-α or by a mutant adenovirus unable to express the E1B 19K polypeptide (Zhu et al., 1995, which is incorporated herein by reference). The present inventors set out to re-examine the anti-apoptotic activity of these two polypeptides.

HeLa cells were transiently co-transfected with an expression plasmid vector, pME18S, carrying a polynucleotide sequence encoding IE1 or IE2 (FIG. 5, "IE1" and "IE2," respectively), and a vector carrying the β-galactosidase gene (pCMVβ, Clontech). As a positive control, HeLa cells were transiently co-transfected with pCMVβ and a vector carrying a polynucleotide sequence encoding an anti-apoptotic polypeptide, such as the adenovirus E1B 19K or baculovirus p35. As a negative control, HeLa cells were transiently co-transfected with pCMVβ and a corresponding empty expression plasmid vector, pME18S, that does not carry a polynucleotide sequence encoding IE1, IE2, or a polypeptide having anti-apoptotic activity (control, empty vector).

Expression of IE1 (approx. 72 kDa) and IE2 (approx. 86 kDa) in the transfected HeLa cells was confirmed by Western blot analysis, by immunofluorescence visually examined under a fluorescence microscope, and by transactivation activity which led to an elevation of the vector-CMV-promoter-driven β-galactosidase expression which was increased 2- to 5-fold, as measured by a β-galactosidase ELISA (data not shown). Apoptosis was induced by incubating the transfected cells for 24 h with either TNF-α+CHX, or anti-Fas antibody+CHX. The surviving cells were stained with X-gal, a chromogenic substrate of β-galactosidase, and then the blue-stained cells were scored (FIG. 5).

Nearly all cells transfected with the empty vector were killed. Neither the presence of IE1 nor IE2 offered any protection. In contrast, significant fractions of cells transfected with either E1B 19K or p35 survived. Thus, results of the experiments performed by the present inventors do not support the results of Zhu et al. (1995) that IE1 and IE2 polypeptides can protect HeLa cells against TNF-α-induced apoptosis. Similarly, the present inventors found that IE1 and IE2 polypeptides did not protect HeLa cells against anti-Fas antibody-induced apoptosis. However, HCMV-infection does protect cells from both apoptotic stimuli. Taken together, these data suggest that HCMV polypeptides, other that IE1 and IE2, are responsible for the protection of cells against apoptosis.

Example 7

Identification of UL37 as an HCMV Gene Encoding Anti-Apoptotic Activity, and Methods of Screening for Genes and Gene Products Having Anti-Apoptotic Activity.

To identify HCMV genes that can suppress apoptosis induced by Fas-ligation, the present inventors established a transient transfection assay in HeLa cells. The HeLa cells can be transfected at much higher efficiency than MRC-5 cells and are similar in their sensitivity towards anti-Fas antibody and TNF-α treatment. Enhanced survival of HeLa cells following anti-Fas antibody+CHX treatment was detected by elevated β-galactosidase (β-gal) levels produced by a transfected β-gal marker plasmid. In control experiments, transfection of known viral and cellular anti-apoptotic genes, including E1B19K, baculovirus p35, and Bcl-$x_L$, yielded enhanced β-gal levels even when the plasmids encoding anti-apoptotic genes were diluted several hundred fold.

A genomic HCMV expression library was constructed, divided into pools of approximately 500 clones, and screened for anti-apoptotic activity in the HeLa transfection assay. Pools that produced the highest β-gal expression were divided into sub-pools of lower complexity which were evaluated in a similar test, and, finally, individual plasmids with the highest anti-apoptotic activity were isolated. Three primary pools each yielded a plasmid, #176, #206, and #135, with a strong anti-apoptotic activity, and the DNA sequence for the HCMV DNA inserts in these three plasmids was determined (FIG. 6A). All three inserts span a region of the HCMV genome which contains exon 1 of the UL37 gene, coding for a non-spliced gene product of UL37 (Tenney and Colberg-Poley, 1991, a and b, which are both incorporated herein by reference). Corresponding transcripts have been detected in HCMV infected cells (Colberg-Poley, 1996 which is incorporated herein by reference) and were predicted to encode a polypeptide of 163 amino acids, which the present inventors have designated as pUL37$_S$.

To confirm that pUL37$_S$ is responsible for the anti-apoptotic activity encoded by the genomic HCMV fragments in these plasmids, a DNA segment encompassing just the pUL37$_S$ open reading frame (ORF) was generated by PCR from HCMV (AD 169) genomic DNA and cloned into a eukaryotic expression vector. Either the unmodified pUL37$_S$ (not shown), or the pUL37$_S$ fused at its C-terminus with a c-myc-epitope tag was found to protect against Fas-mediated apoptosis in transiently transfected HeLa cells (FIG. 6B). The polypeptide pUL37$_S$ also inhibited TNF-α induced apoptosis in equivalent assays (not shown). The protection afforded by pUL37$_S$ expression was as great (or greater) than that provided by E1B19K or p35. Deletion of amino acids 2 to 23 of pUL37$_S$ abrogated its ability to block Fas-mediated cell death (pUL37$_S$Δ2-23; FIG. 6B), indicating that these amino-terminal residues are essential for the anti-apoptotic function of pUL37$_S$. IE1 and IE2, two HCMV genes previously reported to suppress apoptosis (Zhu and Shenk, 1995 which is incorporated herein by reference), did not exhibit anti-apoptotic activity, either alone, or in combination, in this assay (FIG. 6B), and were not isolated in the HCMV genomic expression screen.

Example 8

Identification of UL36 as an HCMV Gene Encoding Anti-Apoptotic Activity

The genomic HCMV expression library described in Example 7 above also yielded two primary pools with a strong anti-apoptotic activity, both containing HCMV DNA inserts spanning a similar region of the HCMV genome (AD169 nucleotides 47,532-49,917 and AD169 nucleotides 48,241-49,917). Both inserts span a region of the HCMV genome which encompasses the coding region of the previously described protein product of the CMV immediate early gene UL36 (Colberg-Poley, 1996; Patterson et al., 1999, which are both incorporated herein by reference).

To confirm that pUL36 is responsible for the anti-apoptotic activity encoded by the genomic HCMV fragments in these plasmids, a DNA segment encompassing just the pUL36 open reading frame (ORF) was generated by PCR from HCMV (AD 169) genomic DNA and cloned into an eukaryotic expression vector, with a c-myc-epitope tag at its C-terminus. A genomic DNA segment spanning just the UL36 coding region of CMV$_{AD169\text{-}early}$ (a pre-1982 passage of CMV$_{Ad169}$) was generated by PCR and cloned into the mammalian expression vector pcR3.1. To isolate a cDNA clone of the UL36 coding region, 293T cells were transfected with gUL36$_{AD169\text{-}early}$/pcR3.1, and UL36 cDNA was generated by RT-PCR and cloned into pcDNA3myc (denoted UL36$_{AD169\text{-}early}$myc/pcDNA3) to code for a carboxy terminus myc-tagged protein. Cells were transfected with empty vectors (pcR3.1 and pcDNA3), gUL36$_{AD169\text{-}early}$/pcR3.1 and UL36$_{AD169\text{-}early}$myc/pcDNA3, and then assayed for their ability to block Fas-mediated cell death.

Figure 7A:
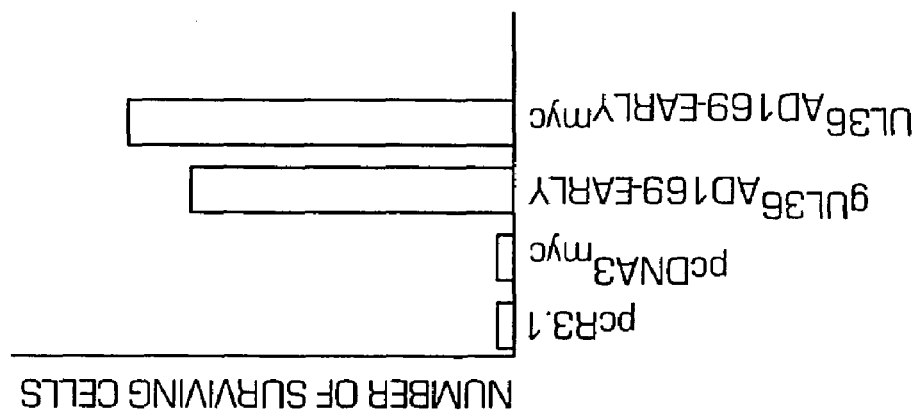
FIG. 7A is a histogram showing the number of surviving cells wherein the cells were transiently transfected with expression plasmids (1 μg) encoding genomic DNA including gUL36$_{AD169-early}$/pcR3.1 (column 3), UL36$_{AD169-early}$-myc/pcDNA3 (column 4), pcR3.1 (empty vector control, column 1), or pcDNA3myc (empty vector control, column 2), permitted to express the vector-encoded proteins for 24 hours, exposed to anti-Fas antibody+CHX for an additional 24 h, and then scored under a microscope for surviving cells.

Both gUL36$_{AD169\text{-}early}$/pcR3.1 and UL36$_{AD169\text{-}early}$myc/pcDNA3 protected HeLa cells against Fas-mediated apoptosis in transient transfection assays (FIG. 7A, lanes 3 and 4), whereas empty vectors conferred no protection (lanes 1 and 2), demonstrating that the UL36 gene was responsible for the anti-apoptotic function of the plasmids isolated from the CMV genomic library.

Example 9

Identification of Other UL37 Encoded Polypeptides Having Anti-Apoptotic Activity, and Methods of Screening for and Identifying Polypeptides Having Anti-Apoptotic Activity.

Alternative splicing of the UL37 gene produces a larger polypeptide consisting of exons 1, 2, and 3, which has been detected in HCMV-infected cells (Al-Barazi and Colberg-Poley, 1996, which is incorporated herein by reference). The present inventors tested whether this polypeptide, designated here as pUL37$_L$ (L stands for "long"), also suppresses apoptosis mediated by Fas. A cDNA corresponding to the pUL37$_L$ ORF was generated by RT-PCR from mRNA isolated from HCMV-infected MRC-5 cells and cloned into a eukaryotic expression vector. In the process of cloning pUL37$_L$ cDNA, the present inventors isolated a previously undescribed UL37 splice variant, encoding a polypeptide which the present inventors designated pUL37$_M$ (M stands for "medium") (FIG. 6C).

All three UL37 variants exhibited anti-apoptotic activity when tested for their ability to protect transiently transfected HeLa cells against Fas-mediated apoptosis (FIG. 6C). pUL37$_S$ consistently showed the strongest activity, although the relative expression levels of these polypeptides in the transfected cells were not examined. The present inventors note that the first 162 N-terminal amino acids encoded by exon 1 are shared by all three polypeptides, and these amino acids constitute virtually the entire length of pUL37$_S$.

Example 10

Determination that HeLa Clones that Continuously Express pUL37$_S$ are Resistant to Diverse Apoptotic Stimuli, and Methods of Screening for Genes and Gene Products Stably Expressed in Cells, that Confer Resistance to Apoptosis.

Figure 8B:
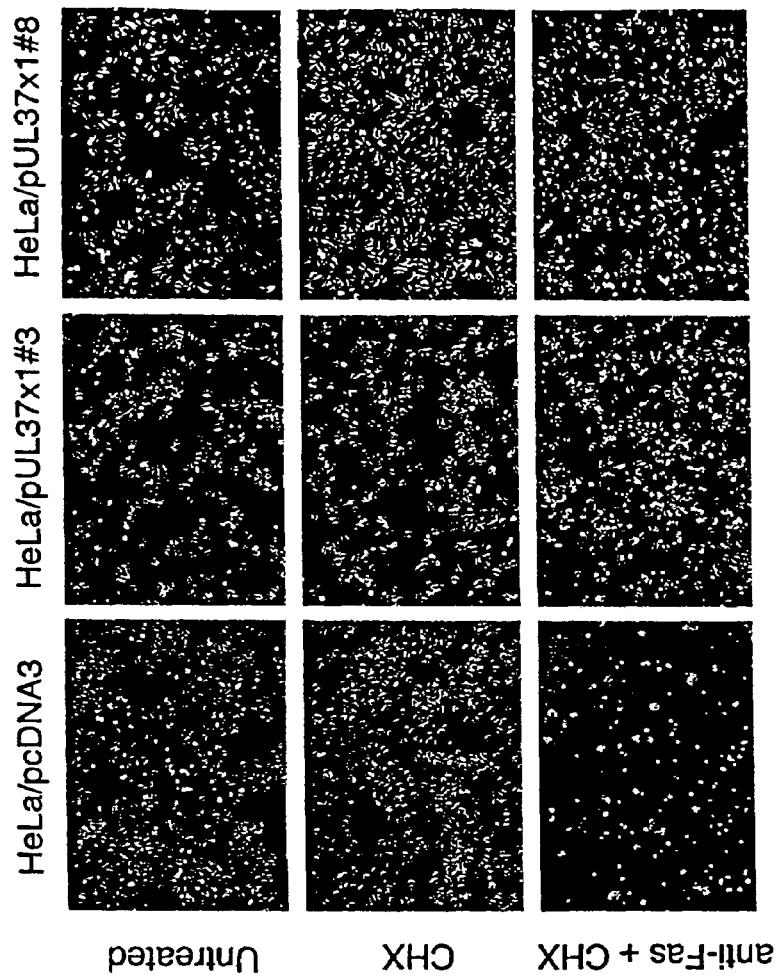
FIG. 8B is a set of six photographs showing surviving HeLa cells, constitutively expressing the pUL37$_S$myc polypeptide (expressed from HeLa cell clones "HeLa/pUL37x1#3" and "HeLa/pUL37x1#8") or not expressing pUL37$_S$ ("HeLa/pcDNA3" empty vector control), that were exposed to anti-Fas antibody+CHX for 24 h, or culture medium alone ("Untreated"), then photographed under a phase microscope.
Figure 8A:
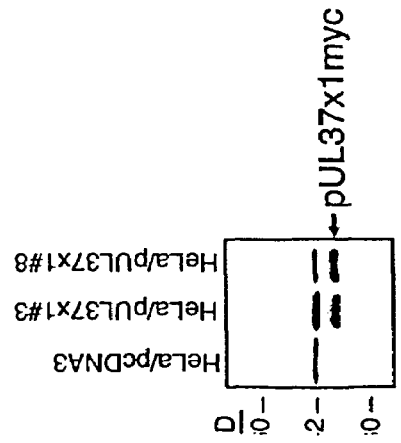
FIG. 8A is a photograph of a Western blot analysis of pUL37$_S$myc expression in HeLa cells, stably transfected with UL37$_S$myc, using the 9E10 anti-myc antibody for detection. "HeLa/pUL37x1#3" and "HeLa/pUL37x1#8" are two separate HeLa cell clones transfected with the UL37$_S$myc gene. "HeLa/pcDNA3" is a HeLa cell clone transfected with the empty vector.

Three transfected G418-resistant HeLa clones were isolated that stably express pUL37$_S$myc (designated HeLa/UL37x1myc #3, #8, and #N1), as detected by Western blot analysis with the 9E10 anti-myc antibody (Evan et al., 1985, which is incorporated herein by reference) (FIG. 8A). In parallel, three HeLa clones were isolated following stable transfections with the pcDNA3 vector alone (designated HeLa/pcDNA3-A, -B, and -C). All three HeLa/UL37$_S$myc cell lines were found to be resistant to Fas- and TNF-R1-mediated apoptosis, while the three HeLa/pcDNA3 clones were sensitive. A representative experiment is shown in FIG. 8B. While virtually all of the HeLa/pcDNA3-A control cells died following an overnight exposure to anti-Fas antibody+CHX or TNF-α+CHX, only a small fraction of the pUL37$_S$myc-expressing cells underwent apoptosis after an overnight exposure to these agents (FIG. 8B). Moreover, most of the pUL37$_S$myc-expressing cells continued to survive for more than 3 days of culturing in the presence of either anti-Fas antibody+CHX or TNF-α+CHX.

The present inventors tested whether pUL37$_S$ can inhibit apoptosis triggered by other stimuli. Expression of pUL37$_S$ in HeLa cells caused significant delay in the onset of apoptosis induced by infection with the E1B 19K-deficient adenovirus mutant Ad2$_{d1250}$ (FIG. 8C) (Subramanian et al., 1984, which is incorporated herein by reference), which is an apoptotic stimulus reported to be inhibited by HCMV infection (Zhu and Shenk, 1995, which is incorporated herein by reference). In addition, HeLa cells expressing pUL37$_S$myc were substantially more resistant to apoptosis induced by the anti-cancer drug doxorubicin (FIG. 8D). Thus, pUL37$_S$ is a broadly acting inhibitor of apoptosis that can inhibit or diminish cell death induced by a variety of cytotoxic agents.

Example 11

Detection of the Binding of pUL37$_S$ to Polypeptides Involved in Apoptotic Signaling Pathways, and Methods of Screening for Compounds that Bind to and Interact with Polypeptides Having Anti-Apoptotic Activity.

Figure 9:
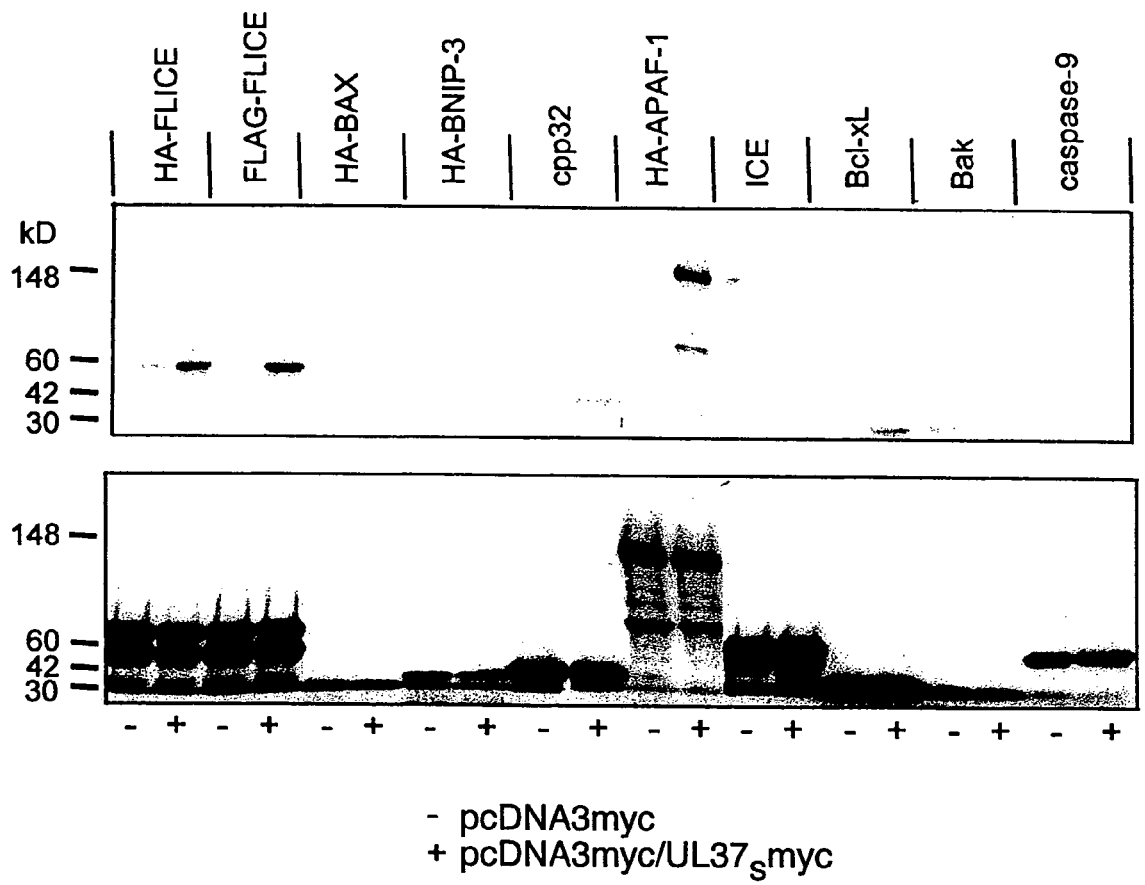
FIG. 9 is an image of polypeptides resolved on a gel showing that, compared to the control agarose beads (lower image), the agarose beads with immobilized pUL37$_S$ specifically bound FLICE (pro-caspase 8), Bax, BNIP-3, caspase 3 ("cpp32"), Apaf-1, ICE, Bcl-x$_L$, and Bak, but not caspase 9 (upper image).

The polypeptide pUL37$_S$ was expressed by transiently transfecting 293T cells with pcDNA3myc/UL37$_S$ plasmid. Control cells were transfected with pcDNA3myc plasmid. Two days after transfection, the cells were harvested, lysed in the presence of inhibitors of proteases, and anti-myc antibody was added. The antibody associated with pUL37$_S$myc (or unbound antibody in the control cell lysate) was then bound to protein G immobilized on agarose beads, and the beads containing bound antibody were aliquoted. These aliquots were then incubated with either in vitro translated HA-FLICE (FLICE fused to the epitope tag HA), FLAG-FLICE (FLICE fused to the epitope tag FLAG), HA-Bax (Bax fused to the epitope tag HA), HA-BNIP-3 (BNIP-3 fused to the epitope tag HA), caspase 3 (cpp32), HA-Apaf-1 (Apa-1f fused to the epitope tag HA), ICE, Bcl-$x_L$, Bak, or caspase 9, respectively. The incubated bead-protein complex was then washed extensively, and examined for binding of the in vitro translated polypeptides labeled with $^{35}$S-methionine. The control beads and the bead-protein complex were each boiled in SDS-PAGE sample buffer and analyzed by SDS-PAGE. The results are shown in FIG. 9. The upper image of FIG. 9 shows that, compared to the control beads, immobilized pUL37$_S$ specifically bound to FLICE, FLAG-FLICE, BAX, BNIP-3, caspase 3, Apaf-1, ICE, Bcl-$x_L$, and Bak, but did not bind to caspase 9. As a control, the lower image of FIG. 9 shows the migration of the respective in vitro translated polypeptides on the gel.

Example 12

Detection of the Binding of pUL36 to a Polypeptide Involved in Apoptotic Signaling Pathways To detect the binding of pUL36 to physiological molecules involved in the intracellular process of apoptosis, the polypeptide pUL36 was expressed by stably transfecting BJAB cells with pUL36myc/pcDNA3, followed by selection with G418. Control cells were transfected with pcDNA3myc plasmid. Expression of pUL36 was confirmed by Western blot analysis with the 9E10 anti-myc antibody.

BJAB/pcDNA3myc cells and BJAB/UL36myc cells were treated for 24 hours with either anti-Fas, or were left untreated. Cells were lysed in 150 mM NaCl, 5 mM EDTA, 50 mM Tris-HCl, pH 8.0, 1% Triton-X100, in the presence of protease inhibitors, and centrifuged at 10,000 g at 4° C. for 10 min. The supernatants were first pre-cleared with ethanolamine-treated Affi-Prep 10 beads (Bio-Rad), then incubated with 9E10 antibody covalently linked to Affi-Prep-10 beads, and washed with the lysis buffer. Cell extracts for Western blot analysis were prepared by standard procedures (Goldmacher et al., 1999). The immunoprecipitates were separated under reduced conditions by SDS-PAGE after being loaded at equal protein amounts per well, and analyzed by a standard Western blot protocol using the ECL detection system (Amersham). Pro-caspase 8 was detected using 5F7 anti-human caspase 8 (Upstate Biotechnology), followed by HRP anti-mouse IgG$_{2b}$ (Roche). Anti-FADD antibodies (Pharmingen) were used as a comparison, detected with HRP goat anti-mouse IgG (Amersham).

Figure 10A:
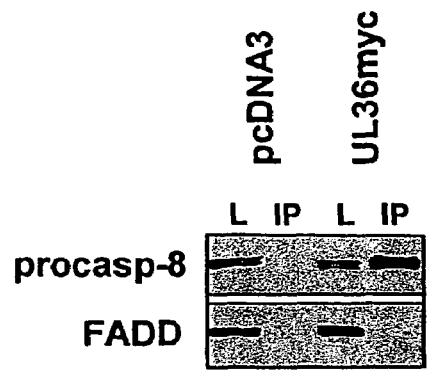
FIG. 10A is the result of a Western blot analysis. BJAB cells were transfected with pcDNA3myc (lanes 1 and 2) or UL36myc (lanes 3 and 4). Cell lysates ("L") and immunoprecipitates ("IP") were probed with anti-caspase 8 antibodies (upper row) or anti-FADD antibodies (lower row).

FIG. 10A shows the results of the Western blot analysis. Pro-caspase 8 was detected on the pUL36-containing beads (lane 4), but not on the control beads (lane 2), while the lysates from all these cells contained similar amounts of pro-caspase 8 (compare lanes 1 and 3). In contrast, while FADD was detected in approximately equal amounts in the lysates of both cell types (compare lanes 1 and 3), it was not found to be bound by the pUL36-containing beads (lanes 2 and 4). The size of the band detected by the anti-caspase 8 antibodies indicated that the pro-form of the protein was bound by pUL36, and not the mature form of the protein. To test this hypothesis, 293T cells were co-transfected with pUL36$_{AD169\text{-}early}$myc and with a truncated pro-caspase 8, containing only its HA-tagged pro-domain region. pUL36$_{AD169\text{-}early}$myc is expressed by a fusion gene comprising a UL36 ORF isolated from a pre-1982 passage of CMV$_{AD169}$ and the carboxy-linked myc epitope tag. The cells were lysed as above, and anti-HA antibody was used to immunoprecipitate the caspase 8 pro-domain. Anti-myc antibodies were then used to probe a Western blot for the inclusion of pUL36 with the immunoprecipitated material. Control cells were transfected with pUL36$_{AD169\text{-}early}$myc with either the empty vector (negative control), or with HA-tagged pro-caspase 8 (positive control). Additional cells were co-transfected with the non-functional mutant pUL36$_{AD169\text{-}ATCC}$myc with either the HA-pro-domain, the empty vector or HA-pro-caspase 8. The results are set forth in FIG. 10B.

Figure 10B:
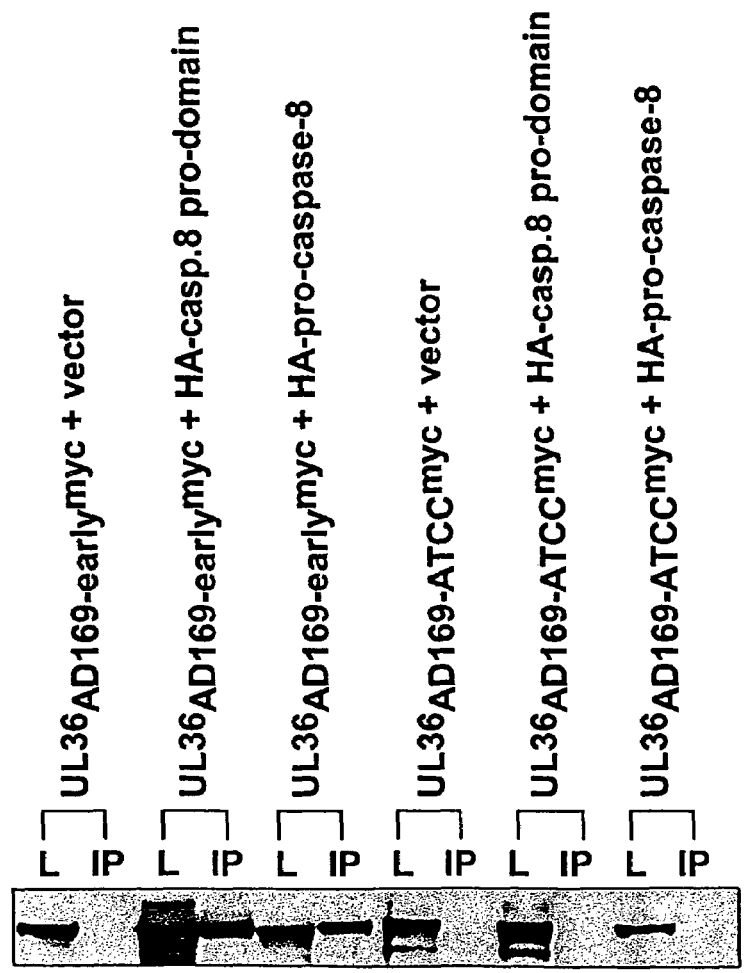
FIG. 10B is the result of a Western blot analysis. 293T cells were co-transfected with pUL36$_{AD169-early}$myc and one of the following three vectors: an empty vector (lanes 1 and 2), truncated pro-caspase 8, containing only its HA-tagged pro-domain region (lanes 3 and 4), or HA-tagged full-length pro-caspase 8 (lanes 5 and 6). Other 293T cells were co-transfected with pUL36$_{AD169-ATCC}$myc and one of the following three vectors: an empty vector (lanes 7 and 8), the HA-tagged caspase 8 pro-domain (lanes 9 and 10), or HA-tagged full-length pro-caspase 8 (lanes 11 and 12). Each transfectant was lysed and subjected to immunoprecipitation with anti-HA antibodies. The complexes were separated by SDS-PAGE, and transferred to nitrocellulose. The blots were probed with anti-myc antibodies to identify with which portions of pro-caspase 8 the pUL36 polypeptide associated (lanes 2, 4, 6, 8, 10 and 12). Lysates were also produced from the transfectants and probed on the Western blot with anti-myc antibodies for expression of pUL36 (lanes 1, 3, 5, 7, 9 and 11).

Functional pUL36 co-precipitated with the pro-domain of caspase 8 (FIG. 10B, lane 4), as well as with the full-length pro-caspase 8 (FIG. 10B, lane 6), but not the empty vector (FIG. 10B, lane 2). The non-functional form of pUL36 did not co-precipitate with either of the proteins (FIG. 10B, lanes 10 and 12).

Example 13

Determination that Deletion-Mutant Polypeptides of pUL37$_S$, Lacking Anti-Apoptotic Activity, Inhibit or Greatly Diminish the Anti-Apoptotic Activity of pUL37$_S$.

Mutants of pUL37$_S$, pUL37$_S$Δ131-147 and pUL37$_S$Δ115-130 (also called pUL37x1Δ131-147 and pUL37x1Δ115-130, respectively), were constructed by deleting the sequence from pcDNA3/UL37$_S$myc encoding amino acids 131-147 and 115-130, respectively. Thus, deletion mutants pUL37$_S$Δ131-147 and pUL37$_S$Δ115-130, are identical to pcDNA3/UL37$_S$myc except that the sequence encoding amino acids 131-147 and 115-130, respectively, have been deleted.

Figure 11A:
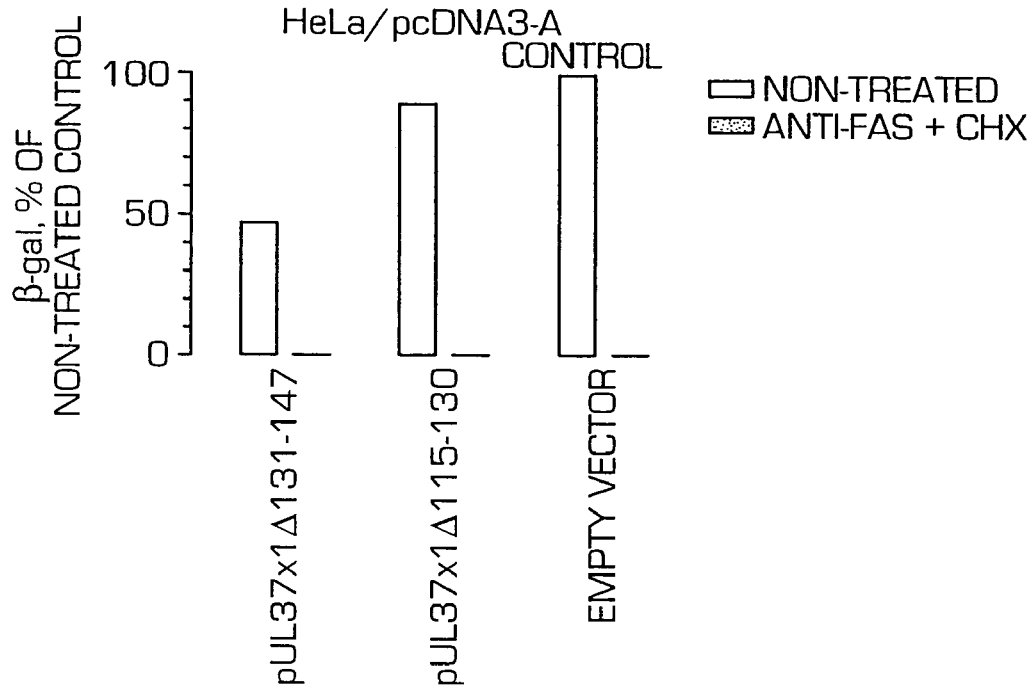
FIGS. 11A and 11B are histograms showing the results of a Western blot analysis of polypeptides expressed in the HeLa cell line, HeLa/UL37x1#3 ("HeLa/UL37#3"), that constitutively expresses pUL37$_S$myc polypeptide (FIG. 11B), and a control HeLa cell line, HeLa/pcDNA3-A, that does not constitutively express an anti-apoptotic polypeptide (FIG. 11A). Each cell line was transiently co-transfected with a β-galactosidase expression plasmid and an eukaryotic expression plasmid vector carrying either deletion mutant pUL37x1Δ131-147, deletion mutant pUL37x1Δ115-130, or the control, pcDNA3myc ("empty vector"). 24 h after co-transfection, the cells were either exposed for an additional 24 h to anti-Fas antibody in the presence of CHX ("anti-Fas+CHX") (FIGS. 1A and 1B, closed bars) or left untreated (FIGS. 11A and 11B, open bars). The surviving cells were then quantified by determining the β-galactosidase levels via an ELISA by detecting β-galactosidase protein.
Figure 11B:
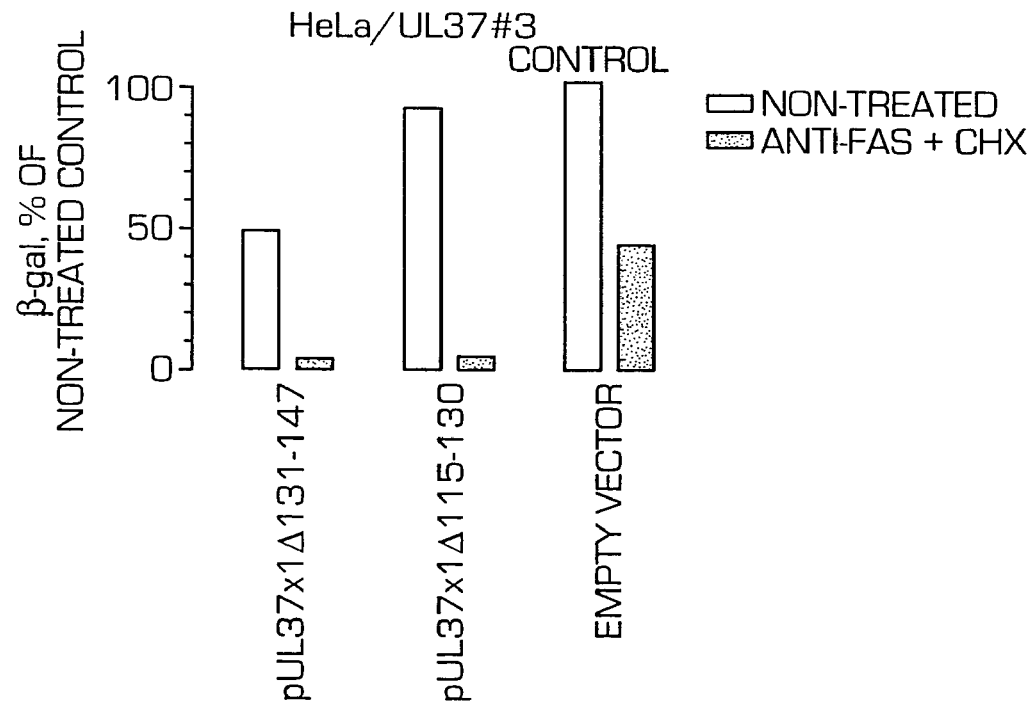

HeLa/UL37x1#3, a HeLa cell line that constitutively expresses pUL37$_S$myc polypeptide and a control, HeLa/pcDNA3-A, a HeLa cell line that does not constitutively express an anti-apoptotic polypeptide, were each co-transfected with a beta-galactosidase expression plasmid and, also, a eukaryotic expression plasmid vector carrying either a deletion mutant or an empty vector (pcDNA3myc, control). 24 h after co-transfection, the cells were either exposed for an additional 24 h to anti-Fas antibody, in the presence of cyclohexamide (FIGS. 11A and 11B, closed bars) or left untreated (FIGS. 11A and 11B, open bars). The surviving cells were than quantified by determining the β-galactosidase levels with a β-galactosidase ELISA (Boehringer Mannheim). The results of the Western blot analysis show that both of the deletion mutants greatly diminish the pUL37$_S$myc-induced resistance of HeLa/UL37x1#3 cells towards Fas-mediated apoptosis. The control HeLa/pcDNA3-A cells were sensitive to Fas-mediated apoptosis, and this sensitivity was not affected by the expression of the deletion mutants. The results show that the deletion mutants have lost the anti-apoptotic activity of the wild-type pUL37$_S$, and that they specifically inhibit or diminish the anti-apoptotic activity of pUL37$_S$.

Example 14

Determination of Domains within pUL37$_S$ Required for Anti-Apoptotic Activity

To identify the functional domains within the HCMV anti-apoptotic polypeptide pUL37$_S$, a series of deletion mutants were generated that span the entire UL37$_S$ ORF (AD169 strain). To additionally track their intracellular localization, the pUL37$_S$ deletion mutants were expressed as carboxy-terminally myc-tagged proteins (Goldmacher et al., 1999).

Figure 12:
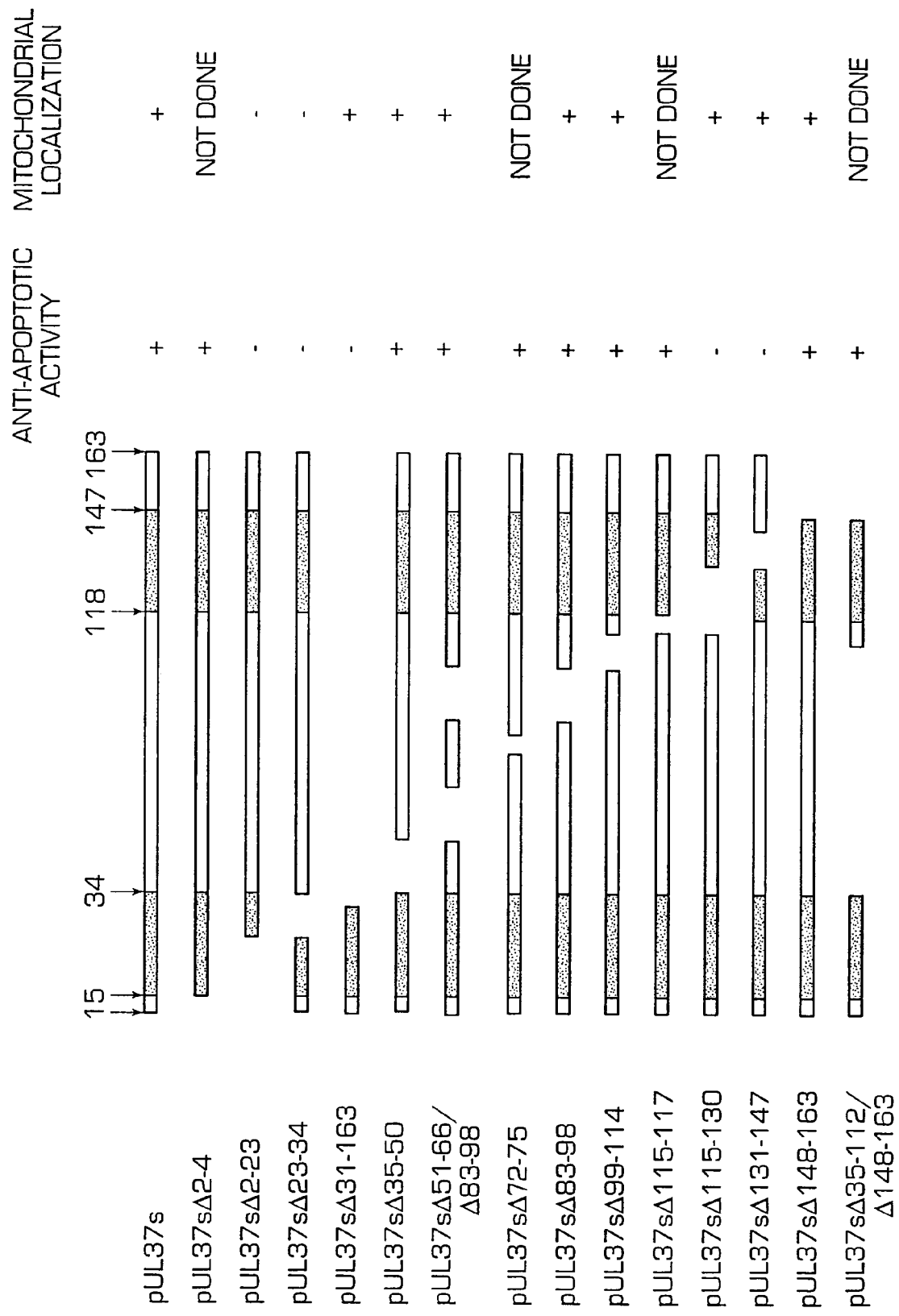
FIG. 12 is a chart showing the pUL37$_S$ deletion mutant polypeptides. Fourteen deletion mutants were constructed, and are shown aligned below the native pUL37$_S$ protein ("pUL37x1"). Solid regions indicate the domains of the native pUL37$_S$ protein required for anti-apoptotic activity, also noted above the native protein via arrows as extending between amino acid residues 5-34 and 118-147. The amino terminal (1) and carboxy terminal (163) amino acids are also indicated on the native protein. Gaps in each mutant indicate the approximate area in which the deletion occurred.

HCMV DNA was purified from HFF cells infected with HCMV (strain AD169), originally obtained from the American Type Culture Collection (ATCC), as previously described (Lesperance et al., 1998). UL37x1, encoding wild-type pUL37$_S$, was cloned into the pcDNA3 eukaryotic expression vector. Deletion mutagenesis was performed using the GeneEditor™ in vitro site-directed mutagenesis system (Promega) and the QuikChange™ site-directed mutagenesis kit (Stratagene). Fourteen deletion mutants were constructed, as shown in FIG. 12.

The deletion mutants were transiently expressed in HeLa cells, cultured in DMEM supplemented with 10% fetal bovine serum, and assayed for their ability to block Fas- or TNF-R1-mediated apoptosis. Transfections and apoptosis assays were performed as previously described (Goldmacher et al., 1999). Briefly, cells were transiently transfected with the expression vectors (purified with a Qiagen plasmid purification kit) using SuperFect transfection reagent (Qiagen) in accordance with the manufacturer's protocol. After 24 hours, cells were exposed to anti-Fas 7C11 antibody (Coulter, 0.5 μg/ml)+cyclohexamide (Sigma, 10 μg/ml) for 24 hours.

After treatment with anti-Fas+CHX, a portion of the cells were scored under a phase microscope. The results of these experiments are shown in FIG. 12. The deletion of amino acids 2-23 or amino acids 23-34 resulted in a complete loss of the anti-apoptotic activity of pUL37$_S$, while the deletion of amino acids 2-4, or amino acids 35-50 did not abolish anti-apoptotic function. This result indicated that the 5-34 amino acid segment contains a domain required for the anti-apoptotic activity of pUL37$_S$. Similarly, the results obtained with mutants Δ115-117 (fully functional), Δ115-130 (inactive), Δ131-147 (inactive), and Δ148-163 (fully functional) indicated that the 118-147 amino acid segment contains a second domain required for the anti-apoptotic activity of pUL37$_S$. None of the deletions between amino acids 35-117 abolished anti-apoptotic activity of pUL37$_S$, indicating that the entire 35-117 amino acid region is dispensable for anti-apoptotic function. Remarkably, a mini-protein pUL37$_S$Δ35-112/Δ148-163, consisting just of the two functional domains, retained anti-apoptotic function. Taken together, the properties of the deletion mutants indicate that two segments of the amino acid sequence of pUL37$_S$, amino acids 5-34, and amino acids 118-147, contain two domains necessary and sufficient for anti-apoptotic function.

Another portion of the treated cells was used to determine intracellular localization of the deletion mutants. Cells expressing the deletion mutants and wild-type controls were stained with 9E10 anti-myc antibody and counterstained with anti-human mitochondria antibody (Immunovision), mitotracker dye (a mitochondrial marker, Molecular Probes), or with one of the following endoplasmic reticulum markers: anti-calnexin (rabbit polyclonal), anti-calreticulin (rabbit polyclonal), or anti-PDI (mouse monoclonal, Mab 1D3), each from StressGen.

The immunofluorescence analysis revealed that the mutant lacking amino acids 22-23 did not co-localize with mitochondrial markers, and that the mutant lacking amino acids 23-34 at best marginally, if at all, co-localized with mitochondrial markers (FIG. 12). In contrast, a mutant lacking all but the first 30 amino acids did co-localize with the mitochondrial markers (FIG. 12). This result indicated that the mitochondrial localization signal of pUL37$_S$ is located within the domain comprising amino acids 2-30.

Example 15

Determination of Inactivating Mutations in the UL36 Polynucleotide

A number of strain-dependent variations in the predicted amino acid composition of pUL36 proteins has been noted (Patterson and Shenk, 1999). The gene encoding pUL36 from five variants was sequenced and the alignment is set forth in FIG. 13. The five variants were a recent HCMV clinical isolate denoted pUL36$_{Toledo}$, an early (pre-1982) passage of HCMV strain AD169 denoted pUL36$_{AD169-early}$, a later passage of AD169 obtained from the American Type Culture Collection denoted pUL36$_{AD169\ early-ATCC}$, HCMV strain Towne denoted pUL36$_{Towne}$, and a subclone of HCMV strain Towne denoted pUL36$_{Towne-RIT}$. The comparison revealed that pUL36$_{AD169-ATCC}$ differs from pUL36 encoded by each of the other four strains by a single amino acid substitution Cys$^{131}$→Arg$^{131}$. The sequences of pUL36 encoded by pUL36$_{Towne}$, pUL36$_{AD169-early}$ and pUL36$_{Toledo}$ were nearly identical, while pUL36$_{Towne-RIT}$ has a large deletion/rearrangement between Leu$^{156}$ and His$^{295}$.

To determine if the variations affected the anti-apoptotic activity of the pUL36 polypeptide, genomic DNA segments spanning just the UL36 coding regions of HCMV strains pUL36$_{AD169-early}$, pUL36$_{AD169-ATCC}$, pUL36$_{Towne}$, and pUL36$_{Towne-RIT}$ were generated and cloned into an expression vector. The anti-apoptotic activities of the protein expressed by each of the vectors was compared using the procedure set forth in Example 8.

The results of the comparison are shown in FIG. 14 and demonstrate that while both pUL36$_{AD169-early}$ and pUL36$_{Towne}$ are effective death suppressors in this experiment, their respective variants pUL36$_{AD169-ATCC}$ and pUL36$_{Towne-RIT}$ completely lacked anti-apoptotic activity.

Example 16

Determination of the Intracellular Localization of pUL37$_S$.

Immunofluorescence analysis of transiently transfected cells demonstrated that pUL37$_S$myc localized predominantly to mitochondria (FIG. 15A), as confirmed by its co-localization with a human anti-mitochondrial autoimmune serum (FIGS. 15B and 15C) and MitoTracker dye (not shown). The pUL37$_S$Δ2-23myc mutant exhibited a markedly altered perinuclear staining pattern with some plasma membrane localization (FIG. 15D) and did not co-localize with mitochondrial markers, indicating that the N-terminal 23 amino acid segment of pUL37$_S$ is necessary for both anti-apoptotic activity and mitochondrial targeting. Immunoelectron microscopy of HeLa/pUL37$_S$myc cells further revealed that pUL37$_S$myc was associated mainly with the outer mitochondrial membrane (two representative fields are shown in FIGS. 15E and 15F). The broad anti-apoptotic activity of pUL37$_S$ and its subcellular localization led the present inventors to designate this polypeptide as the "viral mitochondrial inhibitor of apoptosis" (vMIA).

Example 17

Determination that the Process of Fas-Mediated Apoptosis in pUL37$_S$-Expressing Cells is Initiated but Blocked at a Point Prior to Cytochrome c Release.

The impact of pUL37$_S$ on biochemical events involved in Fas-mediated apoptosis was examined by comparing control HeLa/pcDNA3 cells, which are sensitive to anti-Fas antibody plus CHX, to HeLa clones expressing either pUL37$_S$ or cellular Bcl-x$_L$, both of which are resistant to Fas-mediated apoptosis. Ligation of Fas triggers the recruitment and activation of caspase 8 through the adapter molecule FADD (Ashkenazi et al., 1998). This process was not impaired by pUL37$_S$ since pro-caspase 8 was processed in pUL37s-expressing cells similar to its processing in either Bcl-x$_L$-expressing cells, or control cells within 4 h of the exposure to anti-Fas antibody plus CHX, but not CHX alone (FIG. 16A). Fas-signaling is connected to mitochondrial events in apoptosis through Bid, a pro-apoptotic BH3 polypeptide that is proteolyzed by caspase 8 and subsequently translocates to mitochondria where it triggers cytochrome c release (Li et al., 1998; Lu et al., 1998). Exposure to anti-Fas antibody plus CHX triggered cleavage of Bid in both control and pUL37$_S$-expressing cells ("vMIA"), demonstrating that the proteolysis of Bid was not affected by pUL37$_S$ (FIG. 16B).

In contrast to the inability of pUL37$_S$ to prevent caspase 8 and Bid-processing, several other downstream events in Fas-mediated apoptosis were inhibited in pUL37$_S$-expressing HeLa cells. Following a 4 h exposure to anti-Fas antibody plus CHX, the control HeLa/pcDNA3 cells underwent efflux of mitochondrial cytochrome c into the cytoplasm, an event almost universally observed during apoptosis (Green and Reid, 1998). Cytochrome c release was not observed, however, in either the pUL37$_S$- or Bcl-x$_L$-expressing HeLa cells (FIG. 16B). Processing of procaspase 9, which depends upon cytochrome c release was also inhibited in pUL37$_S$- and Bcl-x$_L$-expressing cells, as was cleavage of PARP (FIG. 16B), a substrate of downstream effector caspases. Thus, pUL37$_S$ interferes with Fas-mediated apoptotic signaling in HeLa cells at a point upstream of cytochrome c release but downstream of caspase 8 activation and Bid processing.

pUL37$_S$ is expressed throughout infection and functions as a potent inhibitor of apoptosis, helping to explain the ability of infected cells to support productive HCMV replication over prolonged periods in the absence of cell death. The identification of pUL37$_S$ as a potent anti-apoptotic factor suggests two possible roles for this polypeptide during HCMV infection. pUL37$_S$ may counteract pro-apoptotic signals that are elicited within cells by viral DNA synthesis or gene expression, such as elevated levels of TNF-α, c-myc, and p53 (Smith et al., 1992; Geist et al., 1994; and Boldogh et al., 1998). In addition, expression of pUL37$_S$ may protect infected cells from immune surveillance by conferring resistance to Fas-, TNF-R1-, or granzyme B-mediated apoptosis, all major components for innate and adaptive immune responses (Smyth and Trapani, 1998).

The predominant localization of pUL37$_S$ to mitochondria, together with its impact on specific signaling events that occur in Fas-mediated cell death, argue for a mitochondrial mode of action for pUL37$_S$ in inhibiting or diminishing apoptosis. pUL37$_S$ inhibits or diminishes, either directly or indirectly, mitochondrial efflux of cytochrome c into the cytoplasm. This point of action at mitochondria, and the ability to inhibit apoptosis induced by diverse agents, are functional properties analogous to those of Bcl-2 and its homologs (Adams and Cory, 1998).

pUL37$_S$ does not share any notable homology with Bcl-2 and lacks sequences similar to BH1, BH2, BH3, and BH4 domains characteristic of known Bcl-2 family members. This suggests that pUL37$_S$ represents a distinct class of viral inhibitors of apoptosis outside of the previously described viral Bcl-2 homologs, FLIPs, and IAPs (Tschopp et al., 1998), raising the possibility that anti-apoptotic cellular counterparts to pUL37$_S$ exist.

The results of the experiments performed by the present inventors demonstrate that HCMV infection provides resistance to apoptosis induced by anti-Fas antibody or TNF-α, and that expression of pUL37$_S$ is sufficient to protect cells from these apoptotic stimuli. Ablation or inhibition of pUL37$_S$ function may sensitize infected cells to apoptosis and impair HCMV replication, thereby establishing a novel rationale for developing antiviral drugs directed against HCMV. Pharmaceutical compositions that interfere with, e.g., inhibit or diminish, the anti-apoptotic function of pUL37$_S$ may allow self-destruction of infected cells and/or facilitate their elimination by the immune system.

Example 18

Determination that pUL36 Prevents Activation of Caspase 8

During the signal transduction pathway that leads to apoptosis, after Fas binding by the Fas receptor, pro-caspase 8 is recruited to the ligand-receptor complex through the adapter molecule FADD. Pro-caspase 8 is then cleaved, releasing the active form of the molecule, caspase 8 (Ashkenazi and Dixit, 1998).

To determine the effect of the pUL36 polypeptide on Fas ligand binding mediated pro-caspase 8 activation, the stably transfected cell line BJAB/UL36myc and the control cell line BJAB/pcDNA3, were treated for 24 h with either anti-Fas antibodies or left untreated. Cell lysates were prepared, separated by SDS-PAGE, and blotted onto nitrocellulose. Pro-caspase 8, Bid and PARP were then detected by Western blot analysis, using 5F7 anti-human caspase 8 antibodies (Upstate Biotechnology), anti-human Bid C-20 antibodies (Santa Cruz Biotechnology) and C210 anti-PARP antibodies (Biomol), followed by detection with HRP-anti-mouse IgG$_{2b}$ (Roche), HRP-anti-rabbit IgG (Amersham) and HRP-goat-anti-mouse IgG (Amersham), respectively.

The results indicate that pUL36 interrupts the Fas-apoptotic signaling pathway at or upstream of caspase 8 activation (FIG. 17). As expected, two downstream events, processing of Bid, a caspase 8 substrate, and cleavage of PARP, a substrate of downstream effector caspases, were also inhibited in pUL36 expressing cells. These results, and others discussed above, have led to the further elucidation of the apoptotic signal transduction pathways (FIG. 18).

Example 19

Determination of the Effect of Dominant-Negative Mutants of pUL37$_S$

Deletion mutagenesis analysis of the open reading frame of UL37$_S$ (also referred to as UL37x1) identified two domains that are necessary and sufficient for its anti-apoptotic activity (see Example 14 above). These domains are confined within the segments between amino acids 5 and 34, and 118 to 147. Experiments were performed to determine whether a deletion in either of these two domains interfered with the anti-apoptotic function of full-length pUL37$_S$.

Apoptosis was induced in the cell line HeLa/UL37x1#3 (HeLa cells transfected with UL37x1, clone No. 3), that constitutively expresses pUL37$_S$myc and is resistant to apoptosis, through the addition of anti-Fas antibodies and cyclohexamide to the culture medium. To identify dominant-negative mutants, HeLa/UL37x1#3 cells were co-transfected with the lacZ (encoding β-galactosidase) indicator plasmid vector, together with either an expression vector for a pUL37$_S$ deletion mutant or the empty plasmid vector, pcDNA3. As an additional control, the HeLa cell line, HeLa/pcDNA3-A, carrying only the empty vector used in establishing HeLa/UL37x1#3, was also transfected with the pUL37$_S$ deletion mutant plasmids or the negative control vector, pcDNA3, as above.

One day after the transfection, cells were treated with anti-Fas antibody plus cyclohexamide for 24 h. Cell survival was then assessed by measuring spectrophotometrically the level of β-galactosidase expression, as described in Example 1. The results are shown in FIGS. 19A and 19B. As expected, HeLa/UL37$_S$#3 cells transfected with the empty vector were protected from apoptosis induced by anti-Fas plus cyclohexamide (about 40% β-gal signal compared to untreated cells; FIG. 19B, bars labeled "vector"), while control HeLa/pcDNA3-A cells were killed (virtually no signal; FIG. 19A). Neither the deletion mutant pUL37Δ2-23, nor the deletion mutant pUL37Δ23-34 made HeLa/UL37x1#3 cells more sensitive to apoptosis (FIG. 19B, bars labeled "delta2-23" and "delta23-34"). In contrast, both pUL37Δ115-130 and pUL37Δ131-147 mutants restored sensitivity of HeLa/UL37x1#3 cells to anti-Fas antibodies+cyclohexamide-induced apoptosis, acting as dominant-negative mutants (FIG. 19B, bars labeled "delta115-130" and "delta131-147"). As expected, in the control cell line HeLa/pcDNA3-A, none of the transfections had any significant effect on the survival of the cells upon treatment with anti-Fas antibody+cyclohexamide.

Example 20

Detecting the Expression of pUL37$_S$ in MRC-5 Fibroblasts Infected with HCMV.

The expression of pUL37$_S$ in MRC-5 fibroblasts infected with HCMV (Towne strain) was detected using a rabbit polyclonal antiserum raised against the 22 C-terminal amino acid peptide of pUL37$_S$. Samples of cells were infected with the virus and then lysed at 4, 8, 24, and 72 h post-infection. Proteins in the cell lysates were then separated by SDS-PAGE and analyzed by Western blot analysis. Detection was with horse radish peroxidase-labeled anti-rabbit IgG antiserum and the ECL method (Amersham). The results of the Western blot analysis demonstrate that expression of pUL37$_S$ becomes first detectable at 8 h post-infection and reaches maximal levels at 48 h post-infection (FIG. 20).

Materials and Methods

Cells and Viruses

Human lung MRC-5 fibroblasts (ATCC CCL 171) and HeLa cells (ATCC CCL 2) were purchased from American Type Culture Collection (ATCC), Rockville, Md. 293T cells were a gift from Dr. Garry Nolan, Stanford University. MRC-5 cells were used until passage 25. 293T cells (DuBridge et al., 1987, which is incorporated herein by reference) were purchased from Edge BioSystems, Gaithersburg, Md. Cells were cultured in DMEM supplemented with 10% fetal bovine serum. Human B cell line BJAB was a gift from Dr. E. Kieff.

The adenovirus mutant Ad2$_{d1250}$ (Subramanian et al., 1984, which is incorporated herein by reference) was a gift from Dr. G. Chinnadurai, St. Louis University. HeLa/Bcl-x$_L$ cells were generated by retroviral transduction of FLAG-tagged Bcl-x$_L$ into HeLa cells with subsequent cloning. HeLa/Bcl-x$_L$ cells constitutively express FLAG-tagged Bcl-x$_L$, as detected by Western blot analysis with the M2 anti-FLAG antibody (Kodak).

HCMV AD169 (ATCC VR-538) and Towne (ATCC VR-977) strains were purchased from ATCC. The viral stocks were isolated as follows. Using mother pool virus stock 108 human MRC-5 fibroblasts were infected with 0.001 plaque forming units (pfu) in 10 ml non-serum-supplemented DMEM in a roller bottle and incubated for 1 hr at 37° C. Medium was then replaced with 100 mL serum-supplemented fresh medium. Medium was changed every 4 days until 100% cells displayed cytopathic effect (CPE). The virus was harvested 5 days after reaching 100% CPE by shaking cells off the bottle and by scraping the remaining cells off into medium. The suspension was centrifuged for 60 min at 10,000 g, and the pellet was resuspended in 2 mL serum-free DMEM supplemented with 2 mL sterile skim milk. The resulting suspension was sonicated on wet ice, spun at 1,000 g for 5 min, and the supernatant containing virus was aliquoted and stored at −80° C.

Antibodies

Mouse monoclonal antibody MA810 reacting with both IE1 and IE2 polypeptides of HCMV and IE2 was purchased from Chemicon International, Temecula, Calif. Mouse monoclonal antibody 7C11 specific for human Fas (CD95) (Robertson et al., 1995, which is incorporated herein by reference) was purchased from Coulter Corp., Miami, Fla. Mouse monoclonal antibody 9E10 reactive with a human c-myc fragment, amino acids 410-419, was purchased from Oncogene Research Products.

Reagents

Cycloheximide (CHX) (Sigma, St. Louis, Mo.) was dissolved in PBS at 10 mg/mL, sterilized by filtering through a 0.22 mm filter and kept as a stock solution at 4° C. Phosphonoacetic acid (Sigma) was dissolved in PBS at 10 mg/mL and sterilized by filtering through a 0.22 mm filter before use. Recombinant human tumor necrosis factor-α (TNF-α) (Sigma, Cat. No. T 6674) was reconstituted in sterile water at 10 mg/mL and kept at 4° C. Gangcyclovir (Roche Laboratories, Nutley, N.J.) was dissolved in sterile water and kept at −20° C. Z-VADfmc was dissolved in dimethylsulfoxide to the concentration of 50 mM and kept at −20° C. This stock solution was added to cell culture to the final concentration of 80 mM.

Plasmids, Cloning, Transfection, and Retroviral Vector Gene Transduction

Cosmids containing parts of HCMV AD 169 genome, pCM1007, pCM1015, pCM1017, pCM1029, pCM1035, pCM1039, pCM1040, pCM1052, pCM1058, pCM1072 and covering the entire HCMV AD169 genome (Fleckenstein et al., 1982, which is incorporated herein by reference) were used for library constructions. Cosmid pON2601 (Cha et al., 1996, which is incorporated herein by reference) contains a part of the HCMV genome not represented in the AD169 strain.

Green Fluorescent Protein expressing vector pQBI 25 was purchased from Quantum Biotechnologies, Montreal, Canada. pCMVβ was purchased from Clontech, San Francisco, Calif. Human FLAG-Bcl-x$_L$/pcDNA3 was described previously (Chittenden et al., 1995, which is incorporated herein by reference). E1B19K/p/RC/CMV was a gift from Dr. G. Chinnadurai, St. Louis University. A myc-tagged version of baculovirus p35 was cloned into pcDNA3 using standard methods known to those skilled in the art.

The eukaryotic expression vectors pZeoSV2(+), pcDNA1.0, pcDNA3, pRC/CMV, pcDNA3.1(−)MycHis, and pCR3.1-Uni were purchased from Invitrogen, Carlsbad, Calif. Expression plasmids carrying IE1, pON2205 and IE2, pON2206 were described elsewhere (Jenkins et al., 1994, which is incorporated herein by reference). Expression of IE1 and IE2 in transfected HeLa cells was confirmed by Western blot analysis with the antibody MA810 (Chemicon) reacting with both IE1 and IE2 polypeptides of HCMV.

Expression plasmid pcDNA3myc, is a derivative of pcDNA3 (Invitrogen), which contains in its polylinker section a DNA sequence encoding three tandem copies of a human c-myc epitope (amino acids 410-419 of human c-myc, swissprot accession number P01106) for fusion at the carboxyl-terminus of proteins. This epitope is recognized by 9E10 monoclonal antibody (Evan et al., 1985) and can be purchased from Oncogene Research Products (Cat. No. OP10). The cDNA encoding pro- and anti-apoptotic polypeptides were subcloned into the eukaryotic expression vectors pcDNA3, pcDNA1.0, and/or pRC/CMV (Invitrogen) and/or their derivatives containing either N-terminal FLAG, N-terminal HA, or C-terminal myc peptide as described in the text of this application.

The $UL37_S$, $UL37_M$, $UL37_L$, and UL36 sequences were generated by PCR and cloned in various eukaryotic expression vectors as described in the text. The DNA sequence encoding $pUL37_S$ was generated by PCR from genomic HCMV DNA (AD169) and cloned into pCR3.1-Uni (Invitrogen) and pcDNA3myc. The cDNA clone for $UL37_M$ was generated by PCR from cDNA prepared from HCMV (Towne strain)-infected cells (27 hours post infection), and cloned into pCR3.1-Uni. The $pUL37_S\Delta2$-23 mutant was cloned into pcDNA3myc. The fidelity of PCR products and of cloning was confirmed by DNA sequencing.

Unless specified otherwise, transfections were performed with SuperFect (Qiagen, Valencia, Calif.) in accordance with the manufacturer's recommendations. Amphotropic replication-deficient retroviral vectors based on Moloney murine leukemia virus were generated by using the three-plasmid system for the transient production of high titer retroviral vectors (Soneoka et al., 1995, which is incorporated herein by reference). Some transfections were done with LipofectAMINE (GIBCO-BRL, Gaithersburg, Md.) with similar results.

Construction of HCMV DNA Libraries

A genomic DNA library was cloned into pZeoSV2(+) plasmid (Invitrogen). Ten cosmids, pCM1007, pCM1015, pCM1017, pCM1029, pCM1035, pCM1039, pCM1040, pCM1052, pCM1058, and pCM1072, covering the AD169 genome (Fleckenstein et al., 1982, which is incorporated herein by reference), and pON2601 Toledo cosmid (Cha et al., 1996, which is incorporated herein by reference) containing unique HCMV sequences, were mixed in equal amounts and partially digested with Sau3AI (New England Biolabs, Beverly, Mass.). Fragments of 2-5 kb were then size-selected on an agarose gel and ligated into the BamHI site of the eukaryotic expression vector pZeoSV2(+) (Invitrogen). The library complexity was $\sim3\times10^5$ colonies; with an average insert size 2.1 (the range 1.7-13 kb). 212 primary pools of approximately 500 colonies per pool were generated from the library. Plasmid DNA from each pool (0.7 µg/sample) and then $5\times10^4$ HeLa cells/well in 12 well plates were transfected with the mixtures by the SuperFect protocol. One day following transfection, cells were exposed to anti-Fas antibody (0.4 µg/mL)+CHX (10 µg/mL) for an additional 24 h. Cell-associated β-galactosidase was detected by a β-gal ELISA (Boehringer Mannheim).

A cDNA library was constructed as follows. MRC-5 fibroblasts were infected with HCMV AD169 at approximately 5-15 pfu/cell, then 27 h later mRNA was isolated using FastTrack 2.0 kit (Invitrogen) in accordance with the manufacturer's protocol, and then the first strand cDNA was synthesized with a SuperScript Preamplification System for First Strand cDNA Synthesis (GIBCO-BRL) in accordance with the manufacturer's protocol. This cDNA preparation was used for PCR.

Detection by Immunofluorescence and Immunoelectron Microscopy

HeLa cells were transfected with either pcDNA3/$UL37_S$myc, pcDNA/$UL37_S\Delta2$-23myc, or pcDNA3myc (negative control) by the SuperFect protocol. Cells were trypsinized, re-plated onto glass coverslips 24 h following transfection, and cultured for an additional 24 h. Cells were then fixed with 2% paraformaldehyde in phosphate-buffered saline (PBS) for 10 minutes, at room temperature, permeabilized by adding cold (−20° C.) methanol and incubating for 10 minutes, and rehydrated in PBS. Cells were then incubated, in succession, with: 1) PBS/5% NGS (blocking buffer) for 1 h, at room temperature; 2) 0.2 µg/mL 9E10 anti-myc antibody in blocking buffer for 1 h, at room temperature; 3) 0.2 µg/mL 9E10 anti-myc antibody in blocking buffer for 1 h, at room temperature; 4) goat anti-mouse IgG-FITC (Southern Biotechnology, Inc.) diluted 1:200 in blocking buffer containing 5 ng/mL Hoechst dye 33258 (Sigma) with PBS, and washed with PBS following each incubation step.

For MitoTracker staining, cells were incubated in MitoTracker Red (Molecular Probes) for 15 minutes prior to fixation, according to the manufacturer's instructions. For counterstaining with human anti-mitochondrial auto-antiserum (ImmunoVision), a 1:5000 dilution of the anti-mitochondrial antiserum was added simultaneously with the anti-myc, and detected using goat anti-human IgG-Texas Red (1:1000 dilution, Southern Biotechnology Associates) mixed with the goat anti-mouse IgG-FITC used to detect the myc tag. Slides were mounted in polyvinyl mounting medium and photographed with a Nikon Eclipse 800 equipped for epifluorescence. For immuno-electron microscopy, cryosections of HeLa/$pUL37_S$myc were stained first with 9E10 anti-myc antibody and then with secondary antibody-gold conjugates as described previously (Xu et al., 1994, which is incorporated herein by reference).

Various Molecular Biology Methods

PCR, Western blot analysis, DNA sequencing, DNA cloning, and X-gal staining of cells for β-galactosidase detection was carried out using standard procedures described in Sambrook et al. (1989), which is incorporated herein by reference.

The invention claimed is:

1. A composition comprising a therapeutically effective amount of an agent, which is an antisense oligonucleotide which binds to a polynucleotide which encodes human cytomegalovirus pUL37s, wherein the therapeutically effective amount is an amount that restores apoptosis in CMV-infected cells.

2. The composition of claim 1, wherein said antisense oligonucleotide comprises a phosphorothioate backbone.

3. A pharmaceutical composition comprising a pharmaceutically-acceptable carrier or excipient, and a therapeutically effective amount of an agent, which is an antisense oligonucleotide which binds to a polynucleotide which encodes human cytomegalovirus pUL37s, wherein the therapeutically effective amount is an amount that restores apoptosis in CMV-infected cells.

4. The composition of claim 1, wherein said antisense oligonucleotide comprises at least 25 consecutive nucleotides of a polynucleotide which encodes human cytomegalovirus pUL37s.

5. The composition of claim 1, wherein said antisense oligonucleotide comprises methylphosphonate moieties.

6. The composition of claim 1, wherein said antisense oligonucleotide is soluble.

7. The composition of claim 1, wherein said antisense oligonucleotide comprises at least one modified internucleoside linkage.

8. The antisense composition of claim 7, wherein the modified internucleoside linkage is a phosphorothioate linkage.

9. The antisense composition of claim 1 wherein said antisense oligonucleotide comprises at least one modified nucleobase.

10. A method for modulating apoptosis in a cell expressing pUL37s, said method comprising: contacting said cell with a composition comprising a therapeutically effective amount of an agent, wherein said agent is an antisense oligonucleotide which binds to a polynucleotide which encodes human cytomegalovirus pUL37s, wherein the therapeutically effective amount is an amount that restores apoptosis in CMV-infected cells.

11. The method of claim 10, wherein said antisense oligonucleotide comprises a phosphorothioate backbone.

12. A method for modulating apoptosis, said method comprising: contacting a eukaryotic cell with an effective amount of a composition according to any one of claims 1 to 9.

13. The method of claim 10, wherein said composition comprises a pharmaceutically-acceptable carrier or excipient.

14. The method of claim 10, wherein said antisense oligonucleotide comprises at least 25 consecutive nucleotides of a polynucleotide which encodes human cytomegalovirus pUL37s.

15. The method of claim 10, wherein said antisense oligonucleotide comprises methyiphosphonate moieties.

16. The method of claim 10, wherein said antisense oligonucleotide is soluble.

17. The method of claim 10, wherein said antisense oligonucleotide comprises at least one modified internucleoside linkage.

18. The method of claim 10, wherein said antisense oligonucleotide comprises at least one modified internucleoside linkage, wherein said internucleoside linkage is a phosphorothioate linkage.

19. The method of claim 10, wherein said antisense oligonucleotide comprises at least one modified nucleobase.

* * * * *